(12) United States Patent
Dushin et al.

(10) Patent No.: US 11,712,480 B2
(45) Date of Patent: Aug. 1, 2023

(54) HETEROARYL SULFONE-BASED CONJUGATION HANDLES, METHODS FOR THEIR PREPARATION, AND THEIR USE IN SYNTHESIZING ANTIBODY DRUG CONJUGATES

(71) Applicant: PFIZER INC., New York, NY (US)

(72) Inventors: Russell George Dushin, Old Lyme, CT (US); Daniel P. Uccello, Colchester, CT (US); Jeremy Starr, Mystic, CT (US); Ye Che, Niantic, CT (US); Mark Flanagan, Gales Ferry, CT (US); Jeffrey M. Casavant, Franklin, CT (US); Christopher John O'Donnell, Mystic, CT (US); Gary Frederick Filzen, Schwenksville, PA (US); Jennifer Young, Groton, CT (US); Joseph A. Abramite, San Diego, CA (US); Lawrence N. Tumey, Pawcatuck, CT (US); Ludivine Moine, Uncasville, CT (US); Adam Matthew Gilbert, Guilford, CT (US); Lee R. Roberts, Cambridge, MA (US)

(73) Assignee: Pfizer Inc., New York, NY (US)

( * ) Notice: Subject to any disclaimer, the term of this patent is extended or adjusted under 35 U.S.C. 154(b) by 854 days.

(21) Appl. No.: 16/321,695

(22) PCT Filed: Jul. 31, 2017

(86) PCT No.: PCT/IB2017/054675
§ 371 (c)(1),
(2) Date: Jan. 29, 2019

(87) PCT Pub. No.: WO2018/025168
PCT Pub. Date: Feb. 8, 2018

(65) Prior Publication Data
US 2021/0308276 A1 Oct. 7, 2021

Related U.S. Application Data

(60) Provisional application No. 62/530,554, filed on Jul. 10, 2017, provisional application No. 62/370,270, filed on Aug. 3, 2016.

(51) Int. Cl.
| A61K 47/54 | (2017.01) |
| A61K 47/68 | (2017.01) |
| C07K 4/00 | (2006.01) |
| C07K 5/02 | (2006.01) |
| C07K 7/02 | (2006.01) |
| A61K 47/50 | (2017.01) |
| C07K 5/062 | (2006.01) |

(52) U.S. Cl.
CPC .......... A61K 47/6855 (2017.08); A61K 47/50 (2017.08); A61K 47/545 (2017.08); A61K 47/6867 (2017.08); C07K 4/00 (2013.01); C07K 5/0205 (2013.01); C07K 5/06052 (2013.01); C07K 7/02 (2013.01)

(58) Field of Classification Search
CPC ........ A61K 38/02; A61K 38/03; A61K 38/07; A61K 47/545; A61K 47/6855; A61K 47/6867; C07K 4/00; C07K 5/0205; C07K 7/00; C07K 7/02
See application file for complete search history.

(56) References Cited

U.S. PATENT DOCUMENTS

| 4,816,397 | A | 3/1989 | Boss et al. |
| 4,816,567 | A | 3/1989 | Cabilly et al. |
| 5,225,530 | A | 7/1993 | Bernardi et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,773,001 | A | 6/1998 | Hamann et al. |
| 6,214,345 | B1 | 4/2001 | Firestone et al. |
| 8,039,273 | B2 | 10/2011 | Jeffrey |
| 8,568,728 | B2 | 10/2013 | Jeffrey |
| 2003/0013125 | A1* | 1/2003 | Braisted ............... C07D 333/70 435/7.1 |

FOREIGN PATENT DOCUMENTS

| EP | 0171496 A2 | 2/1986 |
| EP | 0173494 A2 | 3/1986 |

(Continued)

OTHER PUBLICATIONS

Erlanson et al. In situ assembly of enzyme inhibitors using extended tethering. Nature Biotechnology. Mar. 2003, vol. 21, pp. 308-314. (Year: 2003).*

(Continued)

Primary Examiner — Jeffrey E. Russel
(74) Attorney, Agent, or Firm — Saul Ewing LLP; Domingos J. Silva

(57) ABSTRACT

The present invention is directed to novel heteroaryl sulfone-based conjugation handles of the formula:

(I)

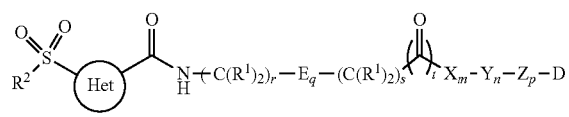

(wherein $R^1$, $R^2$, Het, D, E, X, Y, Z, m, n, p, q, r, s and t are as defined herein), methods for their preparation, their use in synthesizing antibody drug conjugates, and the resulting antibody drug conjugates made with components having heteroaryl sulfone-based conjugation handles.

8 Claims, No Drawings

(56) References Cited

FOREIGN PATENT DOCUMENTS

| | | | |
|---|---|---|---|
| EP | 0184187 A2 | | 6/1986 |
| EP | 0404097 A2 | | 12/1990 |
| JP | 2005330229 A | * | 12/2005 |
| WO | 86/01533 A1 | | 3/1986 |
| WO | 87/02671 A1 | | 5/1987 |
| WO | 93/11161 A1 | | 6/1993 |
| WO | 2012/059882 A2 | | 5/2012 |
| WO | 2013/068946 A2 | | 5/2013 |
| WO | 2013/093809 A1 | | 6/2013 |
| WO | 2014/068443 A1 | | 5/2014 |
| WO | 2014/144878 A2 | | 9/2014 |
| WO | 2015/015448 A2 | | 2/2015 |
| WO | 2015/110935 A1 | | 7/2015 |
| WO | 2015/162563 A1 | | 10/2015 |
| WO | 2016/030791 A1 | | 3/2016 |
| WO | 2016/151432 A1 | | 9/2016 |

OTHER PUBLICATIONS

Singh et al. Metabolic Activation of a Pyrazinone-Containing Thrombin Inhibitor. Chemical Research in Toxicology. 2003, vol. 16, No. 2, pp. 198-207. (Year: 2003).*
Alley et al., "Contribution of Linker Stability to the Activities of Anticancer Immunoconjugates", Bioconjugate Chem., 2008, 759-765, 19.
Beidler et al., Cloning and High Level Expression of a Chimeric Antibody with Specificity for Human Carcinoembryonic Antigen:, Journal of Immunology, 1988, 4053-4060, 11.
Better et al., "*Escherichia coli* Secretion of an Active Chimeric Antibody Fragment", Science, 1988, 1041-1043, 240.
Chothia et al., "Canonical Structures for the Hypervariable Regions of Immunoglobulins", J Molecular Biology, 1987, 901-917, 196.
Holliger et al., "Diabodies": Small bivalent and bispecific antibody fragments, PNAS, 1993, 6444-6448, 90.
Hoogenboom et al., "Human Antibodies from Synthetic Repertoires of Germline VH Gene Segments Rearranged in vivo", J. Molecular Biology, 1992, 381-388, 227.
Jespers et al., "Guiding the Selection of Human Antibodies from Phage Display Repertoires to a Single Epitope of an Antigen", BioTechnology, 1994, 899-903, 12.
Jones et al., "Replacing the complementarity-determining regions in a human antibody with those from a mouse", Nature, 1986, 522-525, 321.
Kabat, "Origins of Antibody Complementarity and Specificity—Hypervariable Regions and the Minigene Hypothesis", The Journal of Immunology, 1980, 961-969, 125(3).
Kozbor et al., "The production of monoclonal antibodies from human lymphocytes", Immunology Today, 1983, 72-79, 4(3).
Laguzza et al., "New Antitumor Monoclonal Antibody-Vinca Conjugates LY203725 and Related Compounds Design, Preparation, and Representative in Vivo Activity", 1989, 548-555, 32.
Langer, "New Methods of Drug Delivery", Science, 1990, 1527-1533, 249.
Liu et al., "Production of a Mouse-Human Chimeric Monoclonal Antibody to CD20 with Potent Fc-Dependent Biologic Activity", 1987, 3521-3526, 139(10).
Liu et al., "Chimeric mouse-human IgG1 antibody that can mediate lysis of cancer cells", PNAS, 1987, 3439-3443, 84.
Lonberg et al., "Human Antibodies from Transgenic Mice", Intern. Rev. Immunol., 1995, 65-93, 13.
Marks et al., "By-Passing Immunization. Human Antibodies from V-gene Libraries Displayed on Phage", Journal of Molecular Biology, 1991, 581-597, 222.
Morrison, "Transfectomas Provide Novel Chimeric Antibodies", Science, 1985, 1202-1207, 229.
Nishimura et al., "Recombinant Human-Mouse Chimeric Monoclonal Antibody Specific for Common Acute Lymphocytic Leukemia Antigen", Cancer Research, 1987, 999-1005, 47.
Oi et al., "Chimeric Antibodies", BioTechniques, 1986, 214-221, 4(3).
Olsson et al., "Human-Human Monoclonal Antibody-Producing Hybridomas: Technical Aspects", Methods in Enzymology, 1982, 3-16, 92.
Riechmann et al., "Reshaping human antibodies for therapy", Nature, 1988, 323-327, 332.
Shaw et al., "Mouse/Human Chimeric Antibodies to a Tumor-Associated Antigen: Biologic Activity of the Four Human IgG Subclasses", Journal of the National Cancer Institute, 1988, 1553-1559, 80.
Sun et al., "Chimeric antibody with human constant regions and mouse variable regions directed against carcinoma-associated antigen 17-1A", PNAS, 1987, 214-218, 84.
Teng et al., "Construction and testing of mouse-human heteromyelomas for human monoclonal antibody production", PNAS, 1983, 7308-7312, 80.
Verhoeyen et al., "Reshaping Human Antibodies: Grafting an Antilysozyme Activity", Science, 1988, 1534-1536, 239.
Wood et al., "The synthesis and in vivo assembly of functional antibodies in yeast", Nature, 1985, 446-449, 314.
Toda et al., "Rapid, Stable, Chemoselective Labeling of Thiols with Julia-Kocienski-like Reagents: A Serum-Stable Alternative to Maleimide-Based Protein Conjugation", Angewandte Communications, 2013, 12592-12596, 52, with supporting documentation.
Li et al., "Site-Specific Dual Antibody Conjugation via Engineered Cysteine and Selenocysteine Residues", Bioconjugate Chemistry, 2015, 2243-2248, 26, with supporting documentation.
Patterson et al., "Improving the Serum Stability of Site-Specific Antibody Conjugates with Sulfone Linkers", Bioconjugate Chemistry, 2014, 1402-1407, 25, with supporting documentation.
International Search Report dated Oct. 27, 2017 for International application No. PCT/IB2017/054675, filed Jul. 31, 2017.
Written Opinion of the International Searching Authority for International application No. PCT/IB2017/054675, filed Jul. 31, 2017.

* cited by examiner

HETEROARYL SULFONE-BASED CONJUGATION HANDLES, METHODS FOR THEIR PREPARATION, AND THEIR USE IN SYNTHESIZING ANTIBODY DRUG CONJUGATES

CROSS-REFERENCE TO RELATED APPLICATIONS

This Application is the national stage filing under 35 U.S.C. 371 of Patent Cooperation Treaty Patent Application No. PCT/IB2017/054675, filed Jul. 31, 2017, which claims the benefit of priority from U.S. Provisional Application No. 62/370,270 filed Aug. 3, 2016, and U.S. Provisional Application No. 62/530,554 filed Jul. 10, 2017.

FIELD OF THE INVENTION

The present invention is directed to novel linker compounds and moieties which are incorporated into, and which are useful for making polypeptide conjugates, including antibody-drug-conjugates (ADCs), and related linker-payload compounds (LPs). The present invention further relates to compositions including the aforementioned linkers, linker-payloads and antibody drug conjugates, and methods for using these payloads, payload-linkers and antibody drug conjugates to treat pathological conditions including cancer.

BACKGROUND

The antibody drug conjugate (ADC) is a therapeutic modality consisting of a monoclonal antibody attached to small molecule cytotoxic payloads. The antibody portion of the ADC serves as a transport vehicle that recognizes and binds to a protein antigen expressed in tumor tissues. The localized delivery and release of the payload within or near malignant cells allows for targeted delivery of a potent cytotoxic agent to diseased tissue, while reducing damage to antigen-negative, normal tissues. ADCs design seeks to combine the strengths of large and small molecule drugs and eliminate weaknesses associated with each approach. Thus, many ADCs are designed to minimize the systemic toxicity of the free drug and to augment the antitumor activity of the targeting vehicle, such as monoclonal antibodies (mAbs).

A number of ADCs currently under investigation contain maleimide-based linkers. In these ADCs, antibody conjugation is typically accomplished as shown below:

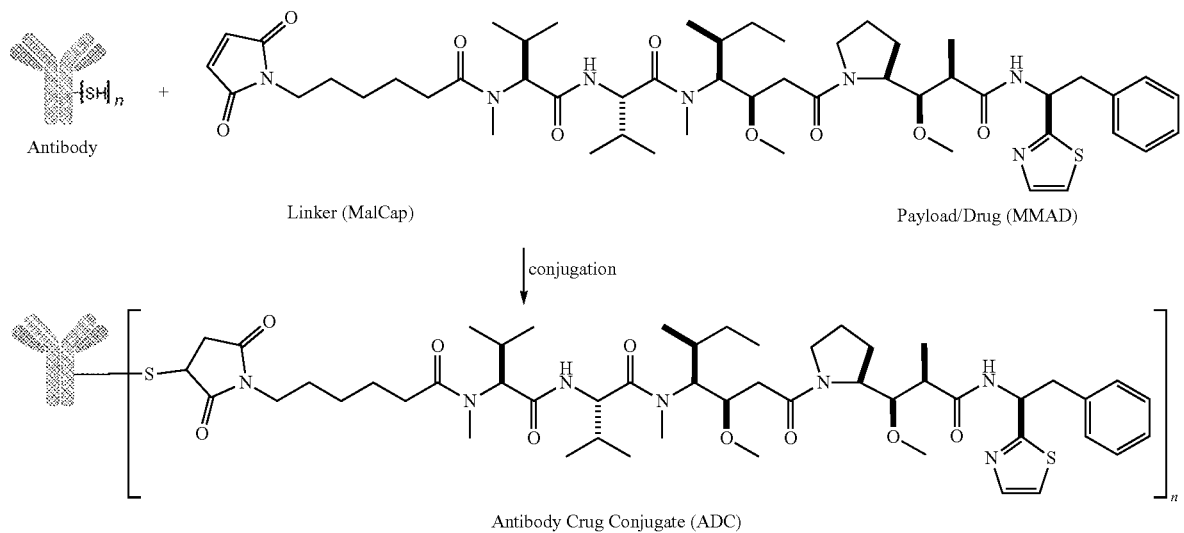

Antibody Crug Conjugate (ADC)

Exemplary ADC based on Maleimidocaproyl (MalCap or mc) linker and monomethyl auristatin D (MMAD) payload.

The use of such conjugation in numerous investigational ADC constructs can be attributed to maleimide's high reactivity and selectivity for cysteine residues. More specifically, ADCs may be constructed by incubating the antibody with a linker-payload containing a maleimide conjugation handle, which reacts with the exposed thiols of the antibody.

There are, however, numerous examples of instability directly associated with the maleimide moiety. For example, researchers at Seattle Genetics have demonstrated that the maleimide-based ADCs known as 1F6-C4v2-mc-MMAF and 1F6-C4v2-mc-vc-MMAF undergo decomposition (as manifested in reduced drug-antibody ratios) upon exposure to plasma proteins with half lives of approximately 7 days. (Alley et al. "Contribution of Linker Stability to the Activities of Anticancer immunoconjugates" *Bioconjugate Chem.* 2008, 19, 759.) Alley further provides mass spectrometry evidence for serum albumin mc-MMAF adduct formation, which is thought to occur through thioether fragmentation of the ADC and subsequent capture of the regenerated maleimide with albumin at Cys34, as shown here:

Linker-payload (mc-MMAF) exchange with serum albumin

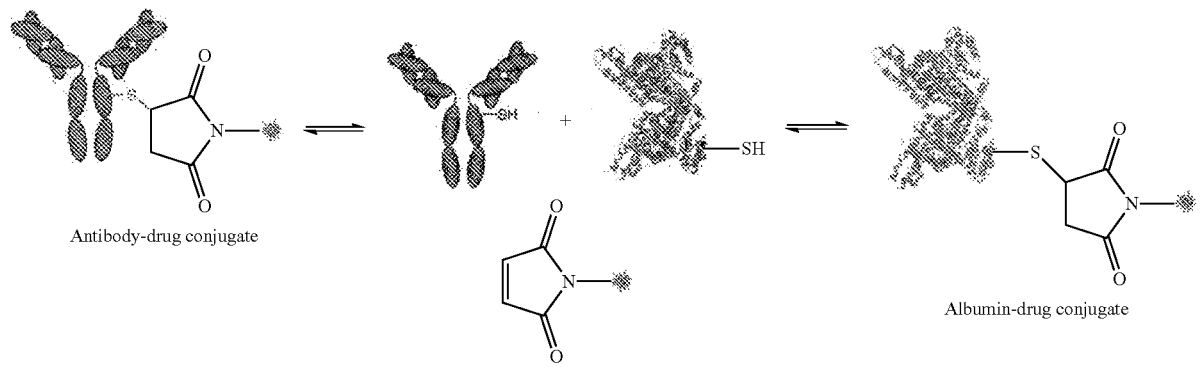

It has likewise been demonstrated, through plasma stability assays and glutathione (GSH) incubation studies that similar maleimide-related instability exists where ADCs have been shown to undergo reduction in drug antibody ratios (DARs) in the presence of GSH, as shown in below:

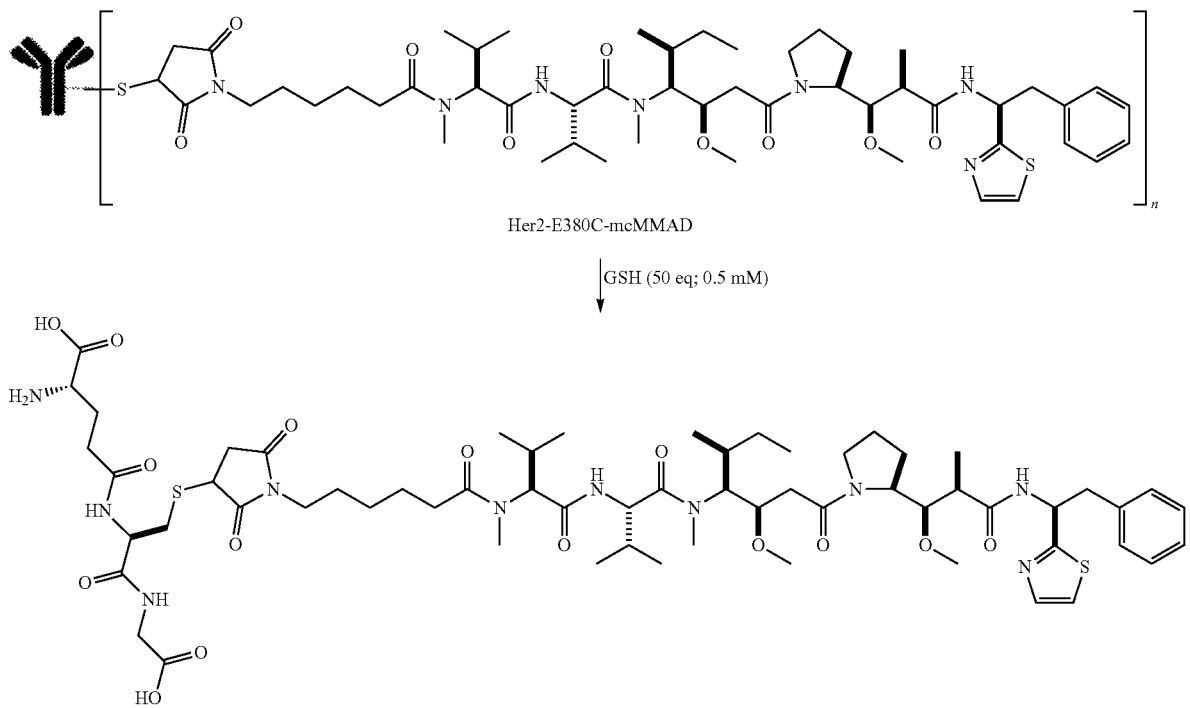

In view of the foregoing, it would be advantageous to develop and employ a linker technology that possesses comparable high selectivity and reactivity to cysteine but avoids the instability associated with maleimide linker components.

SUMMARY OF THE INVENTION

The present invention relates to non-maleimide-based ADC linkers and linker components, their preparation, and their use in preparing ADCs more stable than corresponding maleimide-based ADCs. In many instances this improved stability will result in ADCs having improved therapeutic indicies and/or other advantageous properties.

The invention thus provides specific cysteine-selective covalent reactive groups (CRGs) to serve as versatile conjugation handles (able to undergo complete conjugation with any antibody of interest, typically within about one day) that provide stable achiral ADC linkers having substantially unchanged DARs under physiological conditions beyond one week.

The invention also relates to non-maleimide-based linkers and linker components used beyond the ADC field, including in the linking and conjugation of other biological components, such as peptides, proteins, RNA (including mRNA, siRNA), and single and double stranded DNA, which may or may not comprise cysteine-containing, or simply sulphur-containing moieties.

The invention also relates to non-maleimide-based linkers and linker components used beyond the ADC field, including in the linking and conjugation of multiple biological components, such as peptides, proteins, RNA (including mRNA, siRNA), and single and double stranded DNA, which may or may not comprise cysteine-containing, or simply sulphur-containing moieties, to one another.

The invention also relates to non-maleimide-based linker components used in the ADC field, and beyond the ADC field, specifically linker-payloads comprising a heterocycle linker bound to a sulfone and an amide and having the formula (I):

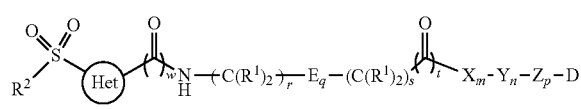

(I)

and pharmaceutically acceptable salt or solvate thereof, wherein:

Het is a mono-, bi- or polycyclic heteroaryl ring system having 1-4 heteroatoms, where a carbon atom on said ring system bound to $-SO_2-$ is adjacent to at least one heteroatom on said ring system, and where said heteroatoms are selected from the group consisting of N, O and S;

each E is independently selected from the group consisting of: $-C(R^1)_2-$, $-O-C(R^1)_2-C(R^1)_2-$ where r is at least 2, and $-C(R^1)_2-C(R^1)_2-O-$ where s is at least 1;

each $R^1$ is independently selected from the group consisting of: H, $C_1$-$C_6$ straight or branched alkyl, $C_2$-$C_6$ straight or branched alkenyl, and $C_2$-$C_6$ straight or branched alkynyl;

$R^2$ is $C_1$-$C_{10}$ alkyl optionally substituted with a halogen or haloalkyl, or $C_5$-$C_{12}$ aryl optionally substituted with a halogen or haloalkyl;

each X is independently an amino acid, where each amino acid X is the same or is different;

each Y is independently an amino acid, where each amino acid Y is the same or is different;

each Z is independently a spacer element, where each spacer element is the same or is different;

m is 0 5, n is 0 5, p is 0 2, q is 0 10, r is 0 2, s is 0 2, t is 0-1 and w is 1-2;

and D is a cytotoxic agent.

In the above ambodiment w is preferably 1.

It has been found that such linkers-payloads, having a heterocycle bound to a sulfone and an amide, are able to form ADCs which are surprisingly stable compared to ADCs formed using maleimide linkers or even other non-maleimide linkers. Without wishing to be bound by theory, it is believed that such ADCs are typically formed (i.e., "conjugated") via the well-known $S_NAr$ reaction mechanism.

The invention further relates to ADCs formed using the above-described non-maleimide-based linker-payloads, wherein said ADCs have a heterocycle bound to an amide, and wherein such ADCs have the formula (II):

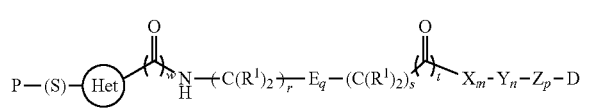

(II)

and pharmaceutically acceptable salt or solvate thereof, wherein:

P is a peptide sequence which includes at least one naurally occurring or engineered cysteine residue, or P is a moiety which includes at least one free sulfur atom;

S is a sulfur atom within P;

Het is a mono-, bi- or polycyclic heteroaryl ring system having 1-4 heteroatoms, where a carbon atom on said ring system bound to $-S(O_2)-$ is adjacent to at least one heteroatom on said ring system, and where said heteroatoms are selected from the group consisting of N, O and S;

each E is independently selected from the group consisting of: $-C(R^1)_2-$, $-O-C(R^1)_2-C(R^1)_2-$ where r is at least 2, and $-C(R^1)_2-C(R^1)_2-O-$ where s is at least 1;

each $R^1$ is independently selected from the group consisting of: H, $C_1$-$C_6$ straight or branched alkyl, $C_2$-$C_6$ straight or branched alkenyl, and $C_2$-$C_6$ straight or branched alkynyl;

each X is independently an amino acid, where each amino acid X is the same or is different;

each Y is independently an amino acid, where each amino acid Y is the same or is different;

each Z is independently a spacer element, where each spacer element is the same or is different;

m is 0 5, n is 0 5, p is 0 2, q is 0 10, r is 0 2, s is 0 2, t is 0-1 and w is 1-2;

and D is a cytotoxic agent.

In the above embodiment w is preferably 1.

The invention also relates to the aforementioned linker-payloads and ADCs wherein the Het variable is selected from:

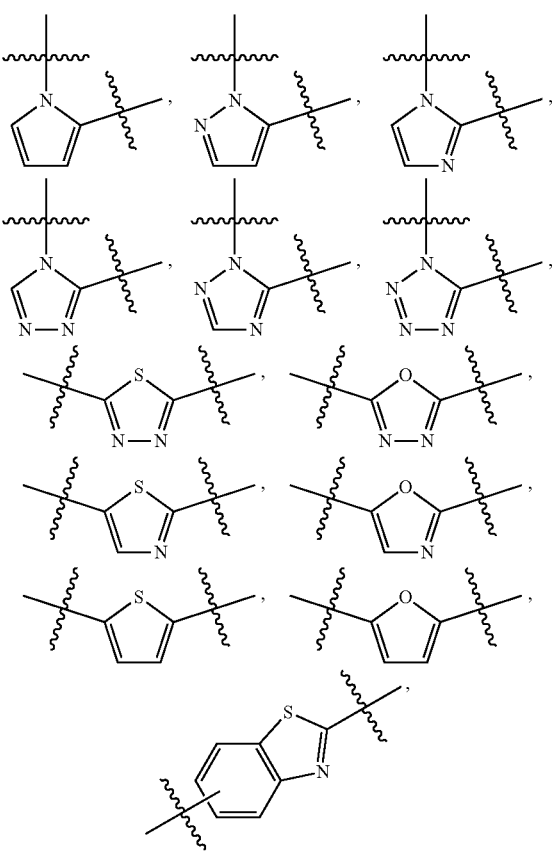

-continued

-continued

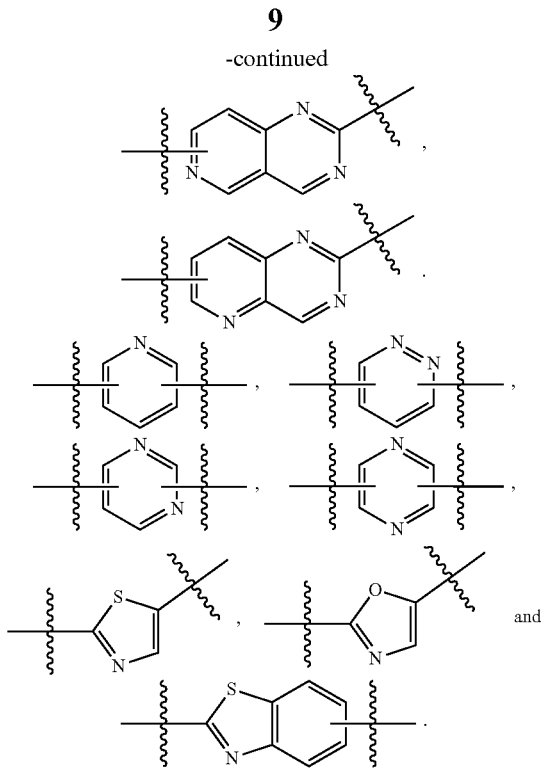

The invention further relates to the aforementioned linker-payloads and ADCs wherein the Het variable is selected from:

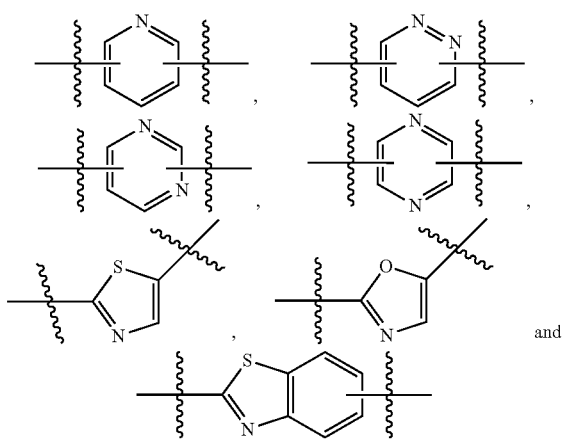

and

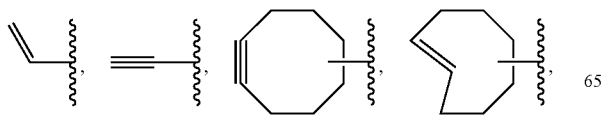

wherein the either bond on the selected Het may join with S (i.e., the Het structures can "face" in either direction).

In another embodiment of the invention there is provided a compound identified herein, or a pharmaceutically acceptable salt or solvate thereof, wherein:

D is selected from the group consisting of: substituted or unsubstituted alkyl, substituted or unsubstituted aryl, —(OCH$_2$CH$_2$)p-, —CO$_2$H, —NH$_2$, OH, —N$_3$, -continued

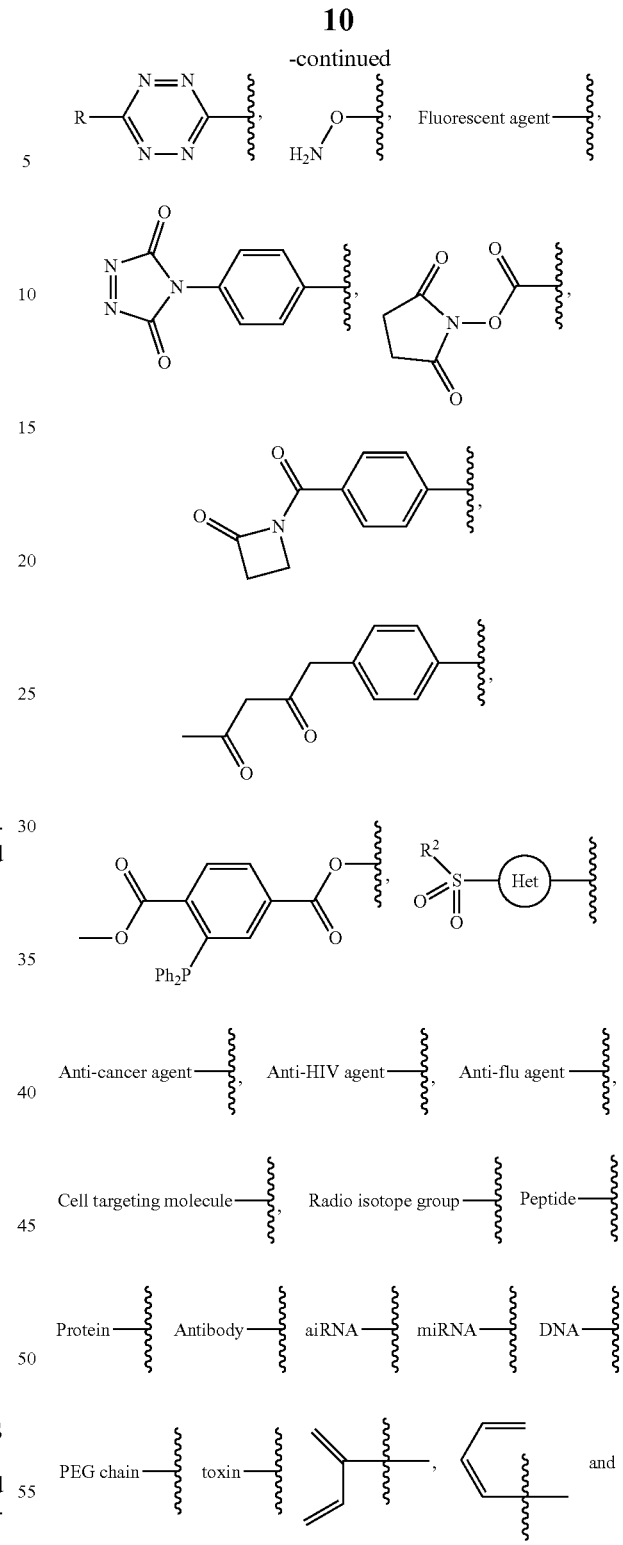

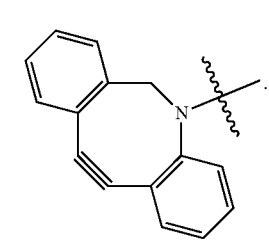

In an aspect of this embodiment there is provided a comound identified herein or a pharmaceutically acceptable salt or solvate thereof, wherein D is a cytotoxic moiety. In another aspect there is provided the compound of claim 6, or a pharmaceutically acceptable salt or solvate thereof, wherein D is selected from the group consisting of: an anthracycline, an auristatin, a spliceostatin, a CBI dimer, a CPI dimer, a CTI dimer (including "mixed" dimers comprising CBI, CPI and/or CTI dimers components, as described in international patent applications PCT/IB2015/050280 (WO2015/110935) and PCT/IB2016/051465), an enediyne (such as a calicheamicin, an esperamycin or a neocarzinostatin), a duocarmycin, a geldanamycin, a maytansine, a puromycin, a taxane, a vinca alkaloid, SN 38, a tubulysin, a hemiasterlin, a camptothecin, a combretastatin, a dolastatin, an indolino benzodiazepine dimer, a pyrrolobenzodiazepine dimer and a pladienolide, and stereoisomers, isosteres, analogs, or derivatives thereof. For instance, embodiments wherein the cytotoxic agent D is an auristatin selected from the group consisting of dolestatin, MMAD, MMAE, MMAF, PF-06380101, PF-06463377, PF-06456780, PF-06843982, PF-06874082, PF-06852321, PF-06757725, PF-06859944 and PF-06698970.

Additional embodiments of the invention include those wherein D is something other than a cytotoxic agent, for instance where D is a moiety having therapeutic properties (i.e., a therapeutic agent) and includes peptide(s), protein(s), nucleic acid(s), growth factor(s), anti-viral agent(s), or (an) immunological agent(s), or D is a fluorophore(s) or other imaging agent(s). As is the case where D is a cytotoxic agent, the invention includes the stability modulation of compounds wherein D is other than a cytotoxic agent.

In yet another embodiment of the invention there is provided a compound as described herein, or a pharmaceutically acceptable salt or solvate thereof, wherein:

Z is $Z^A$—$(Z^B)_{1-3}$ or $(Z^B)_{1-3}$—$Z^A$, where $Z^A$ is $Z^{A1}$—$Z^{A2}$ or $Z^{A2}$—$Z^{A1}$, where $Z^{A1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$-alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$—, —C(O)$C_1C_6$alkyl(OCH$_2$CH$_2$)$_{1-6}$—NRC(O)$C_1$-$C_6$alkyl-, —S—, —C(O)—CH(NR—C(O)$C_1$-$C_6$alkyl)-$C_1$-$C_6$alkyl- and (—CH$_2$—CH$_2$—O')$_{1-20}$, where $Z^{A2}$ is -PABA-, -PABC-, —C(O)(CH$_2$)$_n$C(O)— or absent; and where $Z^B$ is absent or independently selected from the group consisting of —$C_1$-$C_6$alkylene-, —NR$C_3$-$C_8$-heterocyclylNR-, —NR$C_3$-$C_8$-carbocyclylNR—, —NR$C_1$-$C_6$alkyl NR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —O$C_1$-$C_6$alkylS—S$C_1$-$C_6$alkylC(COOR)NR—, —NRC(COOR)$C_1$-$C_6$alkylS—S$C_1$-$C_6$alkylO—.

In still yet another embodiment of the invention there is provided a compound as described herein, or a pharmaceutically acceptable salt or solvate thereof, wherein:

Z is:

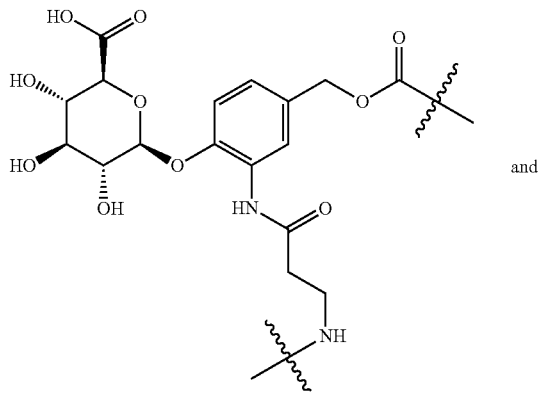 and

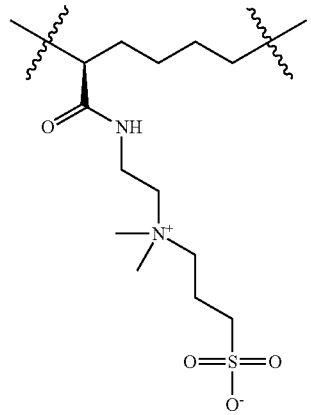

In a further embodiment of the invention there is provided a compound selected from:

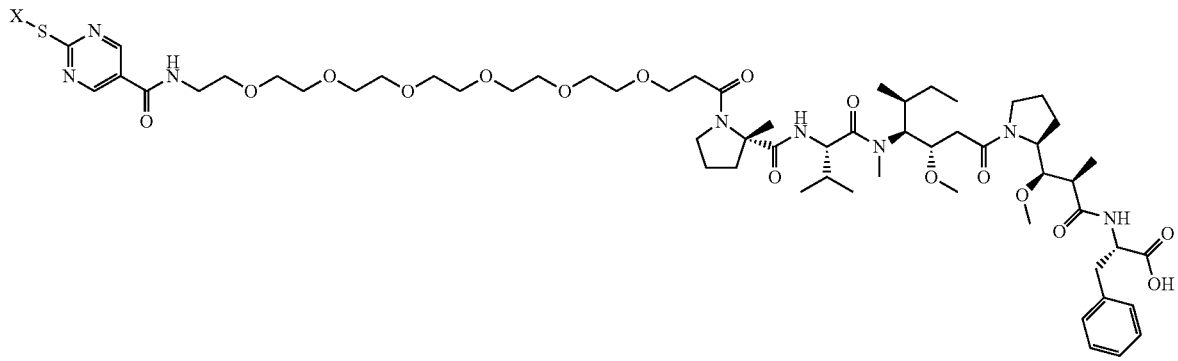

where X is H—(C)—,
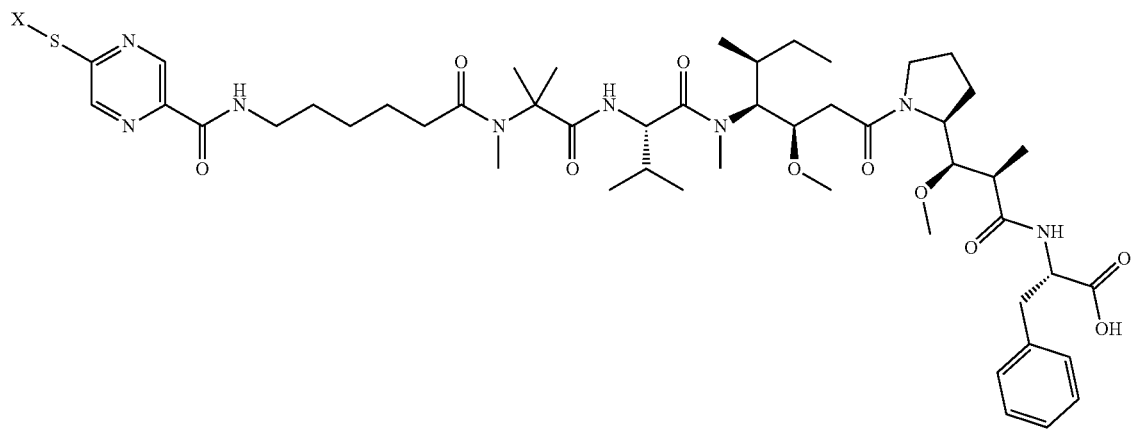
where X is H-(A114C)-,
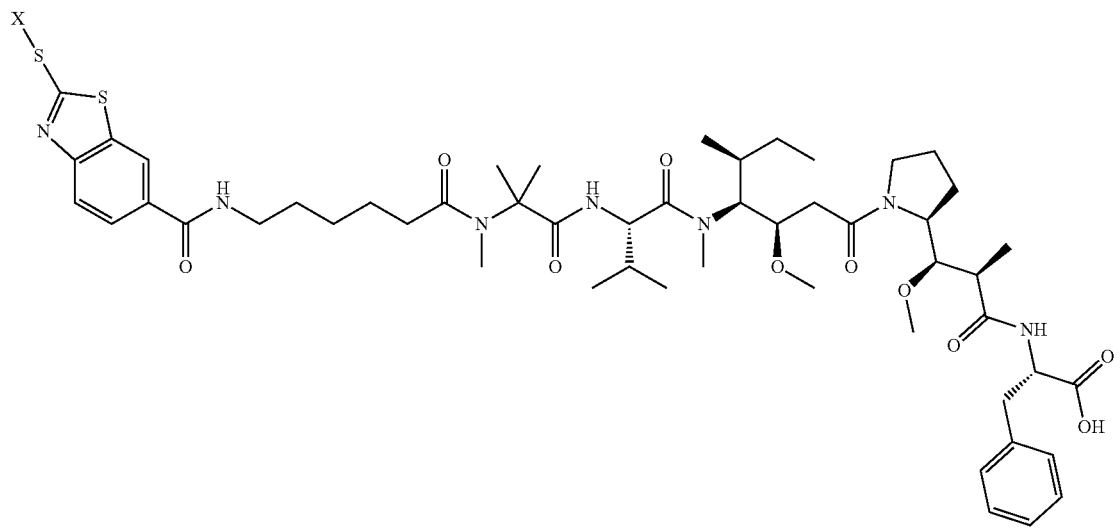
where X is H-(A114C)-,
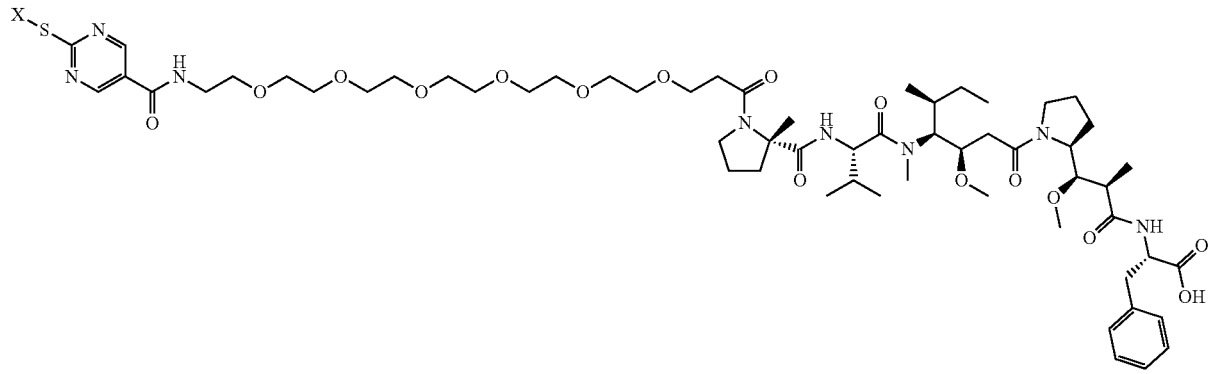

where X is H-(A114C)-,
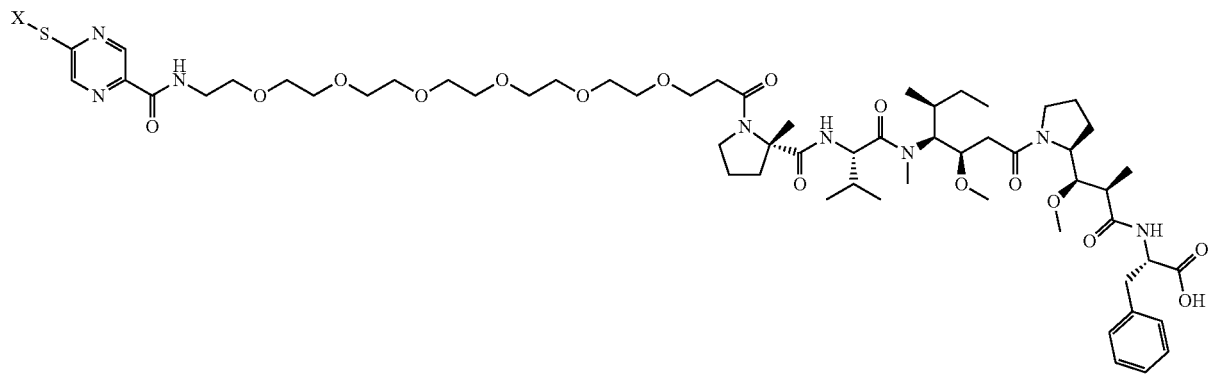
where X is H-(A114C)-,
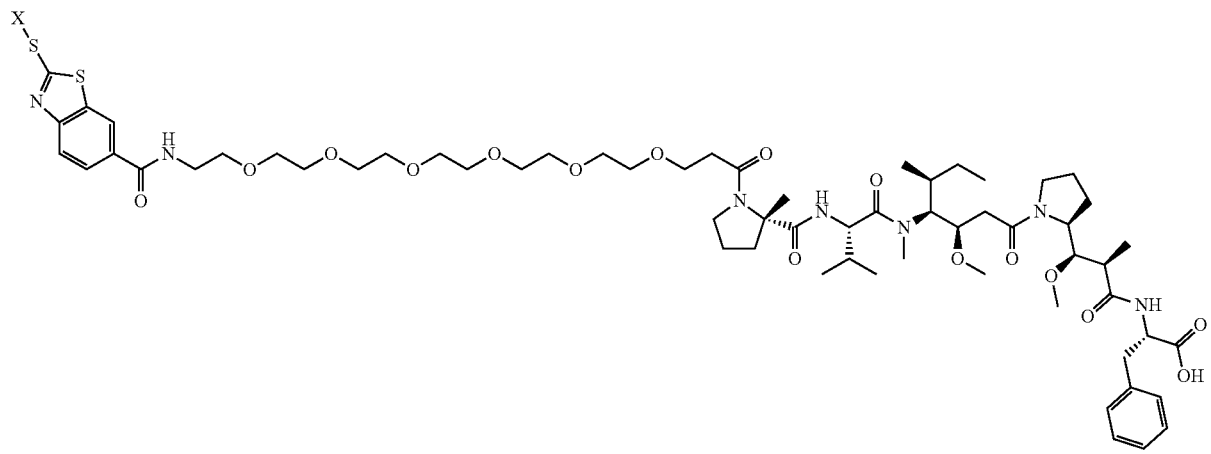
where X is H-(A114C)-,
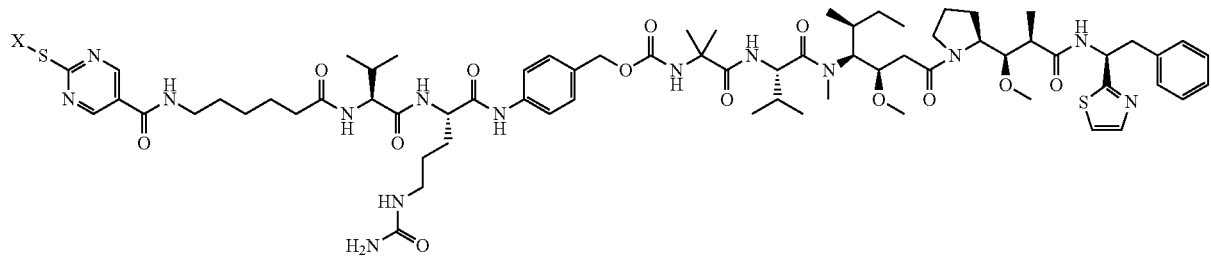
where X is H-(A114C)-,
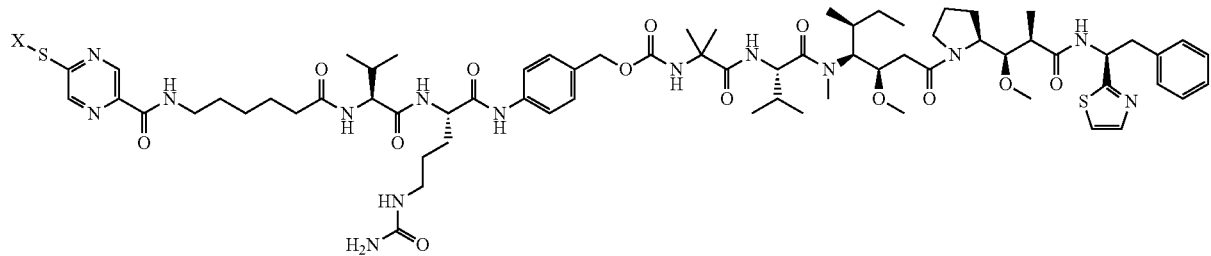

where X is H-(A114C)-,
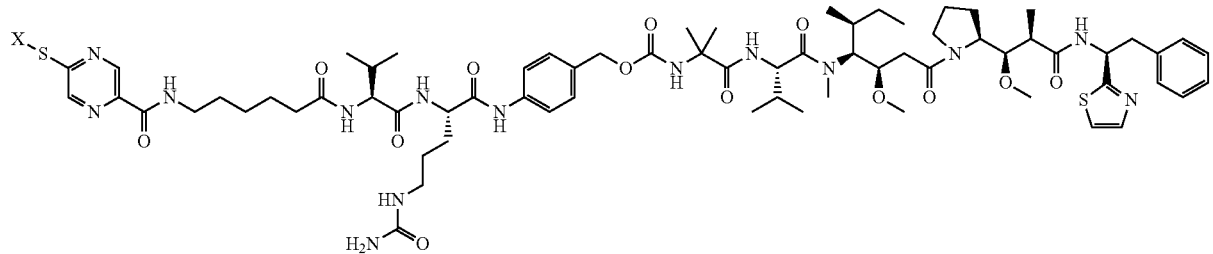
where X is H-(K183C)-,
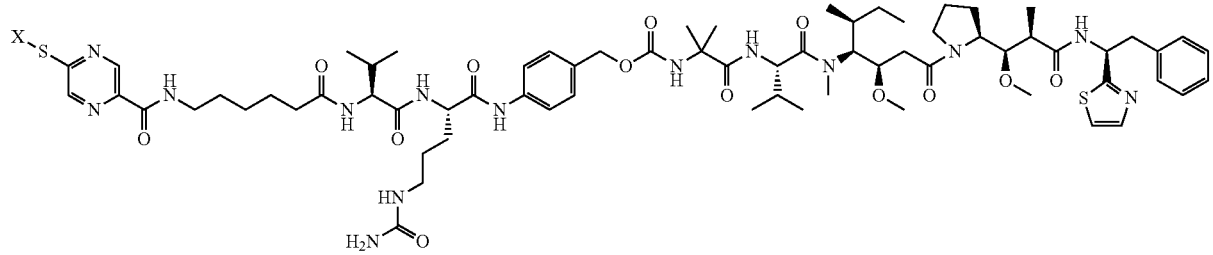
where X is H-(E380C)-,
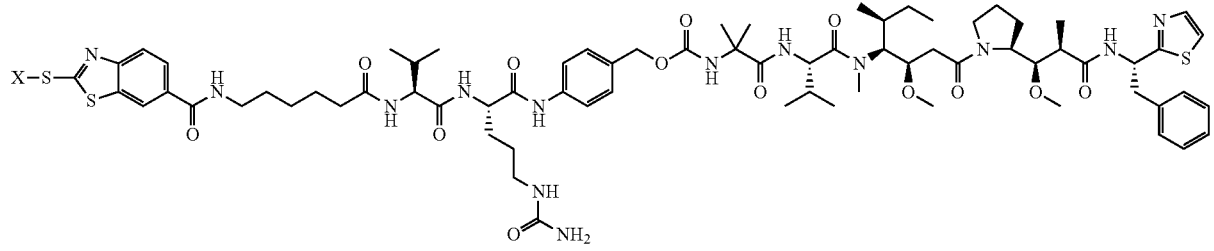
40
where X is H-(A114C)-,
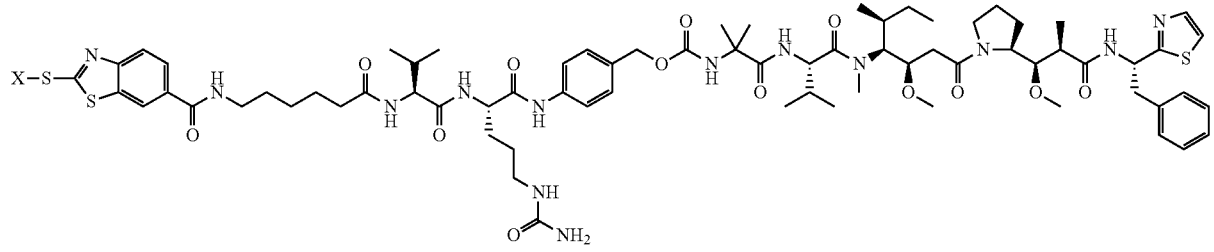
where X is H-(E380C)-,
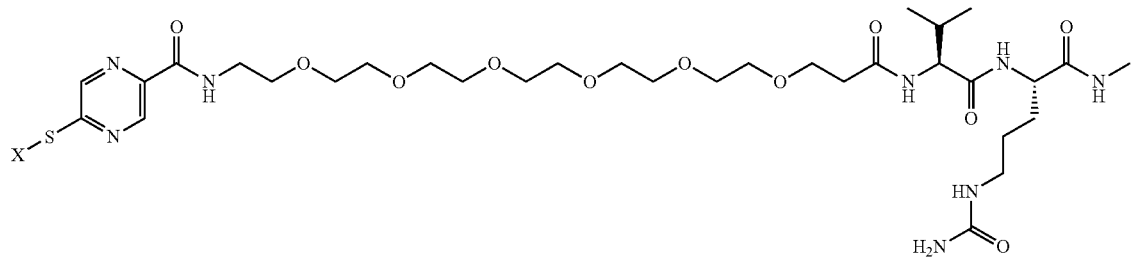

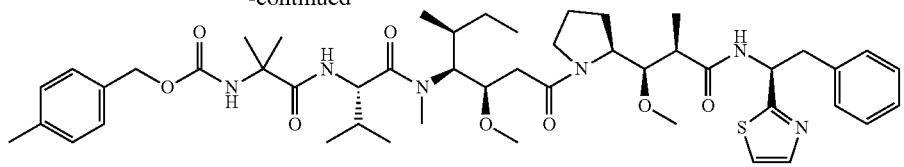
where X is H-(A114C)-,
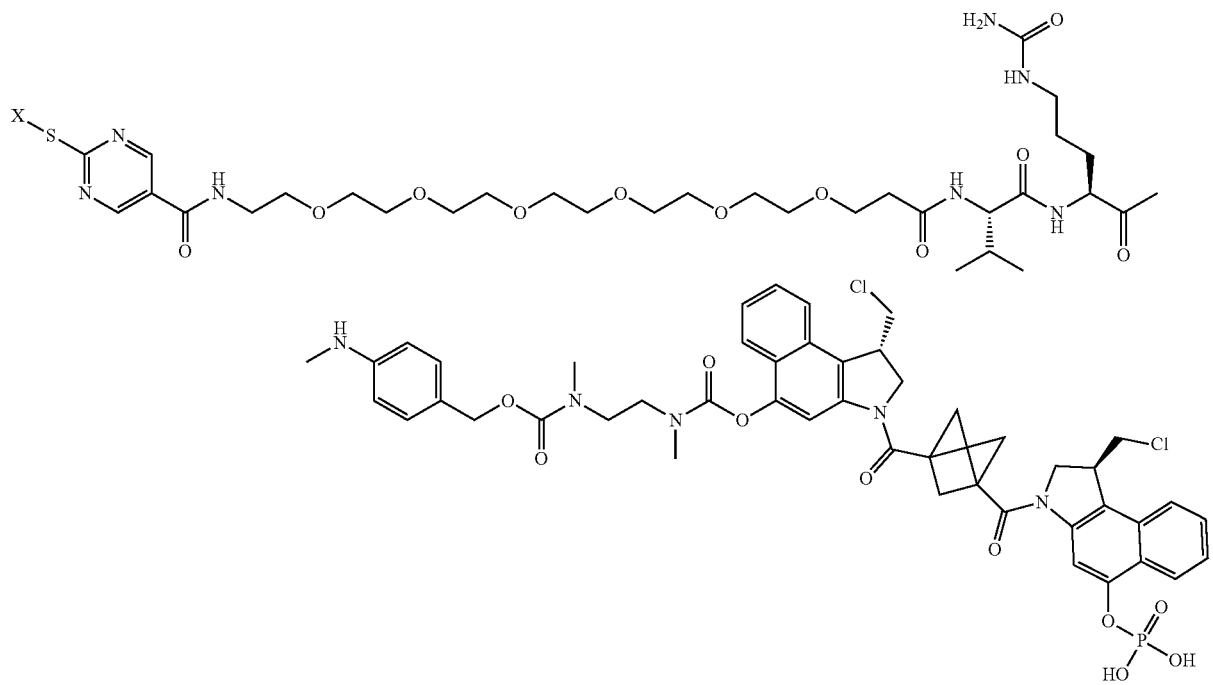
where X is CD33-11A1-v1417-(C)-,
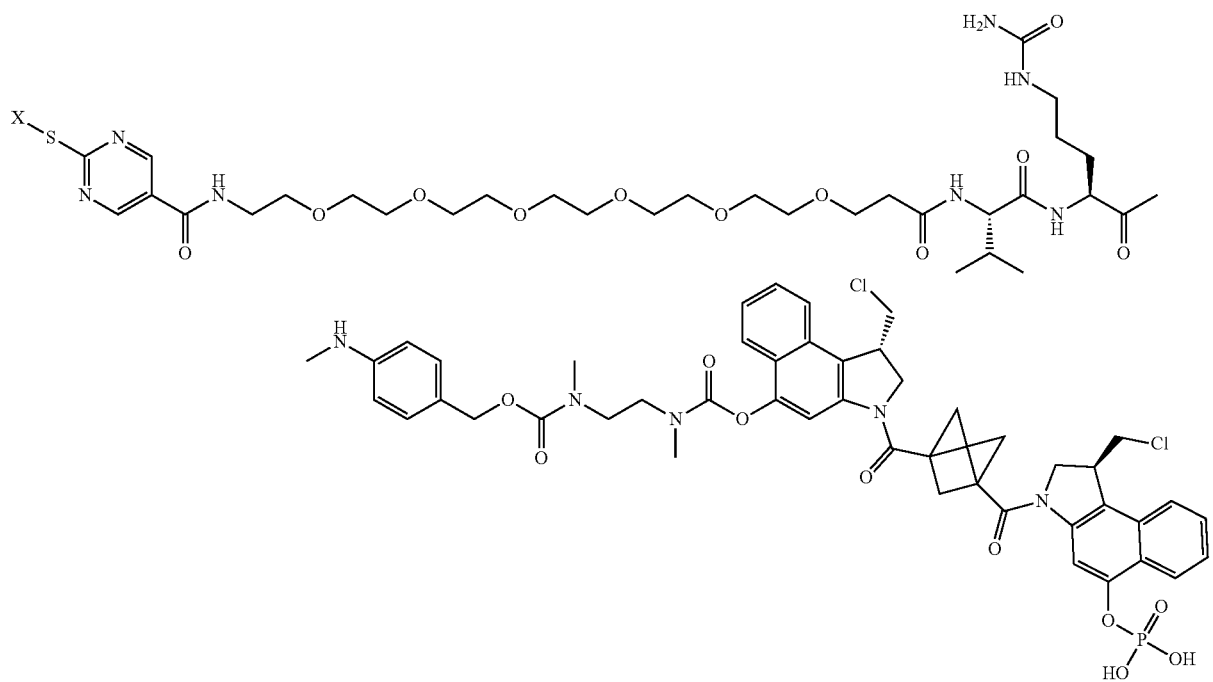

where X is CD33-11A1-v1417-(K290C)-(K334C)-,
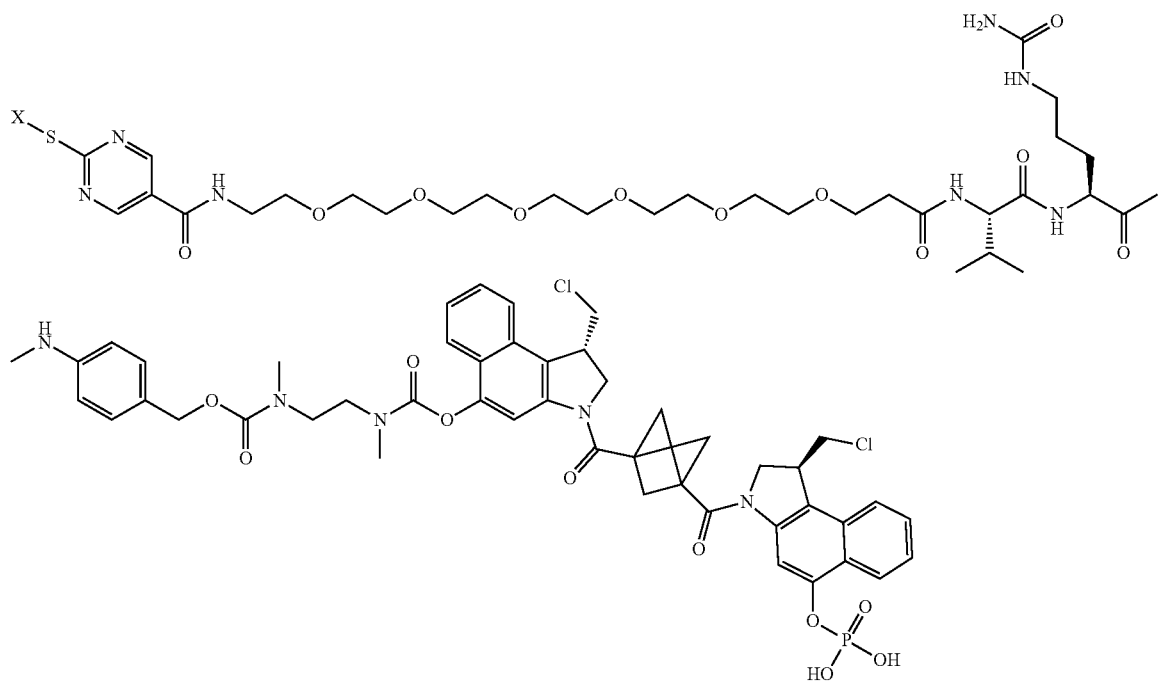
where X is CD33-11A1-v1417-(K334C)-(K392C)-,
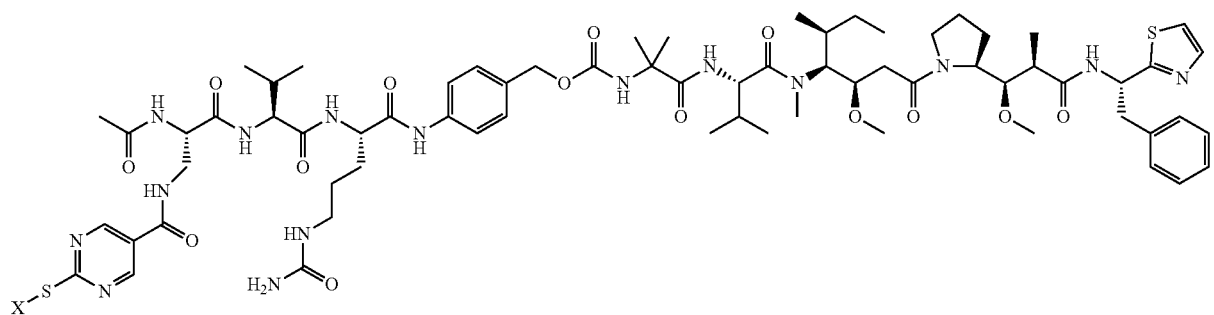
where X is H-(A114C)-,
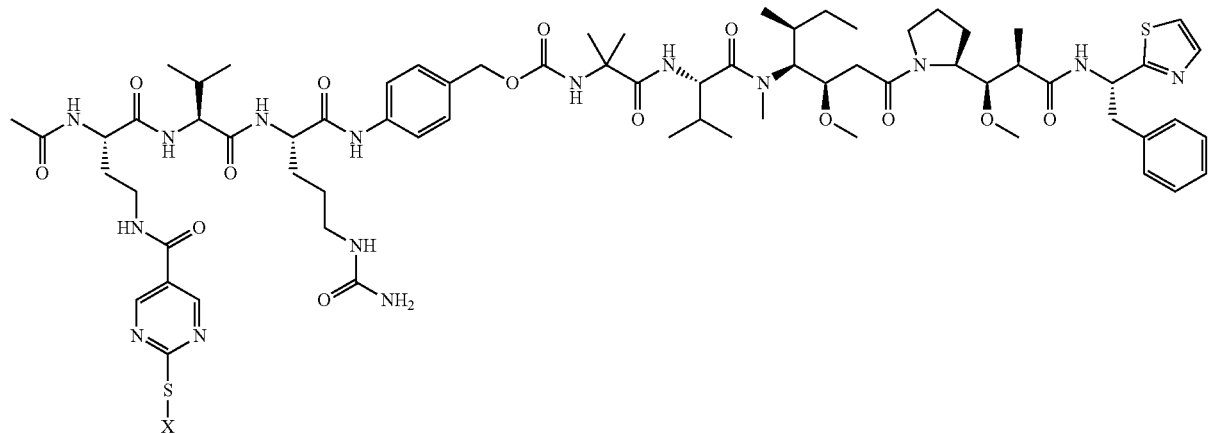

where X is H-(A114C)-,

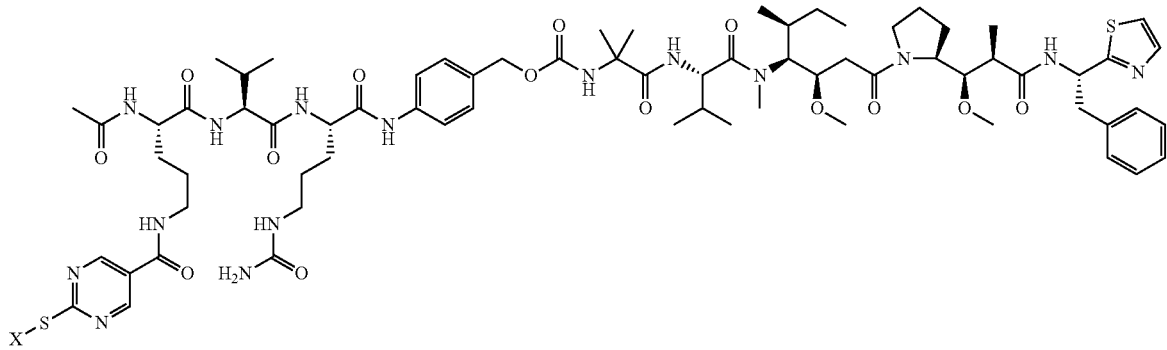

where X is H-(A114C)-,

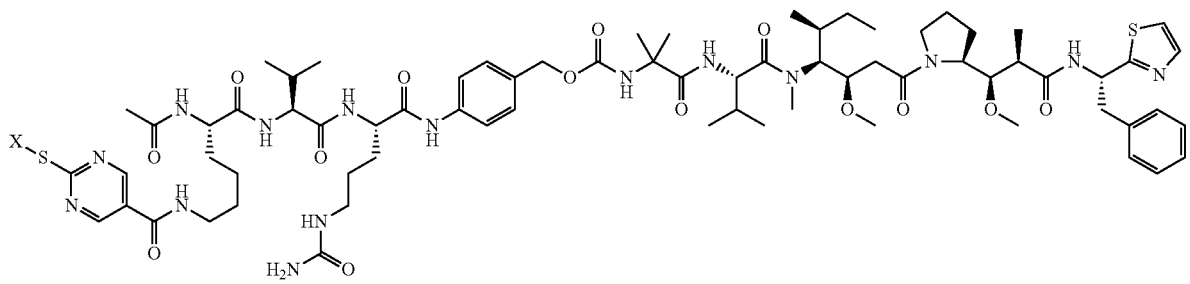

where X is H-(A114C)-, and

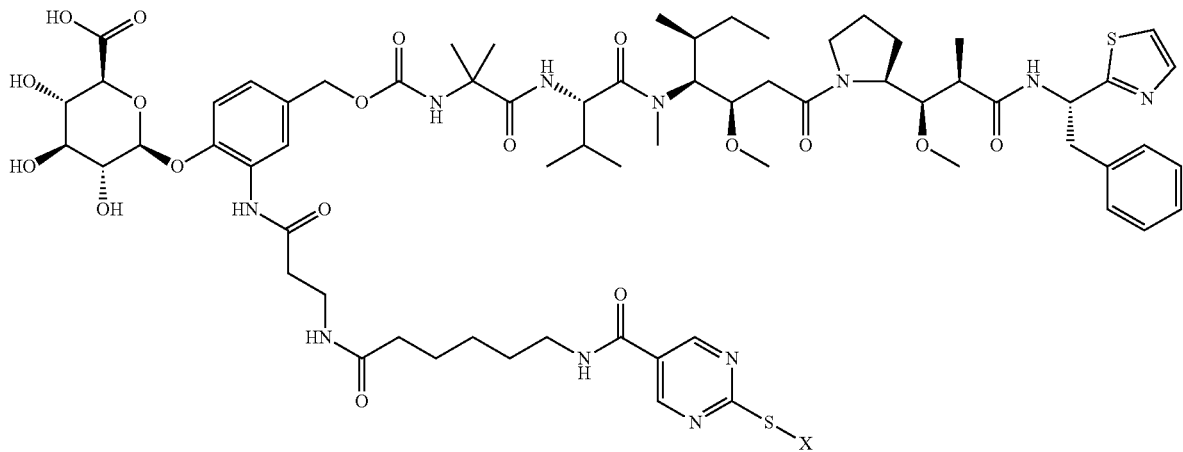

where X is H-(A114C)-,
or a pharmaceutically acceptable salt or solvate thereof.

In a further embodiment of the invention there is provided a pharmaceutical composition comprising a compound as described herein, or a pharmaceutically acceptable salt or solvate thereof, and pharmaceutically acceptable excipient.

In a further embodiment of the invention there is provided a method of treating cancer comprising administering to a patient in need thereof a therapeutically effective amount of a compound or pharmaceutical composition as described herein. In an aspect of this embodiment the cancer is bladder cancer, breast cancer, cervical cancer, colon cancer, endometrial cancer, kidney cancer, lung cancer, esophageal cancer, ovarian cancer, prostate cancer, pancreatic cancer, skin cancer, stomach (gastric) cancer, testicular cancer, leukemias and lymphomas.

DETAILED DESCRIPTION

The present invention is directed to heteroaryl sulphone linkers comprising an amide functionality, related linker-payloads which react with thiol functionalities in cysteine residues, and the resulting conjugates formed by these reactions. Such conjugates include antibody drug conjugates comprising a therapeutic and/or a cytotoxic component, and to methods for using the same to treat cancer and other pathological conditions. The invention also relates to methods of using such compounds and/or conjugates in vitro, in situ, and in vivo for the detection, diagnosis, or treatment of mammalian cells, or associated pathological conditions.

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the V.sub.H and V.sub.L domains of an antibody, wherein these domains are present in a single polypeptide chain. Typically, the Fv polypeptide further comprises a polypeptide linker between the V.sub.H and V.sub.L domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms). When the number of carbon atoms is not indicated, the alkyl group has from 1 to 8 carbon atoms, preferably from 1 to 6 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tent-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene —$CH_2CH_2$—), 1,3-propylene (—$CH_2CH_2CH_2$—), 1,4-butylene (—$CH_2CH_2CH_2CH_2$—), and the like. A "$C_1$-$C_{10}$" straight chain alkylene is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene. In certain embodiments of the invention, alkylenes have from 1 to 9, from 1 to 8, from 1 to 7, and from 1 to 6 carbons.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si, S and/or P, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

"Halo" or "halogen" refers to fluoro, chloro, bromo and iodo.

"Halo($C_{1-6}$-alkyl)" refers to $C_{1-6}$-alkyl groups substituted with 1 to 3 or 1 to 2 halo groups, wherein $C_{1-6}$-alkyl and halo are as defined herein. The term includes, for example, $CF_3$.

Unless otherwise indicated, the term "heteroalkylene" by itself or as part of another substituent means a divalent group derived from heteroalkyl (as discussed above). For heteroalkylene groups, heteroatoms can also occupy either or both of the chain termini.

Unless otherwise indicated, "aryl," by itself or an part of another term, means a substituted or unsubstituted monovalent aromatic hydrocarbon radical of 6 to 20 carbon atoms, preferably from 6 to 14 carbon atoms, derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted aromatic group (e.g., an aryl group) can be substituted with one or more, preferably 1 to 5, of the following groups: $C_1$-$C_8$ alkyl, —O—($C_1$-$C_8$ alkyl), —C(O)R', —OC(O)R', —C(O)OR', —C(O)$NH_2$, —C(O)NHR', —C(O)N(R')$_2$, —NHC(O)R', —S(O)$_2$R', —S(O)R', —OH, halogen, —$N_3$, —$NH_2$, —NH(R'), —N(R')$_2$ and —CN; wherein each R' is independently selected from —H, $C_1$-$C_8$ alkyl, $C_1$-$C_8$ heteroalkyl and aryl, preferably unsubstituted aryl. In some embodiments, a substituted aromatic group can further include one or more of: —NHC(=NH)$NH_2$, —NHCON$H_2$, —S(=O)$_2$R' and —SR'.

The term "heteroaryl", also called "Het" herein (sometimes depicted within a circle) as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted. Typical substituents include, but are not limited to, —X, —R, —O—, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3^{2-}$, PO$_3$H$_2$, -AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, C$_1$-C$_{20}$ heteroalkyl, C$_6$-C$_{20}$ aryl, C$_3$-C$_8$ heterocyclyl, C$_3$-C$_{20}$ carbocyclyl, a protecting group or a prodrug moiety, where each X is independently a halogen: —F, —Cl, —Br, or —I; and each R is independently —H or C$_1$-C$_6$ alkyl.

The terms "arylene", "heteroarylene" refer to divalent versions of "aryl" and "heteroaryl" respectively, and other terms incorporating "aryl" and "heteroaryl".

"Hydroxy" refers to the group —OH.

"Substituted alkyl" means an alkyl in which one or more hydrogen atoms are each independently replaced with a substituent. Typical substituents include, but are not limited to, —X, —R, —O—, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3^{2-}$, PO$_3$H$_2$, -AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, C$_1$-C$_{20}$ heteroalkyl, C$_6$-C$_{20}$ aryl, C$_3$-C$_8$ heterocyclyl, a protecting group or a prodrug moiety, where each X is independently a halogen: —F, —Cl, —Br, or —I; and each R is independently —H or C$_1$-C$_6$ alkyl. A substituted alkyl substituted with a halogen is sometimes refered to herein as a haloalkyl. Aryl, alkylene, heteroalkylene and other groups containing or not containing an alkyl or alkylene moiety as described herein may also be similarly substituted.

Unless otherwise indicated, "aralkyl" by itself or part of another term, means an alkyl group, as defined above, substituted with an aryl group, as defined above.

Unless otherwise indicated, "heteroatom" refers to oxygen, nitrogen, sulfur, or phosphorous. Each heteroatom in a structure may be the same or different.

Unless otherwise indicated, "C$_3$-C$_8$heterocyclyl" by itself or as part of another term, refers to a monovalent or divalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. Similarly, unless otherwise indicated, "C$_3$-C$_{10}$heterocyclyl" by itself or as part of another term, refers to a monovalent or divalent substituted or unsubstituted aromatic or non-aromatic monocyclic or bicyclic ring system having from 3 to 10 carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Heterocyclyl groups with more than 10 carbons, for instance rings or ring systems with 11, 12, 13, 14, 15, 16, 17, 18, 19 or 20 carbons, are also possible and are encompassed, along with C$_3$-C$_{10}$heterocyclyls, when the term "heterocyclyl" is employed without reference to a specific number of carbons. Similarly, heterocyclyl groups with less than 3 carbons, for instance rings with 1 or 2, are possible and are encompassed when the term "heterocyclyl" is employed without reference to a specific number of carbons. The term "heterocycloalkyl" refers to non-aromatic heterocyclyl rings or ring systems where all carbon atoms are saturated (i.e., bonded to a hydrogen or another substituent as noted below, with no double or triple bonds). In certain embodiments heterocycloalkyl groups typically have 3 to 5 members and 1 to 2 heteroatoms. In certain embodiments heterocycloalkyl can be epoxy.

Unless otherwise noted, the heterocyclyl is attached to its pendant group at any heteroatom or carbon atom that results in a stable structure. Representative examples of a C$_3$-C$_8$ heterocyclyl include, but are not limited to, tetrahyrofuranyl, oxetanyl, pyranyl, pyrrolidinyl, piperidinyl, benzofuranyl, benzothiophene, indolyl, benzopyrazolyl, pyrrolyl, thiophenyl (thiopene), furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C$_3$-C$_8$ heterocyclyl, or a C$_3$-C$_{10}$ heterocyclyl, can be substituted with up to seven groups including, but not limited to, C$_1$-C$_8$ alkyl, C$_1$-C$_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(=O)$_2$R', —S(O)R', halogen, —N$_3$, —NH$_2$, —NH(R'), —N(R')$_2$ and —CN; wherein each R' is independently selected from —H, C$_1$-C$_8$ alkyl, C$_1$-C$_8$ heteroalkyl and aryl. In some embodiments, a substituted heterocyclyl can also include one or more of: —NHC(=NH)NH$_2$, —NHCONH$_2$, —S(=O)$_2$R' and —SR'.

Unless otherwise indicated, "C$_3$-C$_{20}$ carbocyclyl" by itself or as part of another term, is a 3-, 4-, 5-, 6-, 7-, 8-, 9-, 10-, 11-, 12-, 13-, 14-, 15-, 16-, 17-, 18-, 19- or 20-membered monovalent, substituted or unsubstituted, saturated or unsaturated non-aromatic monocyclic or bicyclic carbocyclic ring derived by the removal of one hydrogen atom from a ring atom of a parent ring system. Preferably, the C$_3$-C$_{20}$ carbocyclyl includes from 3-14, or from 3-6, carbons. Representative C$_3$-C$_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.) pentane, and bicyclo(2.2.2.)octane. A C$_3$-C$_8$ carbocyclyl group can be unsubstituted or substituted with up to seven groups including, but not limited to, C$_1$-C$_8$ alkyl, C$_1$-C$_8$ heteroalkyl, —OR', aryl, —C(O)R', —OC(O)R', —C(O) OR', —C(O)NH$_2$, —C(O)NHR', —C(O)N(R')$_2$, —NHC(O) R', —S(=O)$_2$R', —S(=O)R', —OH, -halogen, —N$_3$, —NH$_2$, —NH(R'), —N(R')$_2$ and —CN; where each R' is independently selected from —H, C$_1$-C$_8$ alkyl, C$_1$-C$_8$ heteroalkyl and aryl. "C$_3$-C$_8$ carbocyclo" is the corresponding divalent moiety.

Unless otherwise indicated, "heteroaralkyl" by itself or part of another term, means an alkyl group, as defined above, substituted with an aromatic heterocyclyl group, as defined above.

Unless otherwise indicated, "C$_3$-C$_8$ carbocyclyl" by itself or as part of another term, is a 3-, 4-, 5-, 6-, 7- or 8-membered monovalent or divalent, substituted or unsubstituted, saturated or unsaturated non-aromatic monocyclic or bicyclic carbocyclic ring derived by the removal of one hydrogen atom or two hydrogen atoms from a ring atom of a parent ring system. Similarly, unless otherwise indicated, "$C_3$-$C_{10}$ carbocyclyl" by itself or as part of another term, is a 3-, 4-, 5-, 6-, 7-, 8-, 9- or 10-membered monovalent or divalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(111)pentane, and bicyclo(222)octane. A $C_3$-$C_8$ carbocyclyl group, or a $C_3$-$C_{10}$ carbocyclyl group, can be unsubstituted or substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(=O)$_2$R', —S(=O)R', —OH, -halogen, —N$_3$, —NH$_2$, —NH(R'), —N(R')$_2$ and —CN; where each R' is independently selected from —H, $C_1$-$C_8$ alkyl, $C_1$-$C_8$ heteroalkyl and aryl. Carbocyclyl groups with more than 10 carbons, for instance ring systems with 11, 12, 13, 14, 15, 16, 17, 18, 19 or 20 carbons, are also possible and are encompassed, along with $C_3$-$C_{10}$ carbocyclyls, when the term "carbocyclyl" is employed without reference to a specific number of carbons. The term "cycloalkyl" refers to carbocyclyl rings or ring systems where all carbon atoms are saturated (i.e., bonded to a hydrogen or another substituent as noted below, with no double or triple bonds).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADCs with a distribution of one or more drugs moieties per antibody. The average number of drugs per antibody may be calculated from the mixture by, for example, dual ELISA antibody assay, specific for antibody and specific for the drug. Individual ADCs may be identified in the mixture by mass spectroscopy, and separated by HPLC, e.g., hydrophobic interaction chromatography.

Below is a list of abbreviations and definitions that may not otherwise be defined or described in this application: DMSO (refers to dimethyl sulfoxide), HRMS (refers to high resolution mass spectrometry), DAD (refers to diode array detection), TFA (refers to 2,2,2-trifluoroacetic acid or trifluoroacetic acid), TFF (refers to tangential flow filtration), EtOH (refers to ethanol), MW (refers to molecular weight), HPLC (refers to high performance liquid chromatography), prep HPLC (refers to preparative high performance liquid chromatography), etc. (refers to and so forth), trityl (refers 1,1',1''-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

As used herein, "H/C" or "H-(C)" refers to trastuzumab (sold under the trade name HERCEPTIN®) or a substantially similar monoclonal antibody that interferes with the HER2/neu receptor, bound through one of its cysteine residues (to a linker or a compound of the invention).

As used herein, "CD33-11A1-v1417-(C)" refers to an anti-CD33 antibody, which is a monoclonal antibody that binds to CD33, bound through one of its cysteine residues (to a linker or a compound of the invention).

As used throughout this application, the amino acid residue numbering (for example: Alanine at position 114) is based on EU index of Kabat method.

As used herein, "H-(A114C)" refers to engineered trastuzumab which is a monoclonal antibody that interferes with the HER2/neu receptor, bound through one of its engineered cysteine which was substituted for alanine at position 114 of the heavy chain (to a linker or a compound of the invention).

As used herein, "H-(kK183C)" refers to engineered trastuzumab which is a monoclonal antibody that interferes with the HER2/neu receptor, bound through its engineered cysteine which was substituted at lysine at position 183 of the light (kappa) chain (to a linker or a compound of the invention).

As used herein, "H-(E380C)" refers to engineered trastuzumab which is a monoclonal antibody that interferes with the HER2/neu receptor, bound through its engineered cysteine which was substituted at glutamate at position 380 of the heavy chain (to a linker or a compound of the invention).

As used herein, "CD33-11A1-v1417-(K290C)-(K334C)" refers to an engineered anti-CD33 antibody, which is a monoclonal antibody that binds to CD33, bound through its engineered cysteines which were substituted at lysine at position 290 and at lysine at position 334 of the heavy chain (to a linker or a compound of the invention).

As used herein, "CD33-11A1-v1417-(K334C)-(K392C)" refers to engineered anti-CD33 antibody, which is a monoclonal antibody that binds to CD33, bound through its engineered cysteines which were substituted at lysine at position 334 and at lysine at position 392 of the heavy chain (to a linker or a compound of the invention).

Generally, as used herein, "H-((AA1)###(AA2))" (where (AA1) and (AA2) are a first and a second amino acid) refers to engineered trastuzumab which is a monoclonal antibody that interferes with the HER2/neu receptor, bound through its engineered (AA2) which was substituted at (AA1) at position ### of the heavy chain to compound of the invention, where ### represents the position of the relevant amino acid(s). Similar notation referencing "k" or kappa" would indicate a substitution on the kappa form of the light chain.

Similarly, as used herein, "H-((AA1)###(AA2)-((AA3)####(AA4))" (where (AA1), (AA2), (AA3) and (AA4) are first, second, third and fourth amino acids) refers to engineered trastuzumab which is a monoclonal antibody that interferes with the HER2/neu receptor, bound through its engineered (AA2) which was substituted at (AA1) at position ### of the heavy chain to compound of the invention, where ### represents the position of the relevant amino acid(s), and also bound through its engineered (AA4) which was substituted at (AA3) at position #### of the heavy chain to compound of the invention, where #### represents the position of the relevant amino acid(s). Similar notation referencing "k" or kappa" would indicate a substitution on the kappa form of the light chain.

Generally, as used herein, "CD33-11A1-v1417-((AA1)###(AA2))" (where (AA1) and (AA2) are a first and a second amino acid) refers to engineered anti-CD33 antibody, which is a monoclonal antibody that binds to CD33, bound through its engineered (AA2) which was substituted at (AA1) at position ### of heavy chain to compound of the invention, where ### represents the position of the relevant amino acid(s). Similar notation referencing "k" or kappa" would indicate a substitution on the kappa form of the light chain.

Similarly, as used herein, "CD33-11A1-v1417-(AA1)###(AA2)+(AA3)####(AA4)/(AA2)###+(AA4)####" (where (AA1), (AA2), (AA3) and (AA4) are first, second, third and fourth amino acids) refers to engineered trastuzumab which is a monoclonal antibody that interferes with the HER2/neu receptor, bound through its engineered (AA2) which was substituted at (AA1) at position ### of heavy chain to compound of the invention, where ### represents the position of the relevant amino acid(s), and also bound through its engineered (AA4) which was substituted at (AA3) at position #### of heavy chain to compound of the invention, where #### represents the position of the relevant amino acid(s). Similar notation referencing "k" or kappa" would indicate a substitution on the kappa form of the light chain.

As used herein, "-PABC-" or "PABC" refers to the structure:

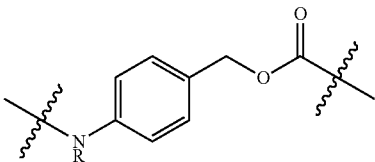

or variants thereof.

As used herein, "-PABA-" or "PABA" refers to the structure:

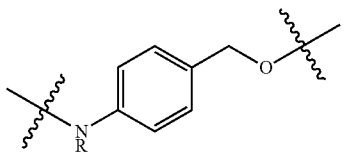

or variants thereof.

The Antibody Unit (Ab or AB)

As noted above, the term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody, conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

In another aspect, the present invention relates to an antibody drug conjugate compound of formulae II wherein P is an antibody selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, anti-HLA-DR antibodies including a humanized anti-HLA-DR antibody for the treatment of non-Hodgkin's lymphoma, 131I Lym-1, anti-HLA-Dr10 antibodies including a murine anti-HLA-Dr10 antibody for the treatment of non-Hodgkin's lymphoma, anti-CD33 antibodies, anti-CD22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In yet another aspect, the antibody has native or engineered cysteine residues that can react with the compounds of this invention and thus form a thio-ether bond consistiong of the sulfur atom of the antibody unit and the carbon atom bearing the $R^2SO_2$ groupin Formula (I). For instance, see WO2013/093809 ("Engineered Antibody Constant Regions for Site-Specific Conjugation and Methods and Uses Therefor"); and WO2014/068443 ("Spliceostatin Analogs").

In addition, a free sulfur or sulfhydryl group may be introduced as described in the following paragraphs, and by other well-known methods.

In another embodiment, the antibody has lysine residues that can react with activated esters (such esters include, but are not limited to, N-hydroxysuccinimde, pentafluorophenyl, and p-nitrophenyl esters) and thus form an amide bond consisting of the nitrogen atom of the antibody unit and a carbonyl. For instance, in an aspect of this embodiment, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit has one or more carbohydrate groups that can be chemically modified to have one or more sulfhydryl groups. For instance, in an aspect of this embodiment, the antibody unit has one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, a compound containing a hydrazine or a hydroxylamine moiety, and that also contains one or more free or masked sulfhydryl groups. Other protocols for the modification of proteins for the attachment or association of drugs are described in Coligan et al., Current Protocols in Protein Science, vol. 2, John Wiley & Sons (2002) (incorporated herein by reference).

In another embodiment, the antibody unit has one or more glutamine residues that can react with primary amines under conditions enzymatically catalyzed by transglutaminase and thus form an amide bond consisting of the sidechain carbonyl group of a glutamine residue on the antibody unit and an amine. In an aspect of this embodiment, glutamine residues may be endogenous glutamines, glutamine-containing tags introduced by engineering, and/or endogenous glutamines made reactive by antibody engineering or an engineered transglutaminase (e.g., with altered substrate specifity), as described in WO2012/059882 ("Engineered Polypeptide Conjugates and Methods for Making Thereof Using Transglutaminase"), WO2015/015448 ("Engineered Polypeptide Conjugates Using Transglutaminase"), and WO2015/162563 ("Antibody-Drug Conjugates with High Drug Loading"), each of which are incorporated herein by reference in their entirety. In another aspect of this embodiment, the antibody unit has one or more glutamine residues that can be chemically modified to introduce one or more sulfhydryl groups. Such modification can be performed under conditions catalyzed by transglutaminase wherein an amide bond is formed between the sidechain carbonyl of a glutamine residue and a primary amine that also contains one or more free or masked sulfhydryl groups.

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-α and TGF-β, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, OVAREX which is a murine antibody for the treatment of ovarian cancer; PANOREX (Glaxo Wellcome, NC) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; and CEACIDE (Immunomedics, NJ) which is a humanized anti-CEA antibody for the treatment of colorectal cancer.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The Linker Unit

A linker is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells. In an ADC the linker serves to attach the payload to the antibody.

The conjugates of the invention contain a linker that may optionally incorporate a cleavage element that, once cleaved, either chemically or enzymatically, ultimately leads to the release of the drug or of an active agent that may be a derivative of the drug. Examples of cleavage elements include, but are not limited to, chemically cleaved acyl hydrazones, such as those described in U.S. Pat. No. 5,773, 001, enzymatically cleaved dipeptide or dipeptide-p-amino-benzylcarbamate sequences, such as those described in U.S. Pat. No. 6,214,345 B1, enzymatically cleaved glurcuronide or glycoside moieties, such as those described in U.S. Pat. Nos. 8,039,273_B2 and 8,568,728 B2, and the like. In certain embodiments of the invention additional immolative spacer elements, such as p-aminobenzylcarbamate moieties, substituted or unsubstituted N,N-diaminoethyl or N,N-diaminopropyl moieties, may be incorporated into the linker unit.

In certain embodiments of the invention a linker may be "non-cleavable", in which case there are no chemically or enzymatically sensitive bonds within the linker. In these cases, the drug or active agent is envisioned to be released via enzymatic catabolism of the antibody itself, thereby releasing the drug with the linker and one or more amino acids derived from the antibody intact.

In certain embodiements of the invention the linker unit may first be attached to the drug, and then the drug-linker element is, in a separate transformation, attached to the antibody or antibody fragment.

In other embodiments of the invention the linker unit may first be attached to the antibody or antibody fragment, and then the drug or drug derivative is, in a separate transformation, attached to the antibody-linker or antibody fragment-linker.

Synthesis of Compounds and Antibody Drug Conjugates Thereof

The compounds and conjugates of the invention include those which can be made using the synthetic procedures outlined below in the Exemplification. As described in more detail below, the compounds and conjugates of the invention can be prepared using a section of a linker unit having a reactive site. In one aspect, a second section of the linker unit is introduced which has a second reactive site that is selectively reactive toward the thiol group of cysteine residues (or the selenol group of a selenocysteine residue). As described in more detail below, the conjugates can be prepared using a section of the linker having a reactive site for binding to a drug, probe, or imaging agent and introducing another section of the linker unit having a reactive site for an antibody. In one aspect, a linker unit has a reactive site which has an electrophilic group that is selectively reactive with a thiol nucleophilic group present on an antibody unit, such as an antibody. The electrophilic group provides a convenient site for antibody attachment. The heteroatom of the nucleophilic group of an antibody is reactive to an electrophilic group on a linker unit and forms a covalent bond to a linker unit.

The compounds and conjugates of the invention also include those which can be made using step wise preparation.

Certain compounds of Formula I of this invention contain a thiol-reactive electrophilic group that is capable of undergoing a nucleophilic aromatic substitution reaction ($S_NAr$), known to those commonly skilled in the art, wherein the thiol moiety present on a polypeptide or antibody unit reacts with the electrophilic group with displacement of the $R^2SO_2$ group in Formula I. This reaction provides a new covalent bond between the sulfur atom on the polypeptide or antibody unit and the aromatic carbon atom of the electrophilic group that formerly bore the $R^2SO_2$ group in Formula I. In one aspect of this invention, the thiol group of a polypeptide or antibody unit may be naturally occurring, in free or capped form, or be present in a naturally-occurring sulfide bond, and may require prior treatment with reagents, such as dithiothreitol (DTT), cysteine, tris-(2-carboxyethyl)phosphine (TCEP), and the like, to effect the uncapping of that thiol group with liberation of the reactive thiol. In another aspect of the invention, the thiol group of a polypeptide or antibody unit may be introduced by engineering and may be present in free or capped form, and may require prior treatment with reagents, such as dithiothreitol (DTT), cysteine, tris-(2-carboxyethyl)phosphine (TCEP), and the like, to effect the uncapping of that thiol group with liberation of the reactive thiol. In another aspect of the invention, the thiol group of a polypeptide or antibody unit may be introduced by chemical or enzymatic reaction of the polypeptide or antibody unit with compounds that contain a reactive moiety for attachment to the polypeptide or antibody unit that also contain one or more free, capped or protected thiol groups that may require prior treatment with reagents, such as dithiothreitol (DTT), cysteine, tris-(2-carboxyethyl)phosphine (TCEP), and the like, to effect the uncapping of that thiol group with liberation of the reactive thiol.

In aspects of this invention, the reaction of the thiol group present on the polypeptide or antibody unit is capable of undergoing a selective reaction with the thiol reactive electrophilic group in Formula I in the presence of other potentially nucleophilic groups, including, for instance, the amine groups present on lysine side chains, the amidine groups present on arginine side chains, the imidazole groups present on histidine side chains, the alcohol groups present on serine or threonine side chains, or the phenol groups present on tyrosine side chains.

Compositions and Methods of Administration

In other embodiments, another aspect of the invention relates to pharmaceutical compositions including an effective amount of a compound of the invention and/or antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or antibody drug conjugate thereof to be bioavailable upon administration of the composition to a patient. Compositions can take the form of one or more dosage units, where for example, a tablet can be a single dosage unit, and a container of a compound of the invention and/or antibody drug conjugate thereof in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound of the invention and/or antibody drug conjugate thereof, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody drug conjugate thereof that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound of the invention and/or antibody drug conjugate thereof such that a suitable dosage will be obtained. Typically, this amount is at least about 0.01% of a compound of the invention and/or antibody drug conjugate thereof by weight of the composition. In an exemplary embodiment, pharmaceutical compositions are prepared so that a parenteral dosage unit contains from about 0.01% to about 2% by weight of the amount of a compound of the invention and/or antibody drug conjugate thereof.

For intravenous administration, the composition can comprise from about 0.01 to about 100 mg of a compound of the invention and/or antibody drug conjugate thereof per kg of the patient's body weight. In one aspect, the composition can include from about 1 to about 100 mg of a compound of the invention and/or antibody drug conjugate thereof per kg of the patient's body weight. In another aspect, the amount administered will be in the range from about 0.1 to about 25 mg/kg of body weight of a compound of the invention and/or antibody drug conjugate thereof.

Generally, the dosage of a compound of the invention and/or antibody drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

A compound of the invention and/or antibody drug conjugate thereof can be administered by any convenient route, for example by infusion or bolus injection. Administration can be systemic or local. Various delivery systems are known, e.g., encapsulation in liposomes, mieroparticles, microcapsules, capsules, etc., and can be used to administer a compound of the invention and/or antibody drug conjugate thereof. In certain embodiments, more than one ompound of the invention and/or antibody drug conjugate thereof is administered to a patient.

In specific embodiments, it can be desirable to administer one or more compounds of the invention and/or antibody drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody drug conjugate thereof can be delivered in a controlled release system, such as but not limited to, a pump or various polymeric materials can be used. In yet another embodiment, a controlled-release system can be placed in proximity of the target of the compound of the invention and/or antibody drug conjugate thereof, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a compound or antibody drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the compound of the invention and/or antibody drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody drug conjugate thereof is to be administered by infusion, it can be dispensed, for example, with an infusion bottle containing sterile pharmaceutical grade water or saline. Where the compound of the invention and/or antibody drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

Therapeutics Uses of Compounds and Antibody Drug Conjugates Thereof

Another aspect of the invention relates to a method of using the compounds of the invention and antibody drug conjugates thereof for treating cancer.

The compounds of the invention and/or antibody drug conjugates thereof are useful for inhibiting the multiplication of a tumor cell or cancer cell, causing apoptosis in a tumor or cancer cell, or for treating cancer in a patient. The compounds of the invention and/or antibody drug conjugates thereof can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are enzymatically or hydrolytically cleaved by one or more tumor cell or cancer cell-associated proteases, resulting in release of a compound of the invention from the conjugate. The released compound of the invention is then free to migrate within the cell and induce cytotoxic or cytostatic activities. The conjugate also can be cleaved by an intracellular protease to release a compound of the invention. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

Particular types of cancers that can be treated with a compound of the invention and/or antibody drug conjugate thereof, include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

Multi-Modality Therapy for Cancer. Cancers, including, but not limited to, a tumor, metastasis, or other disease or disorder characterized by uncontrolled cell growth, can be treated or inhibited by administration of a compound of the invention and/or antibody drug conjugate thereof.

In other embodiments, methods for treating cancer are provided, including administering to a patient in need thereof an effective amount of a compound of the invention and/or antibody drug conjugate thereof and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention and/or antibody drug conjugate thereof can be administered to a patient that has also undergone surgery as treatment for the cancer.

In some embodiments, the patient also receives an additional treatment, such as radiation therapy. In a specific embodiment, the compound of the invention and/or antibody drug conjugate thereof is administered concurrently with the chemotherapeutic agent or with radiation therapy. In another specific embodiment, the chemotherapeutic agent or radiation therapy is administered prior or subsequent to administration of a compound of the invention and/or antibody drug conjugate thereof.

A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention and/or antibody drug conjugate thereof are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention and/or antibody drug conjugates thereof can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of a compound of the invention and/or antibody drug conjugate thereof with or without accompanying high dose radiation therapy, and the stem cell graft is infused back into the animal. Supportive care is then provided while bone marrow function is restored and the patient recovers.

The invention is further described in the following examples, which are in not intended to limit the scope of the invention.

EXAMPLES

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction Protocol (length of reaction and temperature) may vary. In general, reactions were followed by thin layer chromatography or LCMS, and subjected to work-up when appropriate. Purifications may vary between experiments: in general, solvents and the solvent ratios used for eluents/gradients were chosen to provide appropriate retention times.

HRMS were performed on an Agilent 6220 TOF LC/MS.

HPLC, LCMS, and SEC Conditions Used for Analyses

Protocol A: Column: Waters Acquity UPLC BEH, 2.1 mm×50 mm, C18, 1.7 μm; Mobile phase A: : 0.1% formic acid in water (v/v); Mobile phase B: 0.1% formic acid in acetonitrile (v/v); Gradient: 5% B over 0.1 minute, 5% to 95% B over 0.7 minutes, 95% B over 0.1 minutes; Flow rate: 1.25 mL/minute. Temperature: 60° C.; Detection: 200-450 nm; MS (+) range 100-1200 daltons; Injection volume: 5 μL; Instrument: Waters Acquity.

Protocol B: Column: Phenomenex Luna C18 (2), 150×3.0 mm, 5 μm; Mobile phase A: 0.02% trifluoroacetic acid in water (v/v); Mobile phase B: 0.02% trifluoroacetic acid in acetonitrile (v/v); Gradient: 0% to 100% B over 8.5 minutes; Flow rate: 1.5 mL/minute. Temperature: not controlled; Detection: DAD 210 nm; Injection volume: 10 μL; Instrument: Agilent 1100 HPLC.

Protocol C: Column: Phenomenex Luna C18 (2), 150×3.0 mm, 5 μm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B for 1 minute; Flow rate: 0.75 mL/minute. Temperature: 25° C.; Detection: DAD 215 nm, 254 nm; MS (+) range 150-2000 daltons; Injection volume: 10 μL; Instrument: Agilent 1200 LCMS.

Protocol D: Column: Waters Acquity UPLC BEH, 2.1 mm×50 mm, C18, 1.7 μm; Mobile phase A: : 0.1% formic acid in water (v/v); Mobile phase B: 0.1% formic acid in acetonitrile (v/v); Gradient: 5% B over 0.1 minutes, 5% to 95% B over 0.7 minutes, 95% B over 0.1 minutes; Flow rate: 1.25 mL/minute. Temperature: 60° C.; Detection: 200-450 nm; MS (+) range 100-1200 daltons; Injection volume: 5 μL; Instrument: Waters Acquity.

Protocol E: Column: Waters Acquity HSS T3, C18, 2.1× 50 mm, 1.7 μm; Mobile phase A: 0.1% formic acid in water (v/v); Mobile phase B: 0.1% formic acid in acetonitrile (v/v); Gradient: 5% B over 0.1 minutes, 5% to 95% B over 2.5 minutes, 95% B 0.35 minute; Flow rate: 1.25 mL/minute. Temperature: 60° C.; Detection: 200-450 nm; MS (+) range 100-2000 m/z; Injection volume: 5 μL; Instrument: Waters Acquity UPLC.

Protocol F: Column: YMC-pack ODS-A, 150 mm×4.6 mm, 5 μm; Mobile phase A: 0.1% trifluoroacetic acid in water (v/v); Mobile phase B: 0.1% trifluoroacetic acid in acetonitrile (v/v); Gradient: 0% to 95% B over 10 minutes, 95% B over 5 minutes; Flow rate: 1.0 mL/minute. Detection: 220 nm.

Protocol G: Column: YMC-pack ODS-A, 150 mm×4.6 mm, 5 μm; Mobile phase A: 0.1% trifluoroacetic acid in water (v/v); Mobile phase B: 0.1% trifluoroacetic acid in acetonitrile (v/v); Gradient: 65% to 100% B over 10 minutes, 100% B over 5 minutes; Flow rate: 1.0 mL/minute. Detection: 220 nm.

Protocol H: Column: Phenomenex Luna C18 (2), 150×3.0 mm, 5 μm; Mobile phase A: 0.02% trifluoroacetic acid in water (v/v); Mobile phase B: 0.02% trifluoroacetic acid in acetonitrile (v/v); Gradient: 0% to 100% B over 20 minutes; Flow rate: 1.5 mL/minute. Temperature: not controlled; Detection: DAD 210 nm; Injection volume: 10 μL; Instrument: Agilent 1100 HPLC.

Protocol I: Column: Waters Acquity HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minutes, 5% to 95% B over 5 minutes, 95% B 0.35 minute; Flow rate: 1.25 mL/minute. Temperature: 60° C.; Detection: 200-450 nm; MS (+) range 100-2000 m/z; Injection volume: 5 μL; Instrument: Waters Acquity UPLC.

Protocol J: Column: Ultimate XB-C18, 50 mm×3.0 mm, 3 μm; Mobile phase A: 0.1% trifluoroacetic acid in water (v/v); Mobile phase B: 0.1% A trifluoroacetic acid in acetonitrile (v/v); Gradient: 1% to 5% B over 1 minute, 5% to 100% B over 5 minutes, 100% B over 2 minutes then 1% B over 2 minutes; Flow rate: 1.2 mL/minute. Detection: 220 nm.

Protocol K: Column: Ultimate XB-C18, 30 mm×5.0 mm, 3 μm; Mobile phase A: 0.1% trifluoroacetic acid in water (v/v); Mobile phase B: 0.1% trifluoroacetic acid in acetonitrile (v/v); Gradient: 1% to 5% B over 1 minute, 5% to 100% B over 5 minutes, 100% B over 2 minutes then 1% B over 2 minutes; Flow rate: 1.2 mL/minute. Detection: 220 nm.

Protocol L: Column: Agilent Poroshell 300SB-C8, 75×2.1 mm, 2.6 μm; Mobile phase A: 0.1% formic acid in water (v/v); Mobile phase B: 0.1% formic acid in acetonitrile (v/v); Gradient: Initial Conditions: 20% B to 45% B over 4 minutes; Flow rate: 1.0 mL/minute. Temperature: 60° C.; Detection: 220 nm; MS (+) range 400-2000Da; Injection volume: 10 μL; Instrument: Agilent 1100 LC, Waters MicromassZQ MS. Deconvolution was performed using MaxEnt1.

Protocol M: Column: TSK-gel G3000SWxl, 300×7.8 mm 10 μm; Mobile phase: Phosphate buffer saline (PBS, 1×, pH 7.4) with 2% acetonitrile; Isochratic; Flow rate: 1 mL/minute. Temperature: room temperature; Injection Volume: 5 μL; Instrument: Agilent 1100 HPLC.

Protocol N: Column: GE Superdex 200 (5/150 GL); Mobile phase: Phosphate buffered saline (PBS, 1×, pH 7.4) with 2% acetonitrile; Isocratic; Flow rate: 0.25 mL/minute. Temperature: room temperature; Injection Volume: 10 μL; Instrument: Agilent 1100 HPLC.

Protocol O: Column: Waters Acquity HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minutes, 5% to 95% B over 0.1-1.0 minutes, 95% B for 1.0-1.1 minute; Flow rate: 1.25 mL/minute. Temperature: 60° C.; Detection: 200-450 nm; MS (+) range 100-2000 m/z; Injection volume: 5 μL; Instrument: Waters Acquity UPLC and Waters Acquity SQ system.

Protocol P: Column: Waters Acquity HSS T3, C18, 2.1× 50 mm, 1.7 μm; Mobile phase A: 0.1% formic acid in water (v/v); Mobile phase B: 0.1% formic acid in acetonitrile (v/v); Gradient: 5% B over 0.1 minutes, 5% to 95% B over 0.1-2.6 minutes, 95% B for 2.6-2.95 minutes; Flow rate: 1.25 mL/minute. Temperature: 60° C.; Detection: 200-450 nm; MS (+) range 100-2000 m/z; Injection volume: 5 μL; Instrument: Waters Acquity UPLC and Waters Acquity SQ system.

Protocol Q: Column: Waters Xbridge, C18, 2×50 mm, 5 μm; Mobile phase A: 10 mM $NH_4HCO_3$ in water; Mobile phase B: acetonitrile; Gradient: 1-5% B over 0.6 minutes, 5-100% B over 0.6-3.4 minutes; Flow rate: 0.8 mL/minute. Temperature: room temperature; Injection Volume: 10 μL; Instrument: Agilent 1200 HPLC.

HPLC conditions Used for Purification

Method A: Column: Phenomenex Luna C18, 100×30 mm, 10 μm; Mobile phase A: 0.02% trifluoroacetic acid in water (v/v); Mobile phase B: 0.02% trifluoroacetic acid in methanol (v/v); Gradient: 10% to 90% B over 20 minutes; Flow rate: 20 mL/minute. Temperature: not controlled; Detection: DAD 210 nm, 254 nm; Injection Volume: variable; Instrument: Gilson.

Method B: Column: Phenomenex Luna C18 (2), 150× 21.2 mm, 5 μm; Mobile phase A: 0.02% trifluoroacetic acid in water; Mobile phase B: 0.02% trifluoroacetic acid in acetonitrile; Gradient: 1% B over 1.5 minutes, 1% to 50% B over 8.5 minutes; Flow rate: 27 mL/minute; Detection: DAD 210-360 nm; MS (+) range 150-2000 daltons; Instrument: Waters FractionLynx.

Method C: Column: Phenomenex Luna C18, 100×30 mm, 10 μm; Mobile phase A: 0.02% trifluoroacetic acid in water (v/v); Mobile phase B: 0.02% trifluoroacetic acid in methanol (v/v); Gradient: 20% to 80% B over 20 minutes; Flow rate: 20 mL/minute. Temperature: not controlled; Detection: DAD 210 nm, 254 nm; Injection Volume: variable; Instrument: Gilson.

Method D: Column: Phenomenex Synergi Max-RP C12, 250×50 mm, 10 μm; Mobile phase A: 0.2% formic acid in water (v/v); Mobile phase B: acetonitrile (v/v); Gradient: 15% to 45% B over 30 minutes, 95% B over 5 minutes; Flow rate: 80 mL/minute. Temperature: not controlled; Detection: UV 210 nm, 254 nm; MS(+) range: 100-1000 daltons; Injection Volume: variable; Instrument: Shimadzu LC-20AP.

In some instances some minor alternations to elution conditions for LCMS and HPLC preparative purification conditions were made such as but not limited to a change in the gradient, flow rate, or modifier composition. When applicable, such alterations are denoted in the specific procedures listed herein.

General Procedures

General Procedure A: Fmoc Removal Using Diethylamine

To a solution of the Fmoc-containing compound in dichloromethane was added diethylamine to afford a ratio from 1:1 to 1:10 diethylamine:dichloromethane. Reaction progress was monitored by LCMS (or HPLC or TLC); the reaction was usually completed within three hours. Solvents were removed in vacuo, or in some cases concentrated under a flow of nitrogen, and the residue was purified by reverse phase chromatography.

General Procedure B: Amide Coupling with O-(7-azabenzotriazol-1-yl)-N,N,N',N'-tetramethyluronium hexafluorophosphate (HATU)

To a stirring solution of the amine (1.0 equiv) and acid (1.0-2.0 equiv) in N,N-dimethylformamide (DMF) or N,N-dimethylacetamide (DMA), HATU (1.0-2.0 equiv) was added followed by N,N-diisopropylethylamine (2.0-4.0 equiv). Reaction progress was monitored by LCMS (or HPLC or TLC); the reaction was usually completed within three hours. Solvents were removed in vacuo. The residue was purified by silica gel or reverse phase chromatography.

Note: all LCMS data are based on Protocol A (1.5 minute method) unless otherwise noted.

Preparation of 5-(methylsulfonyl)pyrazine-2-carboxylic acid (#1)

Scheme for Compound #1:

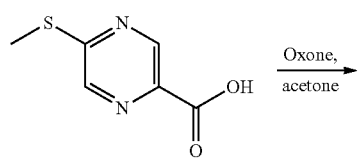

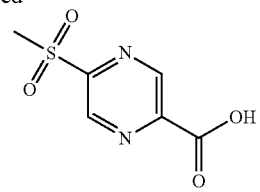

A mixture of the 5-methylsulfanyl-pyrazine-2-carboxylic acid (0.73 g, 4.3 mmol, 1 equiv) and Oxone (15.4 g, 22 mmol, ~6 equiv) in acetone (30 mL) was vigorously stirred at 45° C. for approx. 20 h. The cooled (room temperature) reaction mixture was filtered, the filter cake was washed with acetone (2×20 mL) and acetonitrile (10 mL), and the filtrate was concentrated under reduced pressure. The crude material was purified by reverse phase chromatography over a 100 g C18 column, using gradient elution of 0-30% acetonitrile in water containing 0.1% formic acid over 20 mintues to provide 5-(methylsulfonyl)pyrazine-2-carboxylic acid, #1 (0.25 g, 29%), as a white solid. LCMS (Protocol E): m/z 202.9 [M+H]$^+$, retention time=0.23 minutes; $^1$H NMR (400 MHz, DMSO): δ 9.35-9.32 (m, 2H), 3.40 (s, 3H).

Intermediate #2

Preparation of 2-(methylsulfonyl)benzo[d]thiazole-6-carboxylic acid (#2)

Scheme for Compound #2:

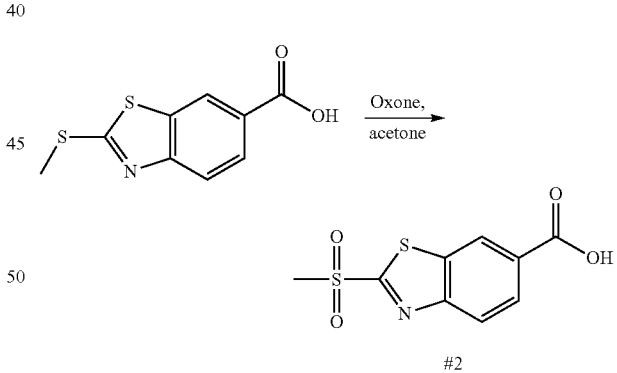

2-(Methylsulfonyl)benzo[d]thiazole-6-carboxylic acid (30 mg, 8%) was synthesized from 2-(methylsulfanyl)-1,3-benzothiazole-6-carboxylic acid (Compound 12 in WO 2013056070 A2) (0.33 g, 1.44 mmol), Oxone (7.0 g, 11 mmol), and acetone (10 mL) by following a procedure analogous to that of 5-(methylsulfonyl)pyrazine-2-carboxylic acid, #1, above. LCMS (Protocol E): m/z 257.9 [M+H]$^+$, retention time=0.85 minutes; $^1$H NMR (400 MHz, DMSO): δ 13.45 (br s, 1H), 9.02-9.00 (m, 1H), 8.37-8.22 (m, 1H), 8.24-8.21 (m, 1H), 3.62 (s, 3H).

Preparation of N,2-dimethyl-N-[6-({[5-(methyl-sulfonyl)pyrazin-2-yl]carbonyl}amino)hexanoyl]alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#6)
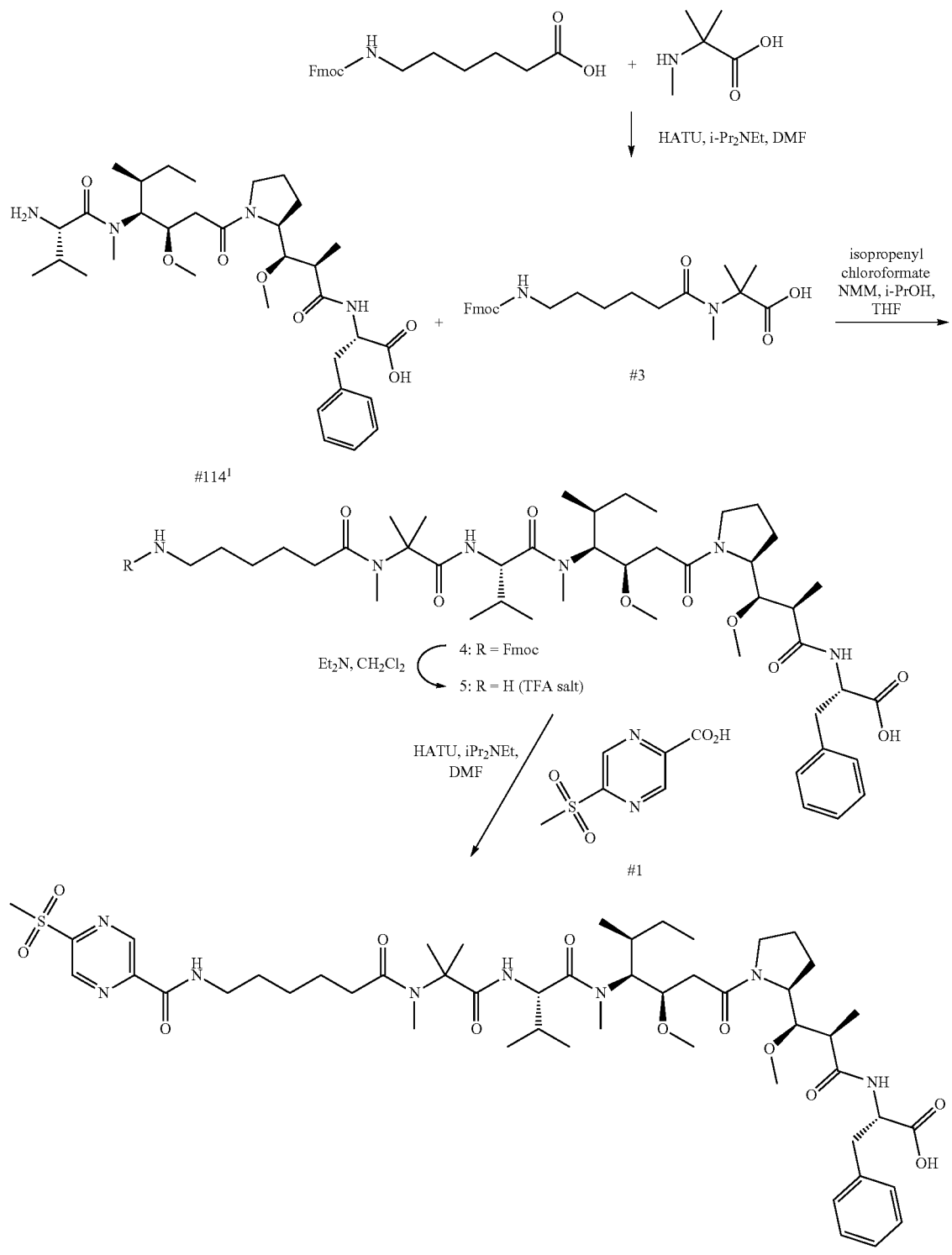

Step 1. Synthesis of N-(6-{[(9H-fluoren-9-yl-methoxy)carbonyl]amino}-N-methylhexanamido)-2-methylpropanoic acid (#3)

To a solution of 6-{[(9H-fluoren-9-ylmethoxy)carbonyl] amino}hexanoic acid (1 g, 3 mmol) in N,N-dimethylformamide (5 mL, 0.15 M) was added HATU (1.108 g, 2.8 mmol) followed by N,N-diisopropylethylamine (1 mL, 5 mmol). This reaction mixture was added dropwise to a solution of 2-methyl-2-(methylamino)propanoic acid (332 mg, 2.83 mmol) and N,N-diisopropylethylamine (1 mL, 5 mmol) in N,N-dimethylformamide (5 mL). The resulting brown solution was stirred at room temperature. After 90 min, LCMS analysis demonstrated that the reaction was complete. The reaction mixture was diluted with dichloromethane, washed with a 1N aqueous solution of hydrochloric acid (x3), the organic layer was dried over anhydrous sodium sulfate, concentrated to dryness, and the resulting residue was purified by silica gel chromatography (50%-100% ethyl acetate in heptane with 0.1% acetic acid). Pooled product-containing fractions were evaporated to give the title compound #3 (415 mg, 30%) as a pinkish gum. LCMS: m/z 453.20 [M+H]$^+$, retention time=0.89 minutes; $^1$H NMR (500 MHz, CHLOROFORM-d) δ ppm 7.76 (d, J=7.6 Hz, 2 H) 7.60 (d, J=7.3 Hz, 2 H) 7.39 (t, J=7.5 Hz, 2 H) 7.28-7.34 (m, 2 H) 4.33-4.45 (m, 2 H) 4.17-4.28 (m, 1 H) 3.12-3.22 (m, 2 H) 2.97 (s, 3 H) 2.30-2.39 (m, 2 H) 1.58-1.68 (m, 2 H) 1.47-1.56 (m, 2 H) 1.43 (s, 6 H) 1.31-1.39 (m, 2 H).

Step 2. Synthesis of N-(6-{[(9H-fluoren-9-yl-methoxy)carbonyl]amino}hexanoyl)-N,2-dimethyl-alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#4)

To a solution of #3 (194 mg, 0.429 mmol) in tetrahydrofuran (2 mL) in an iced water bath was added N-methyl morpholine (140 µL) followed by dropwise addition of isoproprenyl chloroformate (47.8 µL, 1.3 mmol). After 1 h, this reaction mixture was added dropwise to a solution of N-{(2R,3R)-3-methoxy-3-[(2S)-1-{(3R,4S,5S)-3-methoxy-5-methyl-4-[methyl(L-valyl)amino]heptanoyl}pyrrolidin-2-yl]-2-methylpropanoyl}-L-phenylalanine (Example #114 in US 2013/0129753 A1) (211 mg, 0.311 mmol) in isopropanol (1 mL) and tetrahydrofuran (1 mL). After 2 h, LCMS analysis demonstrated that the reaction was complete. The reaction mixture was concentrated under reduced pressure then the residue was purified by reverse phase chromatography according to a modified version of purification Method A (utilizing gradient elution of 20-100% acetonitrile in water containing 0.02% acetic acid over 20 minutes). Pooled product containing fractions were lyophilized to provide the title compound #4 (82 mg, 25%) as a white solid. LCMS: m/z 1053.6 [M+H]$^+$, retention time=2.10 minutes; HPLC (Protocol B): retention time=8.034 minutes.

Step 3. Synthesis of N-(6-aminohexanoyl)-N,2-dimethylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#5)

According to general procedure A above, from #4 (81 mg, 0.077 mmol), dichloromethane (1 mL, 0.08 M) and diethylamine (0.3 mL, 3 mmol) were synthesized #5 (59 mg) as an amorphous glass after purification by reverse phase chromatography according to a modified version of purification Method A (utilizing gradient elution of 20-70% acetonitrile in water containing 0.02% acetic acid over 20 minutes). LCMS: m/z 831.5 [M+H]$^+$, retention time=0.69 minutes; HPLC (Protocol B): retention time=5.240 minutes.

Step 4. Synthesis of N,2-dimethyl-N-[6-({[5-(methylsulfonyl)pyrazin-2-yl]carbonyl}amino)hexanoyl]alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#6)

To a solution of 5-(methylsulfonyl)pyrazine-2-carboxylic acid, #1 (5.5 mg, 0.027 mmol), and N,N-diisopropylethylamine (3 mL, 0.017 mmol) in N,N-dimethylformamide (0.1 mL) was added HATU (7.9 mg, 0.020 mmol). After about 15 minutes, a solution of #5 (13.5 mg, 0.016 mmol) and N,N-diisopropylethylamine (6 mL, 0.033 mmol) in N,N-dimethylformamide (0.2 mL) was added to the reaction mixture. After 45 minutes, LC-MS analysis demonstrated that the reaction was complete, and the mixture was directly purified by reverse phase chromatography according to a modified version of purification Method A (utilizing gradient elution of 20-95% acetonitrile in water containing 0.02% acetic acid over 20 minutes) to afford the title compound A (1.9 mg, 12%). LC-MS: m/z 1013.5 [M–H$^+$], 1039.5 [M+Na$^+$] retention time=1.61 minutes; HPLC (Protocol H): retention time=10.090 minutes.

Preparation of N,2-dimethyl-N-[6-({[2-(methyl-sulfonyl)-1,3-benzothiazol-6-yl]carbonyl}amino) hexanoyl]alanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#7)

Scheme for Compound #7

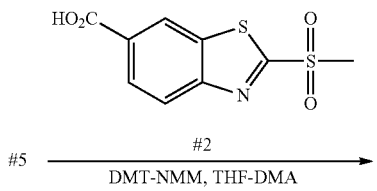

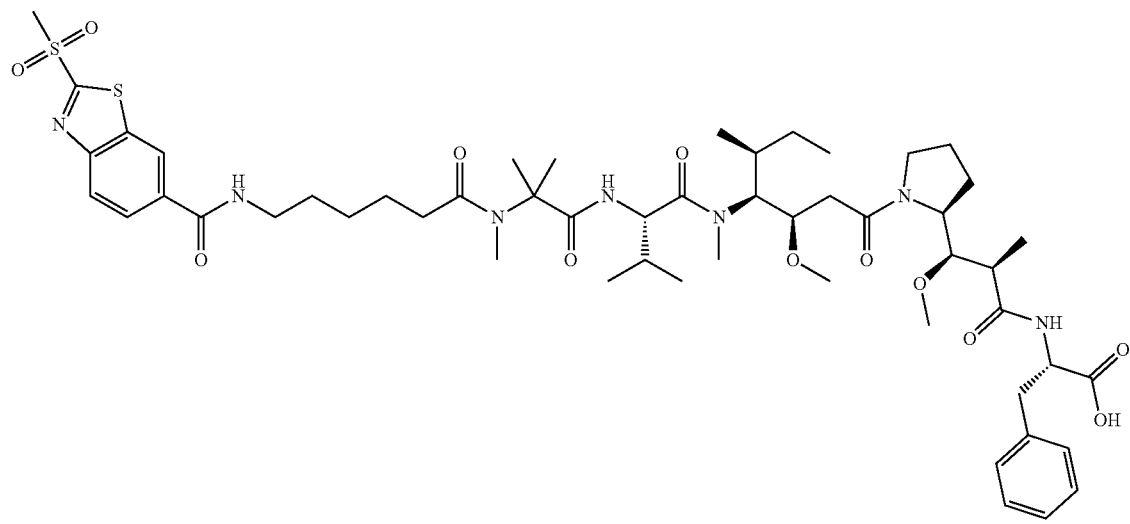

7

4-(4,6-Dimethoxy-1,3,5-triazin-2-yl)-4-methylmorpholinium chloride (DMT-NMM) (11.6 mg, 0.042 mmol) was added to a mixture of 2-(methylsulfonyl)-1,3-benzothiazole-6-carboxylic acid, #2 (11.0 mg, 0.043 mmol), in tetrahydrofuran (0.5 mL) followed by N-methyl morpholine (10 μL) at room temperature. After an hour, this mixture was added to a solution of #5 (21 mg, 0.022 mmol) in N,N-dimethylacetamide (1 mL). After an additional hour, LCMS demonstrated that the reaction was complete. The reaction mixture was diluted with acetonitrile and purified by reverse phase chromatography according to a modified version of purification Method A (utilizing gradient elution of 20-80% acetonitrile in water containing 0.02% acetic acid over 20 minutes) to afford the title compound #7 (3.3 mg, 3%). LCMS: m/z 1070.4 [M+H]$^+$, retention time=0.89 minutes; HPLC (Protocol B): retention time=5.722 minutes;

Preparation of 2-methyl-1-{23-[2-(methylsulfonyl)pyrimidin-5-yl]-23-oxo-4,7,10,13,16,19-hexaoxa-22-azatricosan-1-oyl}-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#10)

Scheme for Compound #10

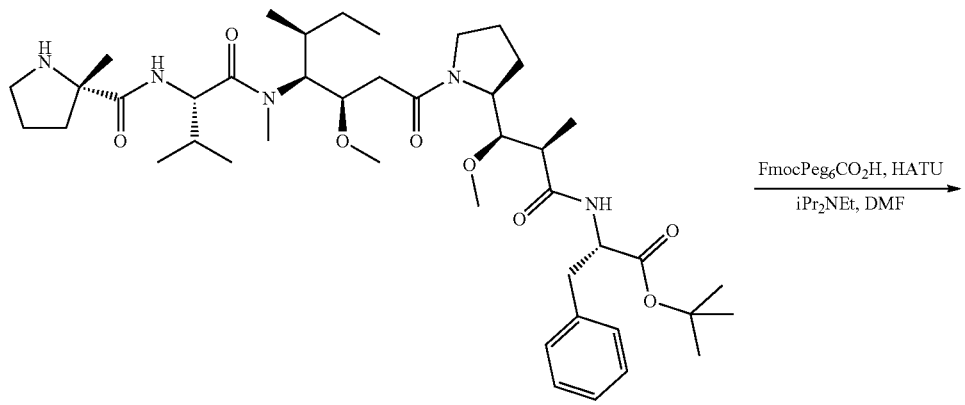

239¹

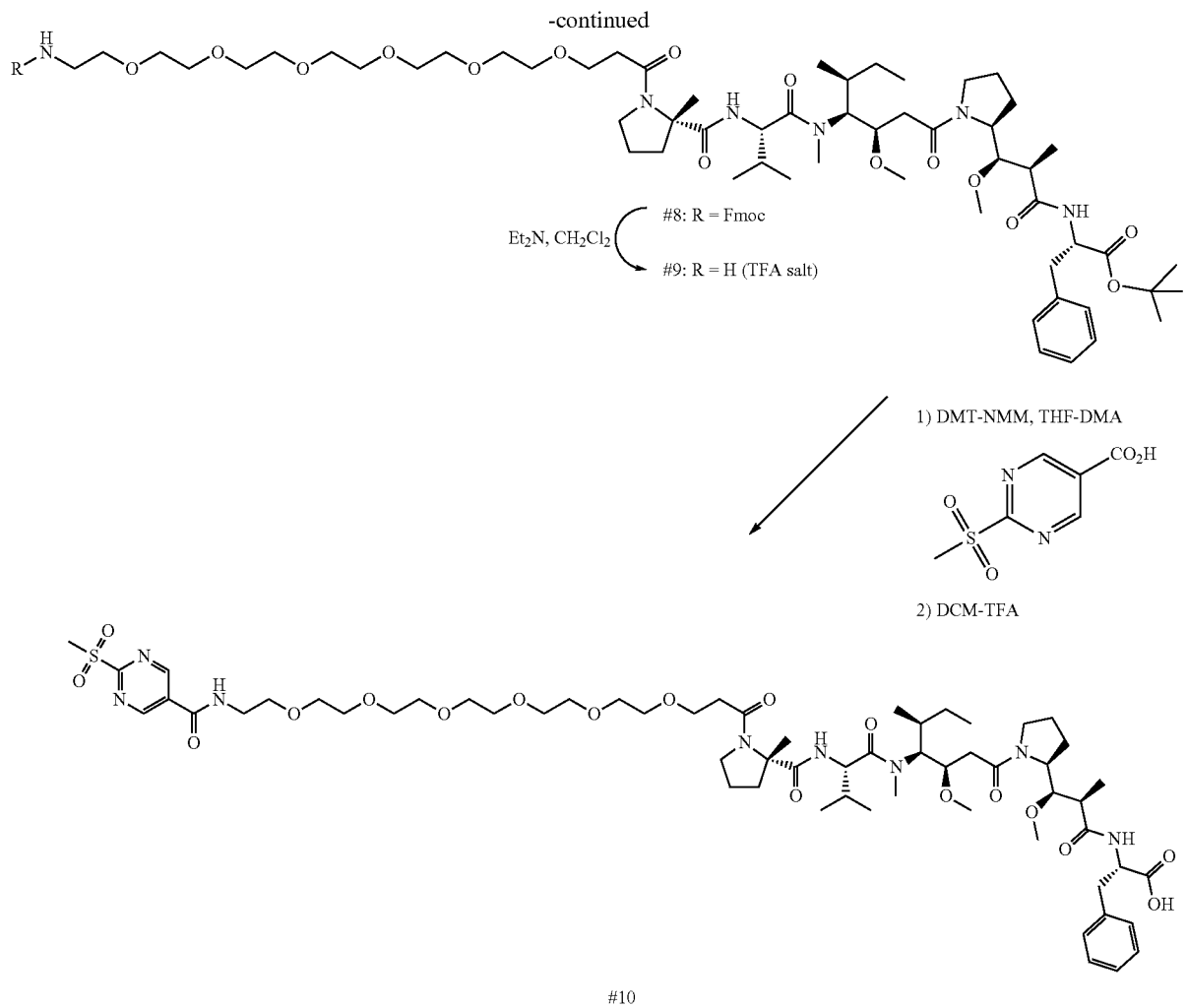

Step 1. Synthesis of 1-[1-(9H-fluoren-9-yl)-3,25-dioxo-2,7,10,13,16,19,22-heptaoxa-4-azapentacosan-25-yl]-2-methyl-L-prolyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#8)

According to general procedure B above, from 2-methyl-L-prolyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Example #239 in US 2013/0129753 A1) (237 mg, 0.302 mmol), 1-(9H-fluoren-9-yl)-3-oxo-2,7,10,13,16,19,22-heptaoxa-4-azapentacosan-25-oic acid (201 mg, 0.332 mmol), N,N-diisopropylethylamine (210 μL, 1.21 mmol), N,N-dimethylformamide (3 mL) and HATU (133 mg, 0.332 mmol) was synthesized #8 (238 mg, 59%) as a white foam after silica gel chromatography (Gradient: 10-100% acetone in heptane). LCMS: m/z 1344.1 [M+H]$^+$, retention time=2.33 minutes; HPLC (Protocol F): retention time=10.301 minutes; 1H NMR (400 MHz, CDCl3): δ 7.76 (d, 2H), 7.59 (d, 2H), 7.39 (m, 2H), 7.33 (m, 2H), 7.26-6.83 (m, 5H), 5.44 (br, 1H), 4.72-4.62 (m, 2H), 4.41 (d, 2H), 4.16 (m, 2H), 3.76-3.31 (m, 39H), 3.08-2.99 (m, 5H), 2.60-2.25 (m, 6H), 1.93-1.46 (m, 13H), 1.46 (m, 1H), 1.38 (s, 9H), 1.19 (m, 4H), 0.99-0.84 (m, 13H).

Step 2. Synthesis of 1-(21-amino-4,7,10,13,16,19-hexaoxahenicosan-1-oyl)-2-methyl-L-prolyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#9)

According to general procedure A above, from #8 (800 mg, 0.595 mmol), dichloromethane (20 mL) and diethylamine (2 mL, 20 mmol) was synthesized #9 (400 mg, 54%) as an amorphous solid after purification by reverse phase chromatography according to a modified version of purification Method A (utilizing gradient elution of 20-75% acetonitrile in water containing 0.02% trifluoracetic acid over 20 minutes). LCMS: m/z 1122.1 [M+H]$^+$, retention time=0.81 minutes; HPLC (Protocol B): retention time=6.282 minutes.

Step 3. Synthesis of of 2-methyl-1-{23-[2-(methyl-sulfonyl)pyrimidin-5-yl]-23-oxo-4,7,10,13,16,19-hexaoxa-22-azatricosan-1-oyl}-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#10)

To a white suspension of 2-(methylsulfonyl)pyrimidine-5-carboxylic acid (25.0 mg, 0.124 mmol) in tetrahydrofuran (0.5 mL) at room temperature were added 2-chloro-4,6-dimethoxy-1,3,5-triazine (22 mg, 0.12 mmol) followed by N-methyl morpholine (18 µL, 0.165 mmol). The suspension became thick and slightly yellow. N,N-Dimethylacetamide (0.2 mL) was added and the reaction mixture was stirred at room temperature. After 2 hours, LCMS showed full activation. A colorless solution of #9 (44 mg, 0.033 mmol) in tetrahydrofuran (0.5 mL) was added to the previous reaction mixture. After 40 min, LCMS analysis demonstrated that the reaction was complete. The reaction mixture was concentrated under a strong flow of nitrogen, diluted with dichloromethane (0.5 mL), and trifluoroacetic acid was added (1.5 mL). After 2 hours, LCMS analysis demonstrated that the Boc-deprotection reaction was complete. The mixture was diluted with DMSO and purified by reverse phase chromatography according to a modified version of purification Method A (utilizing gradient elution of 20-80% acetonitrile in water containing 0.02% trifluoracetic acid over 20 minutes) to afford the title compound #10 (18.2 mg, 44%) as a solid. LCMS (Protocol C): m/z 1250.6 [M+H]$^+$, retention time=8.252 minutes.

Preparation of 2-methyl-1-{23-[5-(methylsulfonyl)pyrazin-2-yl]-23-oxo-4,7,10,13,16,19-hexaoxa-22-azatricosan-1-oyl}-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#11)

Scheme for Compound #11

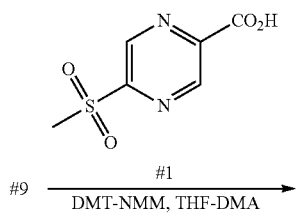

9 →(#1, DMT-NMM, THF-DMA)

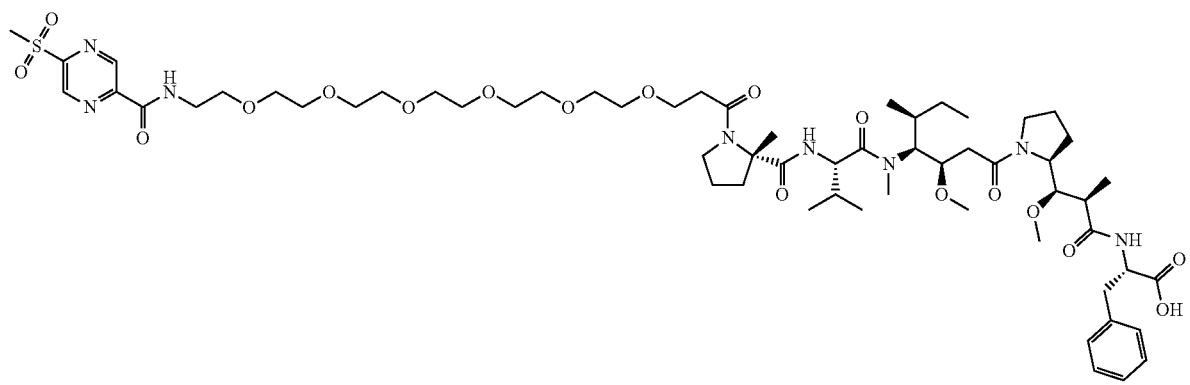

11

To a white suspension of 5-(methylsulfonyl)pyrazine-2-carboxylic acid, #1 (24.1 mg, 0.119 mmol) in tetrahydrofuran (0.5 mL) at room temperature were added 2-chloro-4,6-dimethoxy-1,3,5-triazine (21 mg, 0.12 mmol) followed by N-methyl morpholine (24.8 µL, 0.225 mmol). The suspension became thick and slightly yellow. N,N-Dimethylacetamide (0.2 mL) was added to help solubility. The reaction mixture was stirred at room temperature. After 2 hours, LCMS showed full activation. A colorless solution of compound #9 (66 mg, 0.045 mmol) in tetrahydrofuran (0.5 mL) was added to the previous reaction mixture. After 40 min, LCMS analysis demonstrated that the reaction was complete. The reaction mixture was concentrated under a strong flow of nitrogen, diluted with dichloromethane (0.5 mL), and trifluoroacetic acid was added (1.5 mL). After an hour, LCMS analysis demonstrated that the Boc-deprotection reaction was complete. The mixture was diluted with DMSO and purified by reverse phase chromatography according to a modified version of purification Method A (utilizing gradient elution of 20-80% acetonitrile in water containing 0.02% trifluoracetic acid over 20 minutes) to afford the title compound #11 (12.9 mg, 23%) as a solid. LCMS: m/z 1249.5 [M+H]$^+$, retention time=0.92 minutes; HPLCMS (Protocol C): m/z 1250.6 [M+H]$^+$, retention time=8.384 minutes.

Preparation of 2-methyl-1-{23-[2-(methylsulfonyl)-1,3-benzothiazol-6-yl]-23-oxo-4,7,10,13,16,19-hexaoxa-22-azatricosan-1-oyl}-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#14)

Scheme for Compound #14

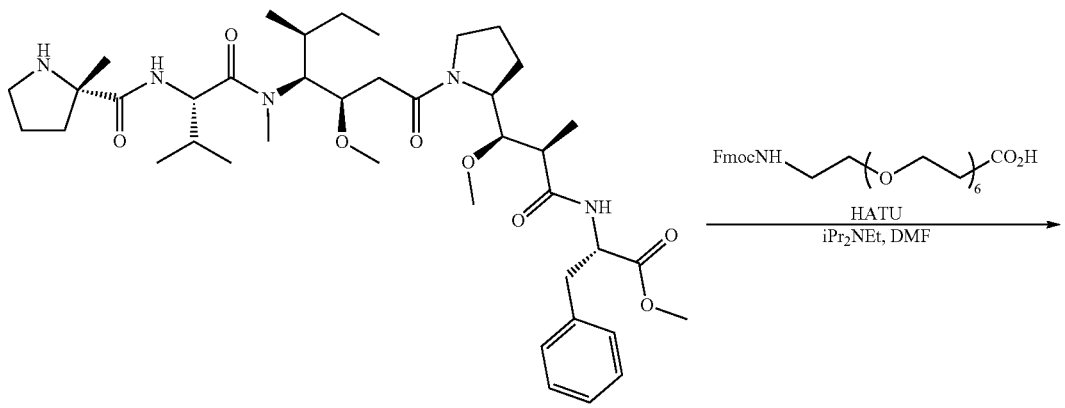

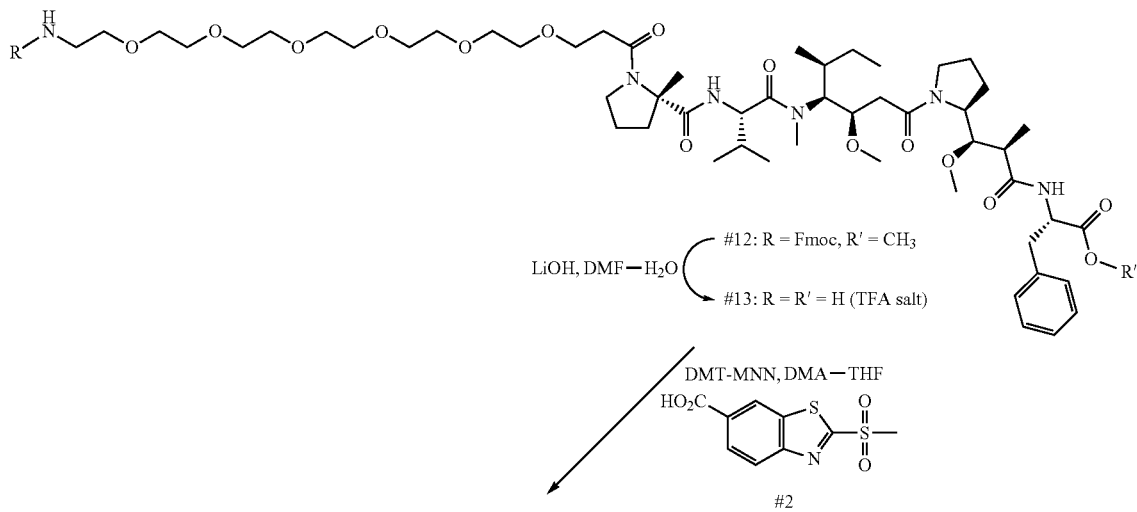

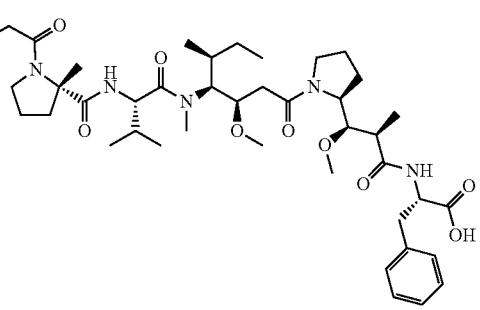
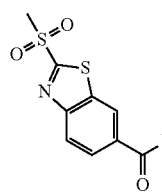

14

Step 1. Synthesis of 1-[1-(9H-fluoren-9-yl)-3,25-dioxo-2,7,10,13,16,19,22-heptaoxa-4-azapentacosan-25-yl]-2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#12)

According to general procedure B, from 2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (Example #117 in US 2013/0129753 A1) (115 mg, 0.146 mmol), 1-(9H-fluoren-9-yl)-3-oxo-2,7,10,13,16,19,22-heptaoxa-4-azapentacosan-25-oic acid (97.6 mg. 0.161 mmol), N,N-diisopropylethylamine (102 µL, 0.584 mmol), N,N-dimethylformamide and HATU (64.4 mg, 0.161 mmol) was synthesized #12 (164 mg, 86%) as a white foam after silica gel chromatography (Gradient: 10-100% acetone in heptane). LCMS: m/z 1302.1 [M+H]+, retention time=2.17 minutes; HPLC (Protocol G): retention time=4.158 minutes; 1H NMR (400 MHz, CDCl3): δ 7.77 (d, 2H), 7.61 (d, 2H), 7.39 (m, 2H), 7.33 (m, 2H), 7.22-6.95 (m, 7H), 5.44 (br, 1H), 4.86-4.70 (m, 3H), 4.42 (d, 2H), 4.24 (m, 3H), 3.87-3.55 (m, 29H), 3.38-3.32 (m, 9H), 3.10 (m, 4H), 2.61 (m, 2H), 2.41-2.39 (m, 3H), 1.91-1.62 (m, 13H), 1.30 (br 1H), 1.20 (d, 3H), 1.00-0.84 (m, 12H).

Step 2. Synthesis of 1-(21-amino-4,7,10,13,16,19-hexaoxahenicosan-1-oyl)-2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#13)

To a solution of #12 (88 mg, 0.068 mmol, 1 equiv) in N,N-dimethylformamide (1 mL) in an iced water bath was added a solution of lithium hydroxide (36 mg, 1.5 mmol) in water (0.4 mL). After 20 minutes, LCMS analysis demonstrated that the reaction was complete and was concentrated under a strong flow of nitrogen and the residue was purified by reverse phase chromatography according to Method B to afford compound #13 (189 mg, 71%) as a white solid. LCMS (Protocol C): m/z 1065.7 [M+H]+, retention time=6.959 minutes.

Step 3: 2-methyl-1-{23-[2-(methylsulfonyl)-1,3-benzothiazol-6-yl]-23-oxo-4,7,10,13,16,19-hexaoxa-22-azatricosan-1-oyl}-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#14)

To a white suspension of 2-(methylsulfonyl)-1,3-benzothiazole-6-carboxylic acid, #2 (5 mg, 0.02 mmol) in tetrahydrofuran (0.1 mL) at room temperature were added 4-(4,6-dimethoxy-1,3,5-triazin-2-yl)-4-methylmorpholinium chloride (DMT-MM), 5 mg, 0.018 mmol) followed by a drop of N-methyl morpholine. The reaction mixture was stirred at room temperature. After 2 hours, LCMS showed full activation. A colorless solution of #13 (10 mg, 0.009 mmol) in N,N-dimethylacetamide (0.1 mL) was added to the previous reaction mixture. LCMS analysis demonstrated that the reaction was complete after stirring at room temperature overnight and was then diluted with DMSO and purified by reverse phase chromatography according to Method A (Modifier: trifluoroacetic acid; Gradient: 20-90% acetonitrile in water) to afford the title compound #14 (0.9 mg, 8%) as a colorless glass. LCMS: m/z 1304.4 [M+H]+, retention time=1.70 minutes; HPLC (Protocol B): retention time=6.412 minutes.

Preparation of N-[6-({[2-(methylsulfonyl)pyrimidin-5-yl]carbonyl}amino)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#19)
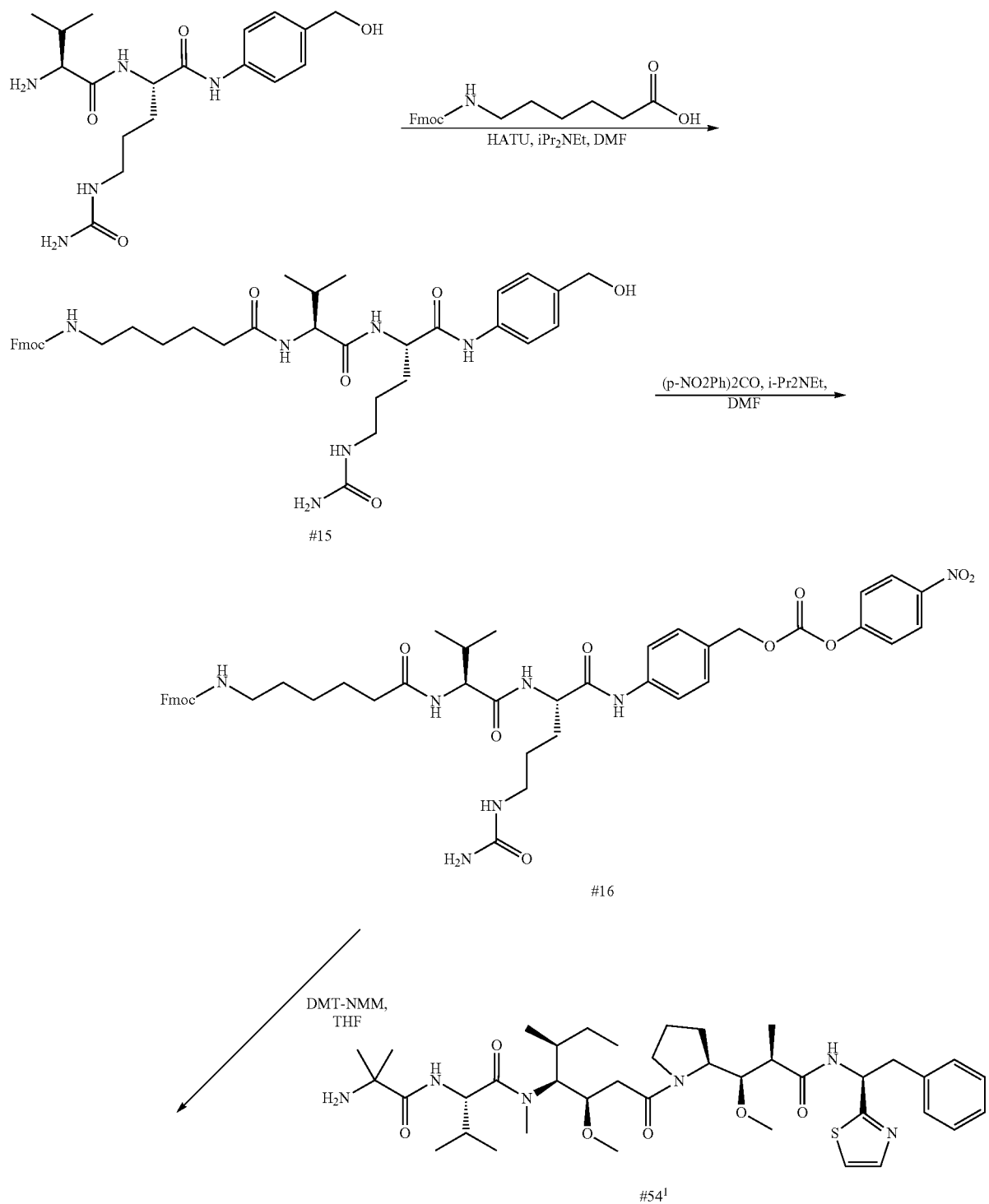

-continued

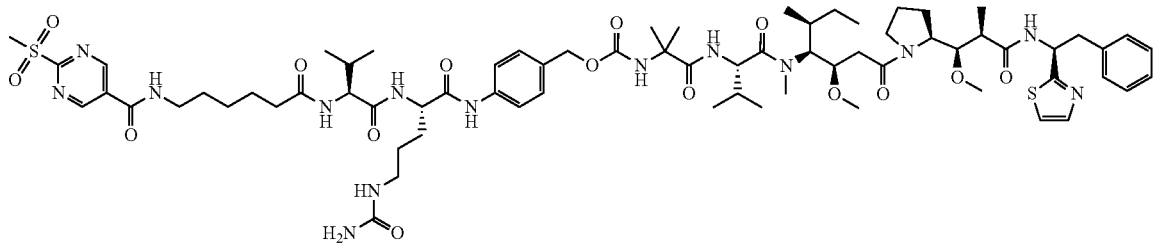

19

Step 1: Synthesis of Fmoc-AmCapValCitPABC-OH (#15): A solution of Fmoc-6-aminohexanoic acid (4.2 g, 11.40 mmol) in anhydrous N,N-dimethylformamide (50 mL) was treated with N,N-diisopropylethylamine (3.8 mL, 2.82 g, 21.8 mmol, 1.8 eq.) and HATU (5.6 g, 14.75 mmol, 1.25 eq.) and the mixture was stirred at room temperature for ten minutes. L-valyl-$N^5$-carbamoyl-N-[4-(hydroxymethyl)phenyl]-L-ornithinamide[2] [ValCitPABA] (Compound 64 in Dubowchik, G. M. et al. *Bioconjug Chem* 13, 855-69 (2002)[5] (5.6 g, 14.75 mmol, 1.25 eq.) was then added to the mixture and stirring was continued for 15 hours at room temperature. Dichloromethane was added to precipitate the product, which was filtered and air dried to provide 5.9 g (100%) of the desired material as an off-white solid. This material was used directly in subsequent reactions without further purification. MS (ES) m/z: 715.6 [M+H]$^+$.

Step 2: Synthesis of FmocAmCapValCitPABC-PNP (#16): A solution of FmocAmCapValCitPABA-OH, #15 (500 mg, 0.7 mmol), and bis-(4-nitrophenyl)carbonate (638 mg, 2.1 mmol, 3 eq.) in anhydrous N,N-dimethylformamide (3 mL) was treated with N,N-diisopropylethylamine (365 μL, 270 mg, 2.1 mmol, 3 eq.) and the reaction was stirred at room temperature overnight. The reaction mixture was concentrated in vacuo and the resulting residue was purified by silica gel chromatography using gradient elution of 0%-25% methanol in dichloromethane over 15 minutes, followed by isocratic elution of 25% methanol in dichloromethane. Pooled product containing fractions were evaporated to provide 402 mg (68%) of the desired product as an off-white solid. MS (ES) m/z: 880.3 [M+H]$^+$.

Step 3: Synthesis of N-(6-aminohexanoyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#18)

A solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (Example #54 in US 2013/0129753 A1) (105 mg, 0.141 mmol), FmocAmCapValCitPABC-PNP, #16 (138 mg, 0.157 mmol), HOAt (6.40 mg, 0.047 mmol), and 2,6-Lutidine (91 uL, 84 mg, 0.783 mmol) in N,N-dimethylformamide (1.4 mL) was heated at 45° C. for 21 hrs. Additional FmocAmCapValCitPABC-PNP, #16 (31 mg, 0.035 mmol), HOAt (3.83 mg, 0.028 mmol), and 2,6-Lutidine (16 uL, 15 mg, 0.141 mmol) were then added, the reaction was heated at 40° C. for an additional 6 hr., and then kept at room temperature overnight. LCMS analysis indicated that the reaction contained a mixture of compounds #17 and #18. Piperidine (0.5 mL) was added and the reaction stirred at room temperature for 1 hr. LCMS analysis indicated that the Fmoc-deprotection reaction was complete, and the reaction was concentrated and the residue was and purified by reverse phase chromatography according to a modified version of purification Method A (utilizing gradient elution of 10-85% acetonitrile in water containing 0.02% trifluoracetic acid over 20 minutes) to provide 97 mg (54%) of the desired product (#18) as white solid. LCMS (Protocol I): m/z 1062.3[M+H]+, retention time=2.36 minutes.

Step 4: Synthesis of N-[6-({[2-(methylsulfonyl)pyrimidin-5-yl]carbonyl}amino)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#19)

To a solution of N-(6-aminohexanoyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide, #18 (100 mg, 0.061 mmol), in tetrahydrofuran (1 mL) were added 2-(methylsulfonyl)pyrimidine-5-carboxylic acid (41 mg, 0.2 mmol) followed by 2-chloro-4,6-dimethoxy-1,3,5-triazine (35 mg, 0.20 mmol) and N-methyl morpholine (50 μL, 0.46 mmol). The reaction mixture was stirred at room temperature for 2 days then diluted with DMSO and purified by reverse chromatography according to a modified version of purification Method A (utilizing gradient elution of 20-90% acetonitrile in water containing 0.02% trifluoracetic acid over 20 minutes) to afford the title compound #19 (52 mg, 59%) as a white solid. LCMS (Protocol C): m/z 1445.6 [M+H]+, 723.5 [M+2H]/2+, retention time=8.721 minutes.

N-[6-({[5-(methylsulfonyl)pyrazin-2-yl]carbonyl}amino)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#26)

Scheme for Compound #26

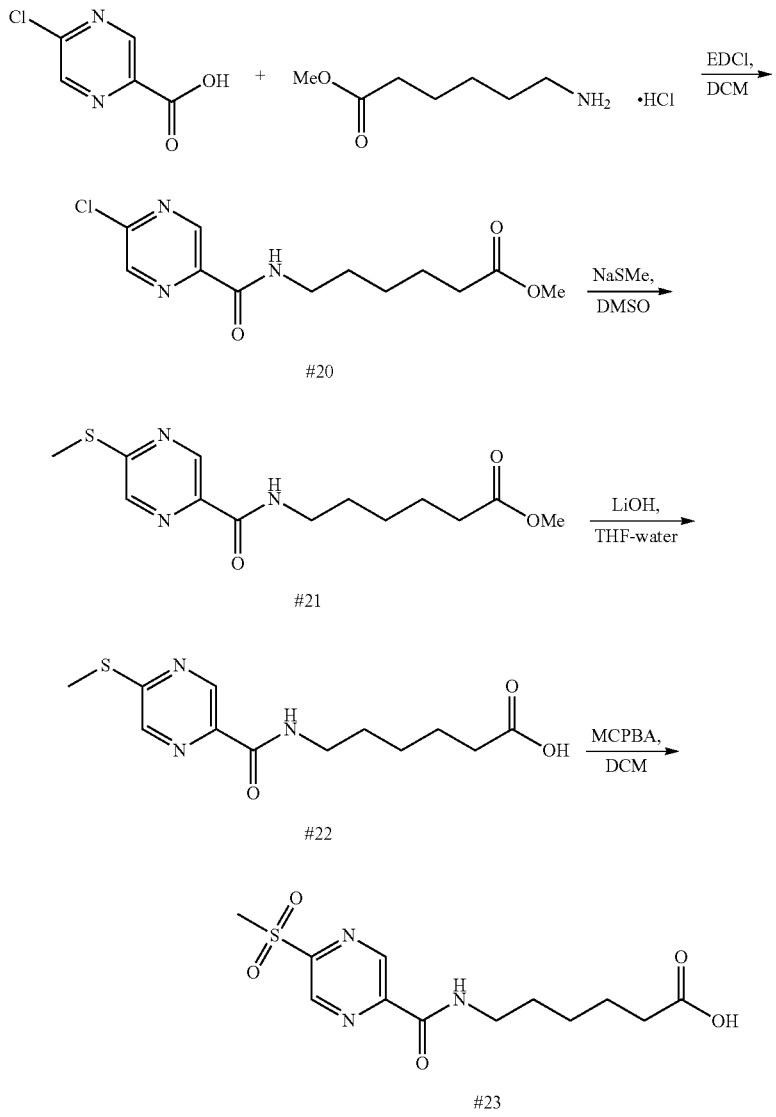

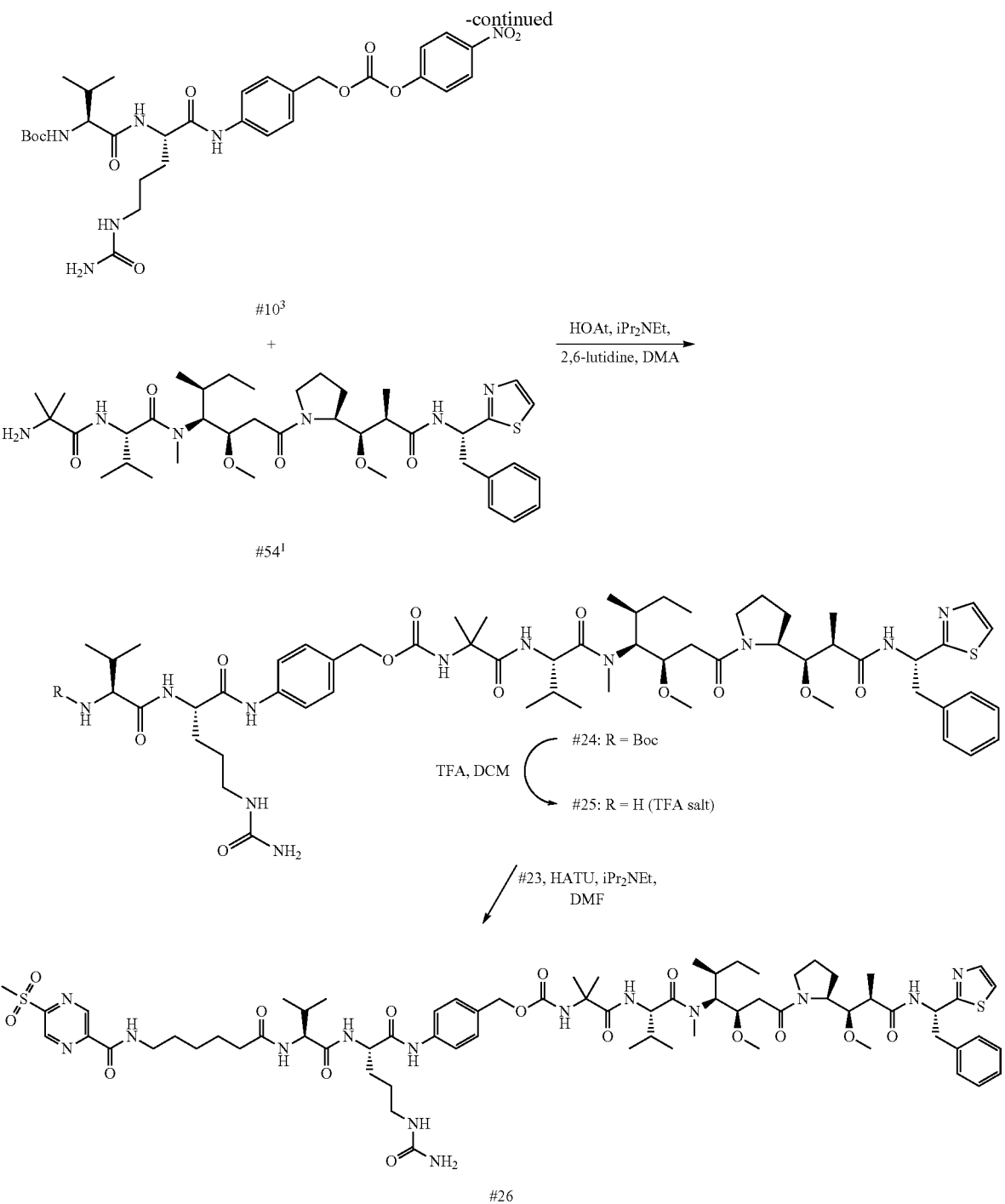

Step 1. Synthesis of methyl 6-{[(5-chloropyrazin-2-yl)carbonyl]amino}hexanoate (#20)

To a solution of 5-chloropyrazine-2-carboxylic acid (500 mg, 3.1 mmol) and methyl-6-aminohexanoate hydrochloride (688 mg, 3.71 mmol) in dichloromethane (15 mL) was added 1-ethyl-3-(3-dimethylaminopropyl)carbodiimide (711 mg, 3.71 mmol, 1.2 equiv). The reaction was allowed to stir for 18 hours at room temperature and was then diluted with dichloromethane (75 mL) and washed with 1N hydrochloric acid (15 mL). The layers were separated, and the organic layer was washed with brine, dried over anhydrous sodium sulfate, filtered, concentrated in vacuo and the residue was purified by flash column chromatography over silica gel (gradient elution with 20%-70% ethyl acetate in heptane) to provide methyl 6-{[(5-chloropyrazin-2-yl)carbonyl]-amino}hexanoate, #20 (378 mg, 43%), as a white solid. LCMS (Protocol E): m/z 308.2 [M+Na+], retention time=1.25 minutes; $^1$H NMR (500 MHz, DMSO-$d_6$): δ ppm 9.00 (d, J=1.22 Hz, 1 H), 8.96 (t, J=5.99 Hz, 1 H), 8.87 (d, J=1.47 Hz, 1 H), 3.58 (s, 3 H), 3.29 (q, J=6.85 Hz, 2 H), 2.30 (t, J=7.46 Hz, 2 H), 1.50-1.59 (m, 4 H), 1.25-1.33 (m, 2 H).

Step 2. Synthesis of methyl 6-({[5-(methylsulfanyl)pyrazin-2-yl]carbonyl}amino)hexanoate (#21)

To a solution of methyl 6-{[(5-chloropyrazin-2-yl)carbonyl]amino}hexanoate, #20 (374 mg, 1.31 mmol), in dimethyl sulfoxide (8 mL) was added sodium thiomethoxide (184 mg, 2.62 mmol). The reaction was allowed to stir for 18 hours at room temperature and was then diluted with dichloromethane (50 mL) and washed with saturated ammonium chloride (10 mL). The organic phase was washed with brine, dried over anhydrous sodium sulfate, filtered, and concentrated in vacuo to provide methyl 6-({[5-(methylsulfanyl)pyrazin-2-yl]carbonyl}amino)hexanoate (262 mg, 67%), #21, as a white solid. LCMS (Protocol E): m/z 298.2 $[M+H]^+$, retention time=1.35 minutes; $^1$H NMR (500 MHz, DMSO-$d_6$): δ 8.96 (d, J=1.47 Hz, 1 H), 8.77 (t, J=5.87 Hz, 1 H), 8.64 (d, J=1.71 Hz, 1 H), 3.58 (s, 3 H), 3.27 (q, J=6.77 Hz, 2 H), 2.62 (s, 3 H), 2.30 (t, J=7.34 Hz, 2 H), 1.49-1.59 (m, 4 H), 1.23-1.33 (m, 2 H).

Step 3. Synthesis of 6-({[5-(methylsulfanyl)pyrazin-2-yl]carbonyl}amino)hexanoic acid (#22)

To a solution of methyl 6-({[5-(methylsulfanyl)pyrazin-2-yl]carbonyl}amino)hexanoate, #21 (50 mg, 0.17 mmol), in tetrahydrofuran (1 mL) was added a solution of lithium hydroxide (8 mg, 0.3 mmol) in water (0.3 mL). The reaction was allowed to stir for 3 hours at room temperature. The reaction was diluted with dichloromethane (25 mL) and 1 N hydrochloric acid (6 mL) was added. The layers were separated and the organic layer was washed with brine (5 mL), dried over anhydrous sodium sulfate, filtered and concentrated in vacuo to provide 6-({[5-(methylsulfanyl)pyrazin-2-yl]carbonyl}amino)hexanoic acid, #22 (43 mg, 90%), as a white solid. LCMS (Protocol E): m/z 284.2 $[M+H]^+$, retention time=1.07 minutes; $^1$H NMR (500 MHz, DMSO-$d_6$): δ 11.98 (br. s., 1 H), 8.97 (d, J=1.47 Hz, 1 H), 8.77 (t, J=5.87 Hz, 1 H), 8.64 (d, J=1.47 Hz, 1 H), 3.28 (q, J=6.85 Hz, 2 H), 2.62 (s, 3 H), 2.20 (t, J=7.34 Hz, 2 H), 1.48-1.57 (m, 4 H), 1.25-1.33 (m, 2 H).

Step 4. Synthesis of 6-({[5-(methylsulfonyl)pyrazin-2-yl]carbonyl}amino)hexanoic acid (#23)

To a suspension of 6-({[5-(methylsulfanyl)pyrazin-2-yl]carbonyl}amino)hexanoic acid, #22 (40 mg, 0.14 mmol), in dichloromethane (2 mL) was added m-chloroperoxybenzoic acid (126 mg, 0.56 mmol). The reaction was allowed to stir for 18 hours at room temperature. The reaction was filtered and the solids collected to provide 6-({[5-(methylsulfonyl)pyrazin-2-yl]carbonyl}amino)hexanoic acid, #23 (33 mg, 74%) as a white solid. LCMS (Protocol A): m/z 316.2 $[M+H]^+$, retention time=0.54 minutes; $^1$H NMR (500 MHz, DMSO-$d_6$): δ 11.97 (br. s., 1 H), 9.34 (d, J=1.47 Hz, 1 H), 9.25 (d, J=1.22 Hz, 1 H), 9.18 (t, J=5.99 Hz, 1 H), 3.40 (s, 3 H), 3.29-3.36 (m, 2 H), 2.21 (t, J=7.34 Hz, 2 H), 1.49-1.60 (m, 4 H), 1.31 (quin, J=7.58 Hz, 2 H).

Step 5. Synthesis of N-(tert-butoxycarbonyl)-L-valyl-N-{4-[(8S,11S,12R)-11-[(2S)-butan-2-yl]-12(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#24)

To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (Example #54 in US 2013/0129753 A1) (50 mg, 0.067 mmol) in N,N-dimethylacetamide (1 mL) was added N-(tert-butoxycarbonyl)-L-valyl-$N^5$-carbamoyl-N-[4-({[(4-nitrophenoxy)carbonyl]oxy}methyl)phenyl]-L-ornithinamide (Compound 10 in U.S. Pat. No. 8,399,403 B2) (52 mg, 0.081 mmol), N,N-diisopropylethylamine (0.05 mL, 0.3 mmol), 2,6-lutidine (0.03 mL, 0.3 mmol), and 1-Hydroxy-7-azabenzotriazole (11 mg, 0.081 mmol). The reaction was allowed to stir at 45° C. for 24 h, and was then cooled to room temperature and allowed to stir for 2 days. The crude reaction was filtered and the filtrate was purified by reverse phase HPLC according to Method C to provide #24 (46 mg, 55%) as a white solid. LCMS (Protocol E): m/z 1248.8 $[M+H]^+$, retention time=1.83 minutes.

Step 6. Synthesis of L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, trifluoroacetate salt (#25)

Trifluoroacetic acid (0.1 mL, 1 mmol) was added to a solution of #24 (45 mg, 0.036 mmol) in dichloromethane (1 mL), and the reaction was allowed to stir at room temperature for 20 min. The reaction was concentrated under reduced pressure to provide L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, #25 (50 mg), as a white solid that was used directly without further purification. LCMS (Protocol E): m/z 1149.2 $[M+H]^+$, retention time=1.50 minutes.

Step 7. Synthesis of N-[6-({[5-(methylsulfonyl)pyrazin-2-yl]carbonyl}amino)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, trifluoroacetate salt (#26)

To a solution of 6-({[5-(methylsulfonyl)pyrazin-2-yl]carbonyl}amino)hexanoic acid, #23 (5 mg, 0.02 mmol), and L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, #25 (10 mg, 0.007 mmol) in N,N-dimethylformamide (0.2 mL, 0.04 mmol) was added (1-[Bis(dimethylamino)methylene]-1H-1,2,3-triazolo[4,5-b]pyridinium 3-oxid hexafluorophosphate) (3 mg, 0.008 mmol) and N,N-diisopropylethylamine (0.002 mL, 0.014 mmol). The reaction was allowed to stir for 24 hours at room temperature. The crude reaction was filtered and the filtrate was purified directly by reverse phase HPLC according to Method C to provide the title compound, #26 (3.7 mg, 37%), as a white solid. LCMS (Protocol E): m/z 1491.8 $[M+HCO_2^-]$, retention time=1.74 minutes.

Preparation of N-[6-({[2-(methylsulfonyl)-1,3-benzothiazol-6-yl]carbonyl}amino)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#30)

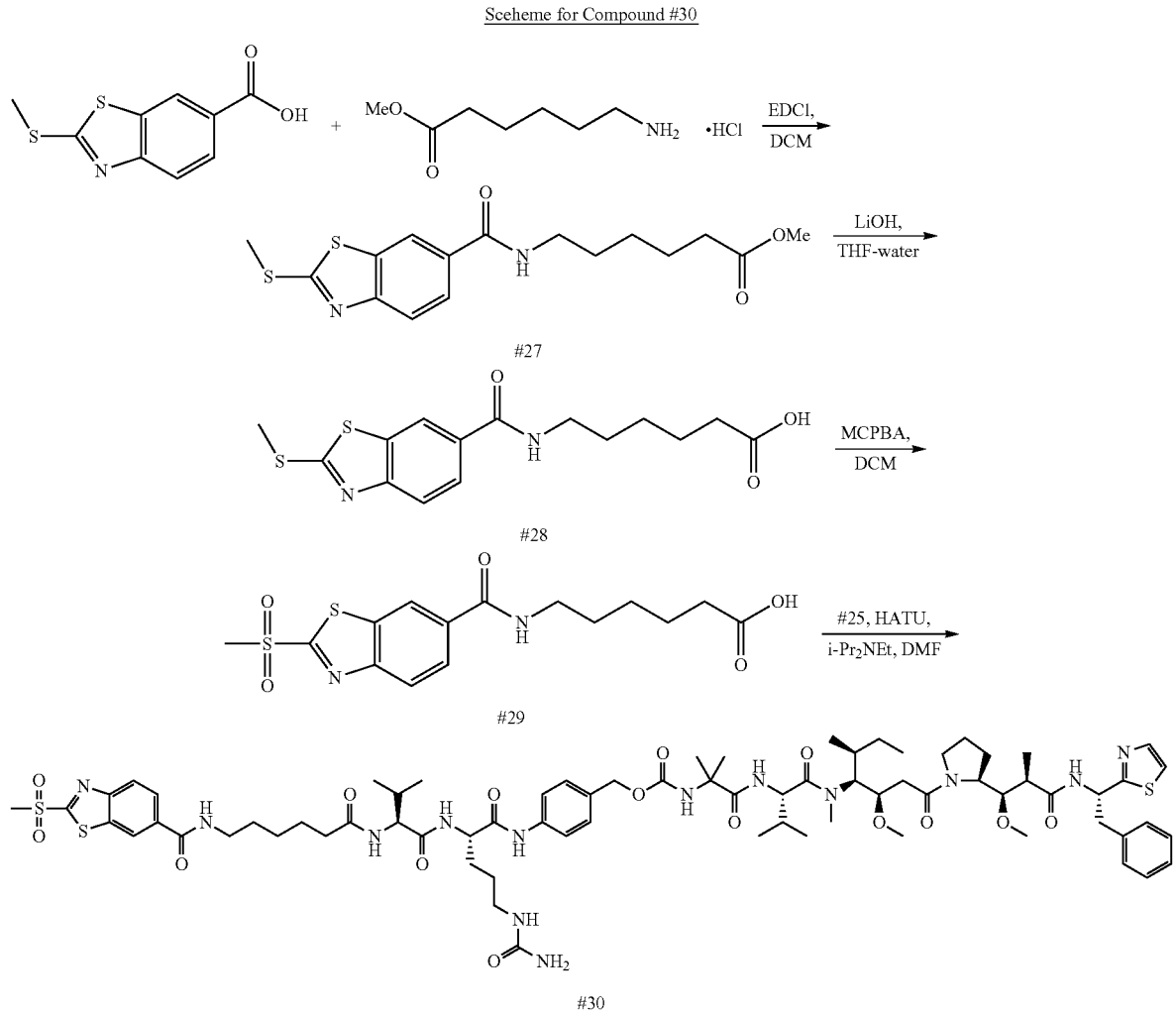

Sceheme for Compound #30

Step 1. Synthesis of methyl 6-({[2-(methylsulfanyl)-1,3-benzothiazol-6-yl]carbonyl}amino)-hexanoate (#27)

To a solution of 2-(methylsulfanyl)-1,3-benzothiazole-6-carboxylic acid[4] (500 mg, 2.22 mmol) and methyl 6-aminohexanoate hydrochloride (494 mg, 2.66 mmol) in dichloromethane (10 mL) was added 1-ethyl-3-(3-dimethylaminopropyl)carbodiimide (510 mg, 2.66 mmol). The reaction was allowed to stir for 18 hours at room temperature. The reaction was diluted with water (15 mL) and dichloromethane (75 mL). The aqueous layer was back-extracted with dichloromethane (50 mL). The combined organic layers were washed with brine (15 mL), dried over anhydrous sodium sulfate, filtered, concentrated in vacuo and purified by silica gel chromatography (Gradient: 50%-100% ethyl acetate in heptanes) to provide methyl 6-({[2-(methylsulfanyl)-1,3-benzothiazol-6-yl]carbonyl}amino)-hexanoate, #27 (189 mg, 24%), as a yellow solid. LCMS (Protocol E): m/z 353.2 [M+H]⁺, retention time=1.45 minutes; ¹H NMR (500 MHz, DMSO-d₆): δ 8.53 (t, J=5.62 Hz, 1 H), 8.48 (d, J=1.22 Hz, 1 H), 7.87-7.94 (m, 2 H), 3.58 (s, 3 H), 3.24-3.31 (m, 2 H), 2.82 (s, 3 H), 2.32 (t, J=7.34 Hz, 2 H), 1.56 (tt, J=14.58, 7.31 Hz, 4 H), 1.29-1.38 (m, 2 H).

Step 2. Synthesis of 6-({[2-(methylsulfanyl)-1,3-benzothiazol-6-yl]carbonyl}amino)hexanoic acid (#28)

To a solution of methyl 6-({[2-(methylsulfanyl)-1,3-benzothiazol-6-yl]carbonyl}amino)-hexanoate, #27 (50 mg, 0.14 mmol), in tetrahydrofuran (1 mL) was added a solution of lithium hydroxide (15 mg, 0.61 mmol) in water (0.3 mL). After 2 hours, the reaction was diluted with dichloromethane (30 mL) and acidified to pH=3 with 1N hydrochloride acid. The aqueous layer was back-extracted with dichloromethane (15 mL). The combined organic layers were dried over anhydrous sodium sulfate, filtered and concentrated in vacuo to provide 6-({[2-(methylsulfanyl)-1,3-benzothiazol-6-yl]carbonyl}amino)hexanoic acid, #28 (40 mg, 83%), as a yellow solid, which was used in the next step without further purification. LCMS (Protocol A): m/z 339.2 [M+H]$^+$, retention time=0.71 minutes; $^1$H NMR (500 MHz, DMSO-d$_6$): δ 8.65 (d, J=1.5 Hz, 1H), 8.53 (t, J=5.5 Hz, 1H), 8.48 (d, J=1.2 Hz, 1H), 8.02 (dd, J=8.3, 1.7 Hz, 1H), 7.87-7.95 (m, 2H), 3.27 (q, J=6.7 Hz, 2H), 2.82 (s, 3H), 2.22 (t, J=7.3 Hz, 2H), 1.54 (quin, J=7.5 Hz, 4H), 1.29-1.38 (m, 2H).

Step 3. Synthesis of 6-({[2-(methylsulfonyl)-1,3-benzothiazol-6-yl]carbonyl}amino)hexanoic acid (#29)

To a suspension of 6-({[2-(methylsulfanyl)-1,3-benzothiazol-6-yl]carbonyl}amino)hexanoic acid, #28 (39 mg, 0.12 mmol, 1 equiv), in dichloroethane (2 mL) was added m-chloroperoxybenzoic acid (103 mg, 0.46 mmol, 4 equiv). The reaction was allowed to stir for 24 hours at room temperature. The reaction was filtered and the solid collected to provide 6-({[2-(methylsulfonyl)-1,3-benzothiazol-6-yl]carbonyl}amino)hexanoic acid, #29 (27 mg, 63%) as a yellow solid, which was used in the next step without further purification. LCMS (Protocol E): m/z 371.2 [M+H]$^+$, retention time=0.98 minutes; $^1$H NMR (500 MHz, DMSO-d$_6$) δ: 11.96 (br. s., 1 H), 8.80 (s, 1 H), 8.70-8.76 (m, 1 H), 8.33 (d, J=8.80 Hz, 1 H), 8.11-8.15 (m, 1 H), 3.62 (s, 3 H), 3.27-3.32 (m, 2 H), 2.23 (t, J=7.34 Hz, 2 H), 1.56 (dq, J=14.82, 7.45 Hz, 4 H), 1.31-1.39 (m, 2 H).

Step 4. Synthesis of N-[6-({[2-(methylsulfonyl)-1,3-benzothiazol-6-yl]carbonyl}-amino)hexanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide (#30)

To a solution of 6-({[2-(methylsulfonyl)-1,3-benzothiazol-6-yl]carbonyl}amino)hexanoic acid, #29 (6 mg, 0.02 mmol), and L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide, #25 (9.6 mg, 0.007 mmol) in N,N-dimethylformamide (0.2 mL, 0.04 mmol) was added (1-[bis(dimethylamino)methylene]-1H-1,2,3-triazolo[4,5-b]pyridinium 3-oxid hexafluorophosphate) (3 mg, 0.008 mmol), and N,N-diisopropylethylamine (0.002 mL, 0.014 mmol). The reaction was allowed to stir for 24 hours at room temperature. The crude reaction mixture was filtered and the filtrate was purified by reverse phase HPLC according to Method C to provide the title compound, #30 (2.3 mg, 22%), as a white solid. LCMS (Protocol E): m/z 1502.3 [M+2H$^+$], retention time=1.79 minutes.

Preparation of N-{23-[5-(methylsulfonyl)pyrazin-2-yl]-23-oxo-4,7,10,13,16,19-hexaoxa-22-azatricosan-1-oyl}-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide (#35)

Scheme for Compound #35

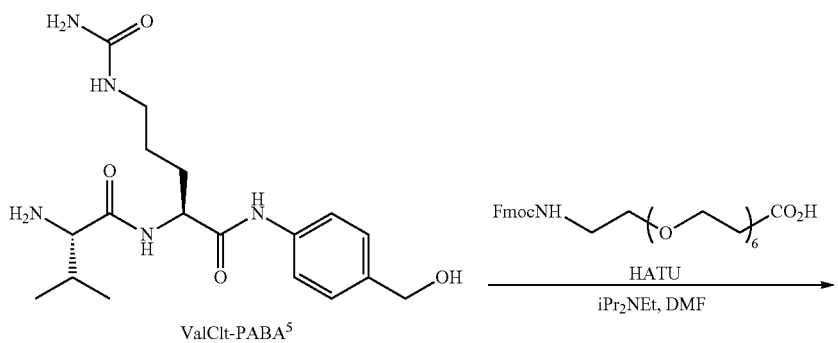

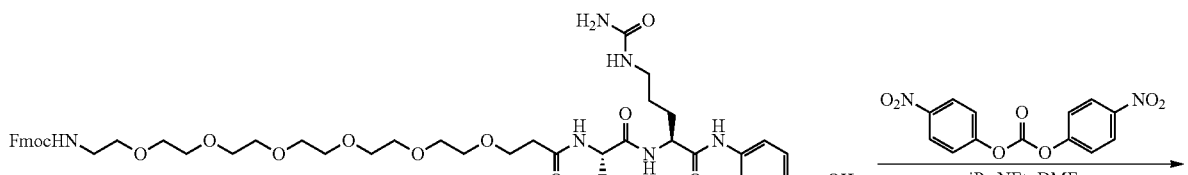

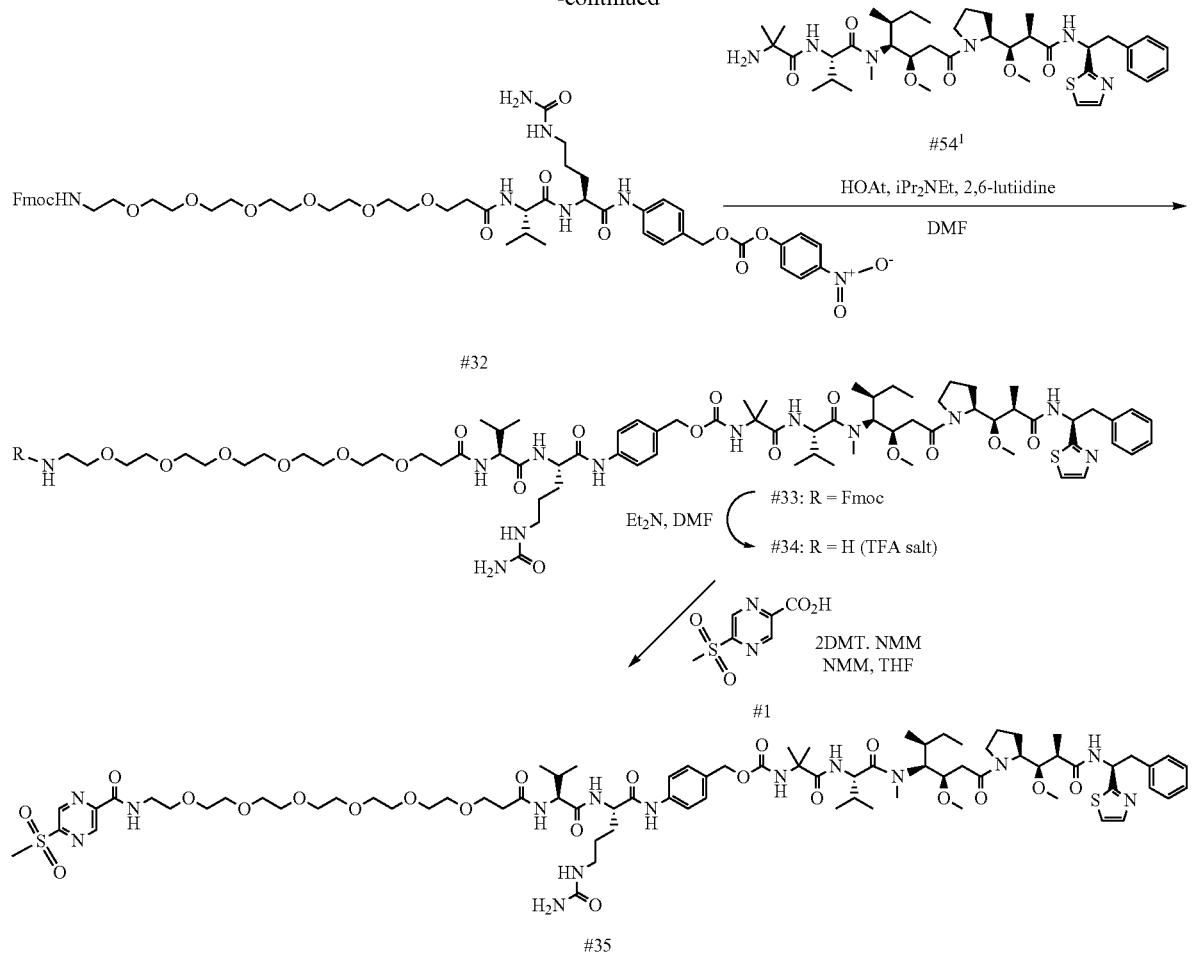

Step 1. Synthesis of N-[1-(9H-fluoren-9-yl)-3,25-dioxo-2,7,10,13,16,19,22-heptaoxa-4-azapentacosan-25-yl]-L-valyl-$N^5$-carbamoyl-N-[4-(hydroxymethyl)phenyl]-L-ornithinamide (#31)

According to general procedure B, to an ice cold stirred solution of L-valyl-$N^5$-carbamoyl-N-[4-(hydroxymethyl)phenyl]-L-ornithinamide [ValCitPABA] (Compound 64 in Dubowchik, G. M. et al. *Bioconjug Chem* 13, 855-69 (2002)[5] (1800 mg, 4.744 mmol), 1-(9H-fluoren-9-yl)-3-oxo-2,7,10,13,16,19,22-heptaoxa-4-azapentacosan-25-oic acid (2.73 g, 4.74 mmol), and N,N-diisopropylethylamine (736 mg,5.69 mmol) in N,N-dimethylformamide (12 mL) was added HATU (2160 mg, 5.69 mmol). The reaction was stirred at room temperature until complete by LCMS. The mixture was then diluted into ethyl acetate, and the resulting solids were collected by filtration to provide the title compound, #31 (1.9 g, 43%) as a yellow solid. LCMS (Protocol D): m/z 937.2 [M+H]$^+$, retention time=0.785 minutes; 1H NMR (400 MHz, DMSO): δ 9.89 (m, 1H), 8.10-8.08 (d, 1H), 7.89-7.86 (m, 2H), 7.70-7.68 (d, 2H), 7.55-7.53 (d, 2H), 7.43-7.41 (m, 2H), 7.34-7.31 (m, 2H), 7.24-7.22 (d, 1H), 5.97 (br, 1H), 5.41 (s, 2H), 5.11-5.08 (m, 1H), 4.43-4.20 (m, 5H), 3.59-3.58 (d, 2H), 3.49-3.48 (m, 18H), 3.41-3.38 (m, 4H), 2.40-2.33 (m, 2H), 1.99-1.94 (m, 1H), 1.69-1.17 (m, 6H), 0.86-0.82 (m, 6H).

Step 2. Synthesis of N-[1-(9H-fluoren-9-yl)-3,25-dioxo-2,7,10,13,16,19,22-heptaoxa-4-azapentacosan-25-yl]-L-valyl-$N^5$-carbamoyl-N-[4-({[(4-nitrophenoxy)carbonyl]oxy}methyl)phenyl]-L-ornithinamide (#32)

To a stirred yellow solution of N-[1-(9H-fluoren-9-yl)-3,25-dioxo-2,7,10,13,16,19,22-heptaoxa-4-azapentacosan-25-yl]-L-valyl-$N^5$-carbamoyl-N-[4-(hydroxymethyl)phenyl]-L-ornithinamide, #31 (9.35 g, 9.978 mmol) in anhydrous N,N-dimethylformamide (56 mL) in an iced-water bath was added bis(4-nitrophenyl) carbonate (9.11 g, 29.9 mmol) and N,N-diisopropylethylamine (1550 mg, 12.0 mmol). After stirring at room temperature for 1.5 hours, TLC (dichloromethane:methanol: ammonium hydroxide 10:1:0.1) showed the reaction complete. The reaction mixture was added dropwise into tent-butyl methyl ether (2 L) and stirred for 30 minutes. A white precipitate was formed and filtered to give the title compound #32 (7.2 g, 65.5%) as a white solid. LCMS (Protocol D): m/z 1102.2 [M+H]$^+$, 1124.2 [M+Na$^+$] retention time=0.882 minutes; 1H NMR (400 MHz, DMSO): δ 10.07 (s, 1H), 8.32-8.30 (d, 2H), 8.15-8.14 (d, 1H), 7.89-7.87 (m, 3H), 7.70-7.64 (m, 4H), 7.58-7.55 (d, 2H), 7.42-7.40 (m, 4H), 7.34-7.30 (m, 3H), 5.98 (br, 1H), 5.42 (s, 2H), 5.24 (s, 2H), 4.39-4.20 (m, 5H), 3.61-3.59 (d, 2H), 3.49-3.47 (m, 18H), 3.15-2.93 (m, 6H), 2.40-2.33 (m, 2H), 1.99-1.94 (m, 1H), 1.69-1.25 (m, 5H), 0.87-0.82 (m, 6H).

Step 3. Synthesis of N-(21-amino-4,7,10,13,16,19-hexaoxahenicosan-1-oyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide (#33)

To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (Example #54 in US 2013/0129753 A1) (189 mg, 0.254 mmol) in N,N-dimethylacetamide (1 mL) was added N-[1-(9H-fluoren-9-yl)-3,25-dioxo-2,7,10,13,16,19,22-heptaoxa-4-azapentacosan-25-yl]-L-valyl-N$^5$-carbamoyl-N-[4-({[(4-nitrophenoxy)carbonyl]oxy}methyl)phenyl]-L-ornithinamide, #32 [PF-06452175] (336 mg, 0.305), N,N-diisopropylethylamine (0.2 mL, 1 mmol), 2,6-lutidine (0.1 mL, 1 mmol) and 1-hydroxy-7-azabenzotriazole (42 mg, 0.31 mmol). The reaction was stirred at 45° C. overnight whereupon LCMS analysis demonstrated that the reaction was complete. The reaction mixture was purified directly by reverse phase chromatography over a 50 g C18 column, using gradient elution of 30-100% acetonitrile in water containing 0.02% trifluoroacetic acid over 20 mintues to afford the title compound, #33 (156 mg, 36%) as a gum. LCMS: m/z 1705.8 [M+H]$^+$, retention time=1.01 minutes; HPLC (Protocol B): retention time=6.225 minutes.

Step 4. Synthesis of N-(21-amino-4,7,10,13,16,19-hexaoxahenicosan-1-oyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide, trifluoroacetic acid salt (#34)

To a solution of N-(21-amino-4,7,10,13,16,19-hexaoxahenicosan-1-oyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N5-carbamoyl-L-ornithinamide, #33 (150 mg, 0.088 mmol), in N,N-dimethylformamide (1 mL) was added diethylamine (1 mL, 10 mmol). The reaction was stirred at room temperature overnight then was purified directly by reverse phase chromatography over a 50 g C18 column, using gradient elution of 20-100% acetonitrile in water containing 0.02% trifluoroacetic acid over 20 mintues to afford the title compound #34 (60 mg, 46%, purity >99%) as a white solid. LCMS: m/z 1483.9 [M+H]$^+$, retention time=1.39 minutes; HPLC (Protocol B): retention time=5.282 minutes.

Step 5. Synthesis of N-{23-[5-(methylsulfonyl)pyrazin-2-yl]-23-oxo-4,7,10,13,16,19-hexaoxa-22-azatricosan-1-oyl}-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide (#35)

To a solution of N-(21-amino-4,7,10,13,16,19-hexaoxahenicosan-1-oyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N5-carbamoyl-L-ornithinamide, trifluoroacetic acid salt, #34 (24.3 mg, 0.015 mmol) and 5-(methylsulfonyl)pyrazine-2-carboxylic acid, #1 (8.3 mg, 0.041 mmol), in tetrahydrofuran (0.5 mL) at room temperature were added N-methyl morpholine (one drop, ~20 uL) and 4-(4,6-dimethoxy-1,3,5-triazin-2-yl)-4-methylmorpholinium chloride (DMT-MM, 12.5 mg, 0.045 mmol). The resulting orange suspension became cloudier through time. After 30 min, LCMS analysis demonstrated that the reaction was complete so the reaction mixture was diluted with DMSO and purified directly by reverse phase chromatography according to a modified version of purification Method A (utilizing gradient elution of 20-90% acetonitrile in water containing 0.02% acetic acid over 20 minutes) to afford the title compound #35 (19.7 mg, 79%) as a glass. LCMS: m/z 1668.7 [M+H]$^+$, retention time=1.70 minutes; HPLCMS (Protocol C): m/z 1669.9 [M+H]$^+$, 835.5 [M/2+H$^+$] retention time=8.627 minutes.

Preparation of N-{23-[2-(methylsulfonyl)pyrimidin-5-yl]-23-oxo-4,7,10,13,16,19-hexaoxa-22-azatricosan-1-oyl}-L-valyl-N$^5$-carbamoyl-N-[4-({[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl]methyl)amino}ethyl)(methyl)carbamoyl]oxy}methyl)phenyl]-L-ornithinamide (#39)

Scheme for Compound #39
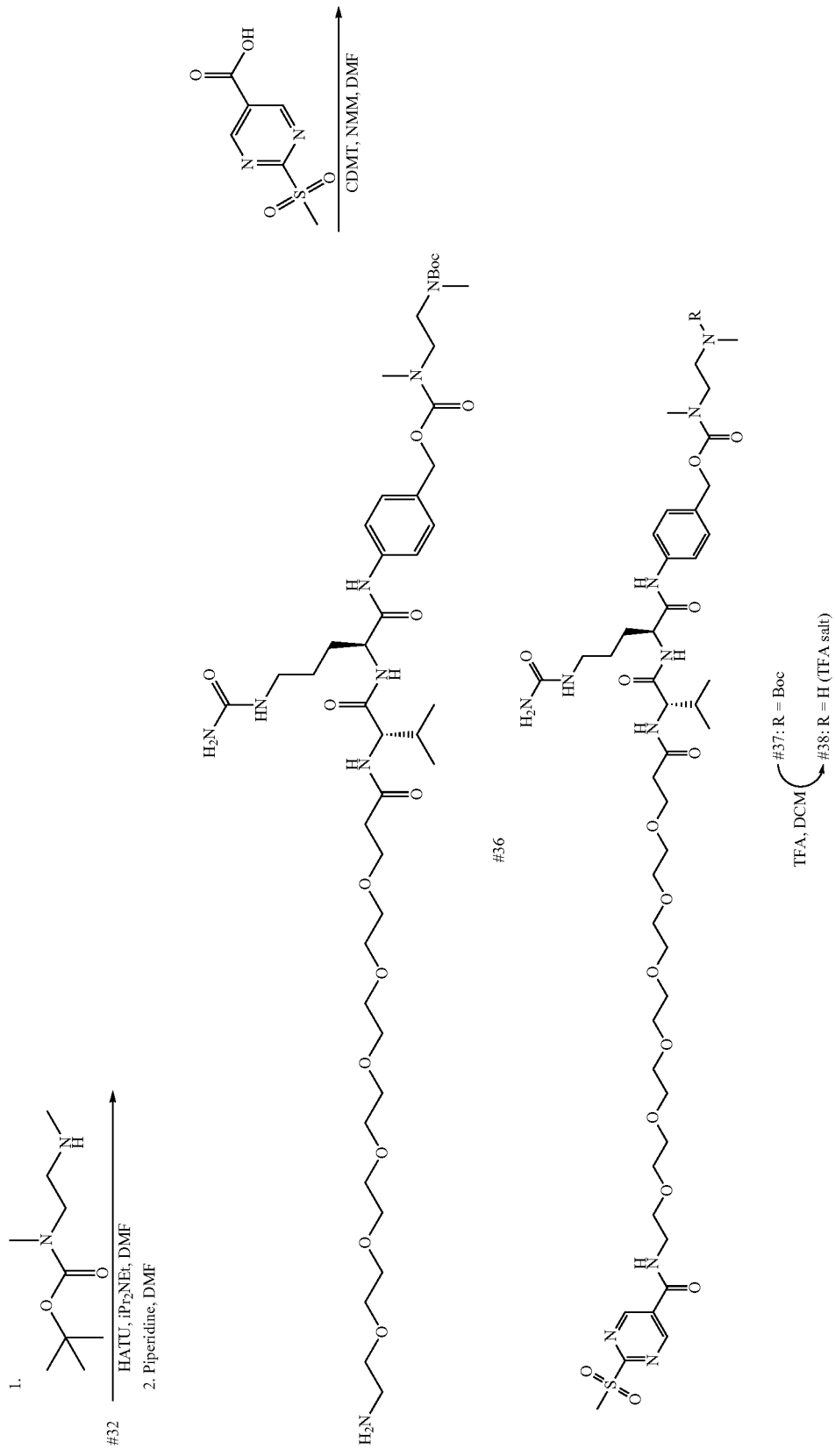

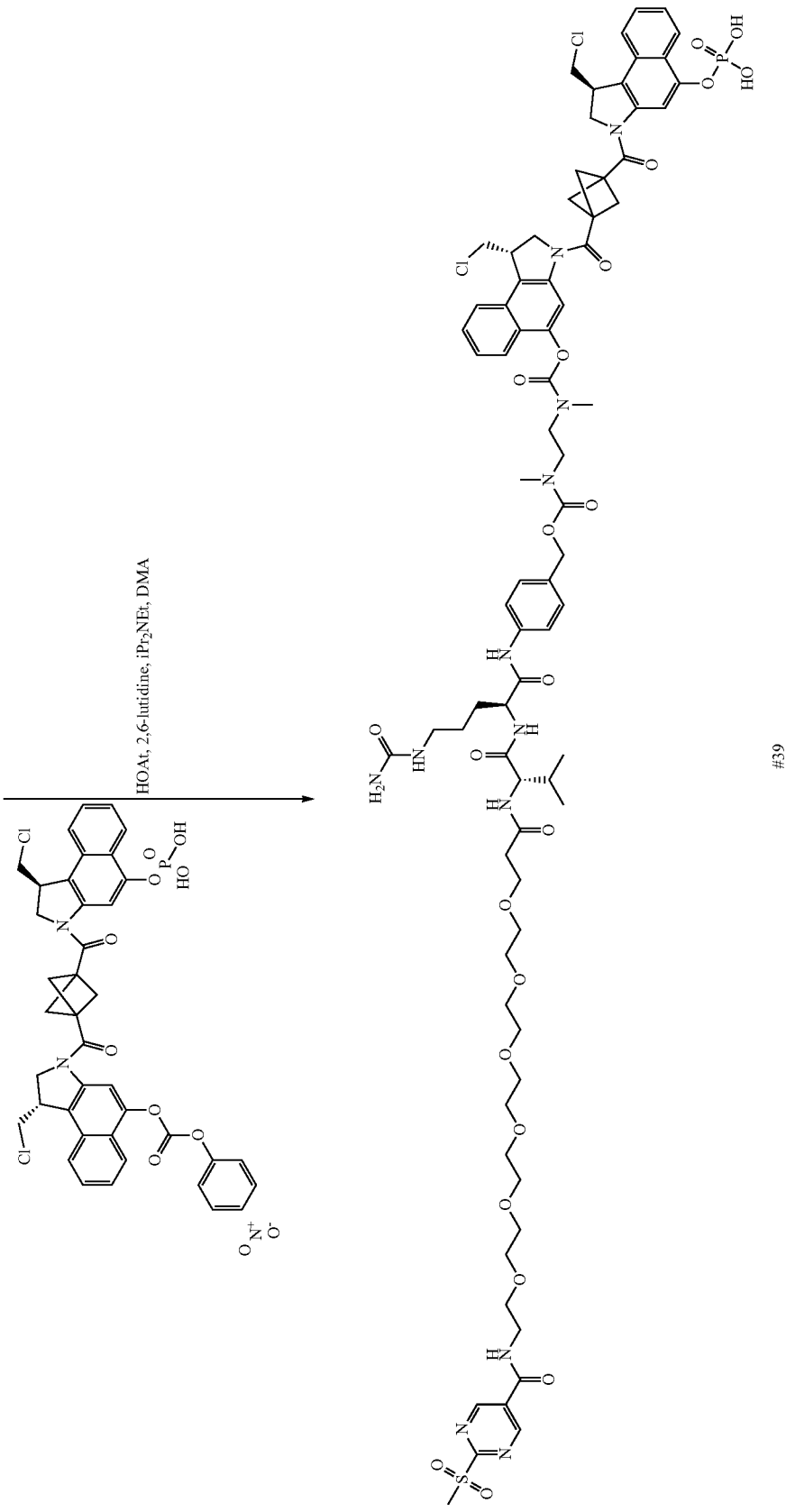

Step 1. Synthesis of N-(21-amino-4,7,10,13,16,19-hexaoxahenicosan-1-oyl)-L-valyl-N⁵-carbamoyl-N-[4-(4,7,10,10-tetramethyl-3,8-dioxo-2,9-dioxa-4,7-diazaundec-1-yl)phenyl]-L-ornithinamide, acetic acid salt (#36)

To a solution of N-[1-(9H-fluoren-9-yl)-3,25-dioxo-2,7,10,13,16,19,22-heptaoxa-4-azapentacosan-25-yl]-L-valyl-N5-carbamoyl-N-[4-({[(4-nitrophenoxy)carbonyl]oxy}methyl)phenyl]-L-ornithinamide, #32 (308.0 mg, 0.279 mmol), in N,N-dimethylacetamide (2 mL) were added tert-butyl methyl[2-(methylamino)ethyl]carbamate⁶ (56.0 mg, 0.30 mmol), 1-Hydroxy-7-azabenzotriazole (49 mg, 0.36 mmol), N,N-diisopropylethylamine (0.2 mL, 1 mmol) and 2,6-lutidine (0.1 mL, 0.8 mmol). The reaction was stirred at 45° C. overnight whereupon LCMS analysis demonstrated that the reaction was complete. The mixture was cooled to room temperature and piperidine (1 mL, 10 mmol) was added. After 15 minutes, LCMS showed complete loss of Fmoc protection with conversion to the amine. The mixture was concentrated under a strong flow of nitrogen and the resulting residue was purified by reverse phase chromatography over a 50 g C18 column, using gradient elution of 10-70% acetonitrile in water containing 0.02% acetic acid over 20 mintues to afford the title compound #36 (290 mg, quantitative) as a gum. LCMS: m/z 1014.8 [M+H]⁺, retention time=0.61 minutes; HPLC (Protocol B): retention time=5.179 minutes.

Step 2. Synthesis of N-{23-[2-(methylsulfonyl)pyrimidin-5-yl]-23-oxo-4,7,10,13,16,19-hexaoxa-22-azatricosan-1-oyl}-L-valyl-N⁵-carbamoyl-N-[4-(4,7,10,10-tetramethyl-3,8-dioxo-2,9-dioxa-4,7-diazaundec-1-yl)phenyl]-L-ornithinamide (#37)

To a solution of the acid 2-(methylsulfonyl)pyrimidine-5-carboxylic acid (281.0 mg, 1.39 mmol) and the acetate salt of N-(21-amino-4,7,10,13,16,19-hexaoxahenicosan-1-oyl)-L-valyl-N⁵-carbamoyl-N-[4-(4,7,10,10-tetramethyl-3,8-dioxo-2,9-dioxa-4,7-diazaundec-1-yl)phenyl]-L-ornithinamide, #36 (290.0 mg, 0.312 mmol), in N,N-dimethylacetamide (2 mL) were added 2-chloro-4,6-dimethoxy-1,3,5-triazine (241 mg, 1.37 mmol) followed by N-methyl morpholine (200 μL, 1.8 mmol). The reaction mixture was stirred at room temperature overnight whereupon LCMS analysis demonstrated that the reaction was complete. The mixture was purified directly by reverse phase chromatography over a 50 g C18 column, using gradient elution of 10-90% acetonitrile in water containing 0.02% acetic acid over 20 minutes to afford the title compound #37 (138.6 mg, 40%) as a white solid. LCMS: m/z 1113.5 [M+H]⁺, retention time=0.81 minutes; HPLC (Protocol B): retention time=5.774 minutes; 1H NMR (400 MHz, METHANOL-d4) d ppm 9.39 (s, 2 H) 7.65 (d, J=4.7 Hz, 2 H) 7.36 (d, J=8.2 Hz, 2 H) 5.10 (s, 2 H) 4.55 (dd, J=8.8, 4.9 Hz, 1 H) 4.17-4.28 (m, 1 H) 3.76-3.83 (m, 2 H) 3.70-3.76 (m, 2 H) 3.58-3.70 (m, 22 H) 3.30-3.37 (m, 8 H) 3.09-3.28 (m, 2 H) 2.95-3.03 (m, 3 H) 2.90 (s, 1 H) 2.80 (s, 2 H) 2.59 (t, J=6.0 Hz, 2 H) 2.36 (s, 3 H) 2.20 (s, 1 H) 2.09-2.19 (m, 1 H) 1.89-2.01 (m, 1 H) 1.72-1.86 (m, 1 H) 1.54-1.71 (m, 2 H) 1.47 (s, 9 H) 1.02 (t, J=6.2 Hz, 6 H).

Step 3. Synthesis of N-{23-[2-(methylsulfonyl)pyrimidin-5-yl]-23-oxo-4,7,10,13,16,19-hexaoxa-22-azatricosan-1-oyl}-L-valyl-N⁵-carbamoyl-N-{4-[({methyl[2-(methylamino)ethyl]carbamoyl}oxy)methyl]phenyl}-L-ornithinamide, trifluoroacetic acid salt #38

To a solution of N-{23-[2-(methylsulfonyl)pyrimidin-5-yl]-23-oxo-4,7,10,13,16,19-hexaoxa-22-azatricosan-1-oyl}-L-valyl-N⁵-carbamoyl-N-[4-(4,7,10,10-tetramethyl-3,8-dioxo-2,9-dioxa-4,7-diazaundec-1-yl)phenyl]-L-ornithinamide, #37 (136.0 mg, 0.122 mmol), in dichloromethane (1 mL) was added trifluoroacetic acid (0.5 mL, 7 mmol). After 20 min, LCMS analysis demonstrated that the reaction was complete, and the reaction mixture was concentrated under a stream of nitrogen, diluted with DMSO and purified by reverse phase chromatography according to a modified version of purification Method A (utilizing gradient elution of 5-60% acetonitrile in water containing 0.02% trifluoroacetic acid over 20 minutes) to give the title compound #38 (126 mg, 91.5%) as a gum. LCMS: m/z 1014.8 [M+H]⁺, retention time=0.61 minutes; HPLC (Protocol B): retention time=4.280 minutes.

Step 4: Synthesis of N-{23-[2-(methylsulfonyl)pyrimidin-5-yl]-23-oxo-4,7,10,13,16,19-hexaoxa-22-azatricosan-1-oyl}-L-valyl-N⁵-carbamoyl-N-[4-({[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide (#39)

A solution of the trifluoroacetate salt of N-{23-[2-(methylsulfonyl)pyrimidin-5-yl]-23-oxo-4,7,10,13,16,19-hexaoxa-22-azatricosan-1-oyl}-L-valyl-N⁵-carbamoyl-N-{4-[({methyl[2-(methylamino)ethyl]carbamoyl}oxy)methyl]phenyl}-L-ornithinamide, #38 (37.9 mg, 0.0336 mmol) in N,N-dimethylacetamide (1 mL) and a solution of (1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl 4-nitrophenyl carbonate (28 mg, 0.034 mmol) were combined. 1-Hydroxy-7-azabenzotriazole (4.58 mg, 0.0336 mmol) was added followed by 2,6-lutidine (15.7 mL, 0.135 mmol) and N,N-diisopropylethylamine (23.7 mL, 0.135 mmol). The reaction mixture immediately turned yellow, and the reaction was allowed to stand overnight at room temperature. The crude reaction mixture was purified directly according to a modified version of purification Method A (utilizing gradient elution of 0-100% acetonitrile in water containing 0.02% trifluoroacetic acid over 20 minutes) to provide the title compound #39 (21.3 mg, 37%) as a glass. LCMS: m/z 1707.7 [M+H]⁺, retention time 0.82 min.

Preparation of N-acetyl-3-({[2-(methylsulfonyl) pyrimidin-5-yl]carbonyl}amino)-L-alanyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#43)
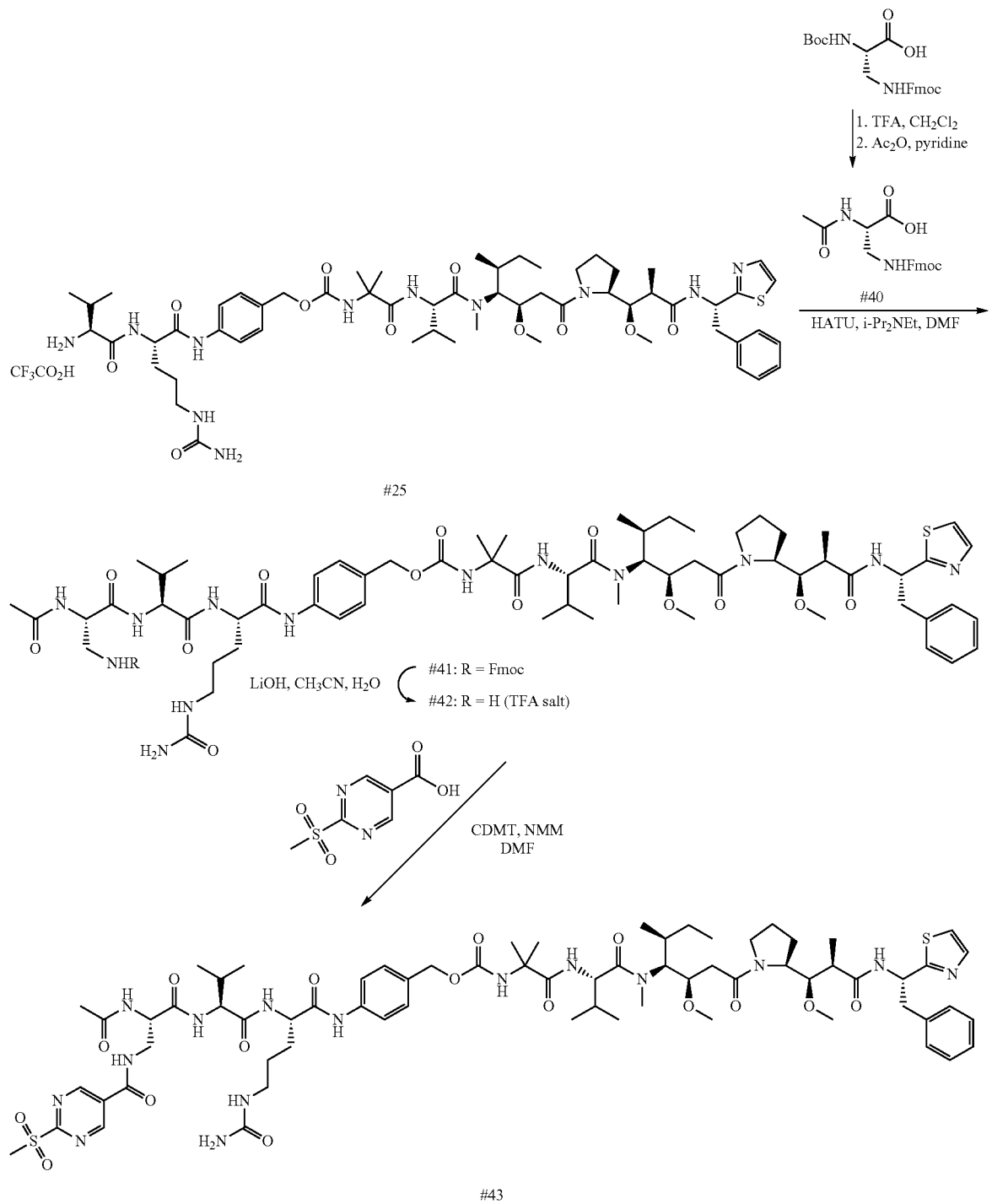

Step 1: Synthesis of N-acetyl-3-{[(9H-fluoren-9-ylmethoxy)carbonyl]amino}-L-alanine (#40)

To a suspension of Boc-N-β-Fmoc-L-diaminopropionic acid (346 mg, 0.811 mmol) in dichloromethane (2 mL) was added trifluoroacetic acid (2 mL) resulting in a colorless solution. After 30 minutes, the thick white reaction mixture was concentrated under reduced pressure. The residue was diluted with pyridine, cooled with an iced water bath and acetic anhydride (250 uL, 2.68 mmol) was then added dropwise. After 20 min, the reaction mixture was concentrated under reduced pressure, diluted with dimethyl sulfoxide and purified directly by reverse phase chromatography according to a modified version of purification Method A (utilizing gradient elution of 10-80% acetonitrile in water containing 0.02% trifluoroacetic acid over 20 minutes) to afford the title compound #40 (169 mg, 56%) as a glass. LCMS (Protocol A): m/z 369.3 [M+H]$^+$, retention time=0.92 minutes; HPLC (Protocol B): retention time=6.065 minutes. 1H NMR (400 MHz, METHANOL-d4) d ppm 7.79 (d, J=7.8 Hz, 2 H) 7.64 (d, J=7.4 Hz, 2 H) 7.38 (t, J=7.4 Hz, 2 H) 7.31 (t, J=7.4 Hz, 2 H) 4.55 (t, J=5.9 Hz, 1 H) 4.33 (d, J=6.6 Hz, 2 H) 4.20 (t, J=6.8 Hz, 1 H) 3.60 (dd, J=14.2, 4.5 Hz, 1 H) 3.45 (dd, J=14.0, 7.4 Hz, 1 H) 1.97 (s, 3 H)

Step 2: Synthesis of N-acetyl-3-{[(9H-fluoren-9-ylmethoxy)carbonyl]amino}-L-alanyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide (#41)

In an iced water bath, to a solution of L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide, trifluoroacetate salt, #25 (40.0 mg, 0.032 mmol) in N,N-dimethylacetamide (400 μL) were added N-acetyl-3-{[(9H-fluoren-9-ylmethoxy)carbonyl]amino}-L-alanine, #40 (11.7 mg, 0.0317 mmol), HATU (25.0 mg, 0.066 mmol) and N,N-diisopropylethylamine (81.9 μL, 0.475 mmol). The reaction was allowed to stir for 15 minutes and was then diluted with dimethyl sulfoxide and purified directly by reverse phase chromatography according to a modified version of purification Method A (utilizing gradient elution of 20-100% acetonitrile in water containing 0.02% trifluoroacetic acid over 20 minutes) to afford the title compound #41 (9.7 mg, 20%) as a white solid. LCMS (Protocol A): m/z 1500.0 [M+H]$^+$, retention time=1.11 minutes; HPLC (Protocol B): retention time=7.449 minutes.

Step 3. Synthesis of N-acetyl-3-amino-L-alanyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide, trifluoroacetic acid salt (#42)

To a solution of #41 (9.0 mg, 0.006 mmol) in acetonitrile (1 mL) in an iced water bath was added a solution of lithium hydroxide (10 mg, 0.2 mmol) in water (0.1 mL). After 45 minutes, LCMS analysis demonstrated that the reaction was complete and was then neutralized with acetic acid, diluted with dimethyl sulfoxide and purified directly by reverse phase chromatography according to a modified version of purification Method A (utilizing gradient elution of 15-90% acetonitrile in water containing 0.02% trifluoroacetic acid over 20 minutes) to afford the title compound #42 (2.8 mg, 30%), as a white solid. LCMS (Protocol A): m/z 1298.8 [M+H]$^+$, retention time=0.80 minutes; HPLC (Protocol B): retention time=5.717 minutes.

Step 4. Synthesis of N-acetyl-3-({[2-(methylsulfonyl)pyrimidin-5-yl]carbonyl}amino)-L-alanyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide (#43)

A mixture of the acid 2-(methylsulfonyl)pyrimidine-5-carboxylic acid (20.0 mg, 0.099 mmol) and the trifluoroacetic acid salt of N-acetyl-3-amino-L-alanyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N$^5$-carbamoyl-L-ornithinamide, #43 (2.8 mg, 0.0022 mmol) were diluted with methanol and toluene and concentrated to dryness. This was repeated 2 more times. To the resulting mixture in N,N-dimethylacetamide (0.5 mL) were added 2-chloro-4,6-dimethoxy-1,3,5-triazine (5 mg, 0.03 mmol) followed by N-methyl morpholine (50 μL, 0.45 mmol). The reaction mixture was stirred at room temperature for an hour whereupon LCMS analysis demonstrated that the reaction was complete. The mixture was diluted with dimethyl sulfoxide and purified directly by reverse phase chromatography according to a modified version of purification Method A (utilizing gradient elution of 10-80% acetonitrile in water containing 0.02% trifluoroacetic acid over 20 minutes) to afford the title compound #43 (1.0 mg, 31%), as a white solid. LCMS (Protocol A): m/z 1461.8 [M+H]$^+$, retention time=0.93 minutes; HPLC (Protocol B): retention time=6.362 minutes.

Preparation of N-[(2S)-2-(acetylamino)-4-({[2-(methylsulfonyl)pyriidin-5-yl]carbonyl}amino)butanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#46)
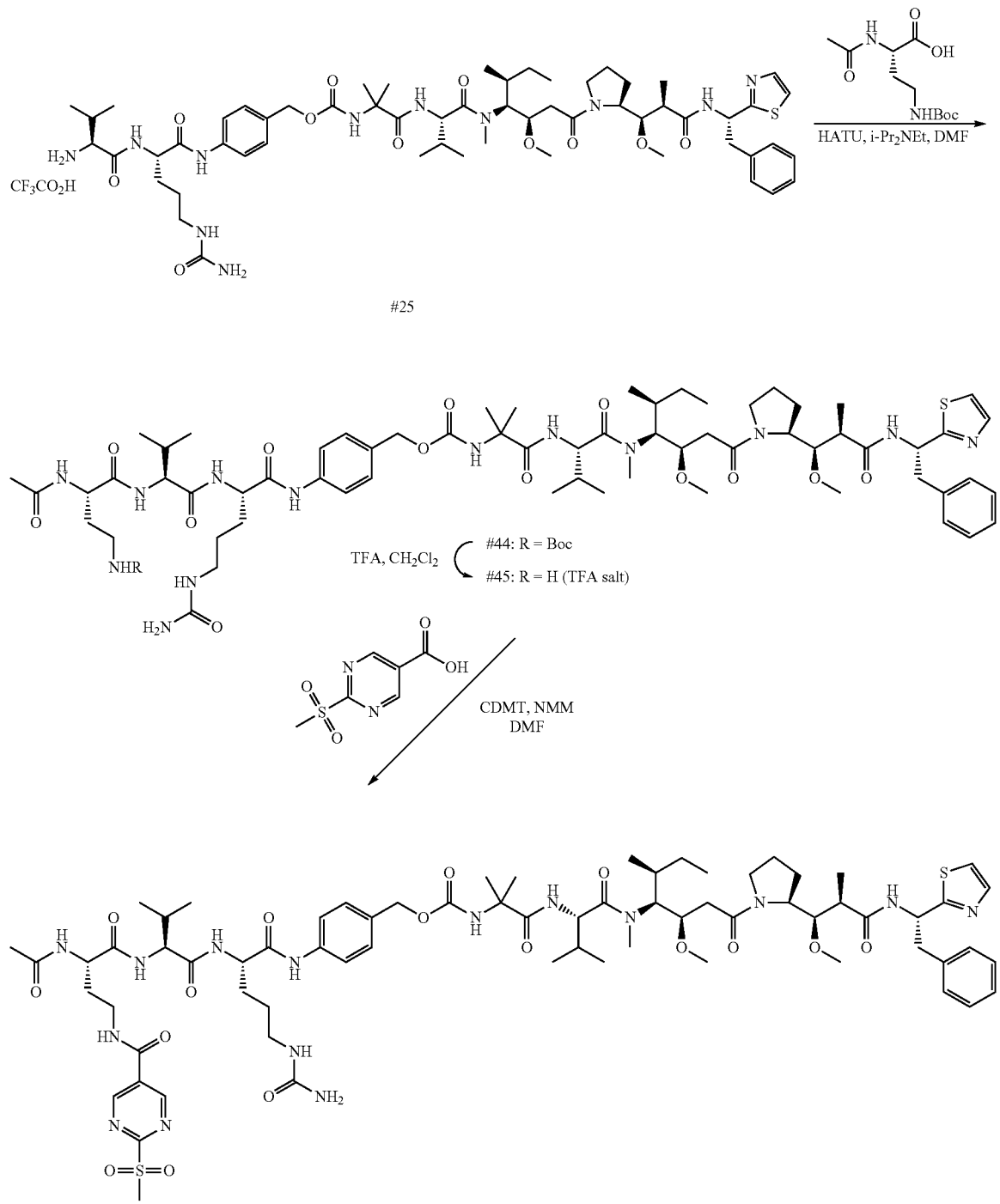

Step 1. Synthesis of N-{(2S)-2-(acetylamino)-4-[(tert-butoxycarbonyl)amino]butanoyl}-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#44)

In an iced water bath, to a solution of L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, trifluoroacetate salt, #25 (60.0 mg, 0.048 mmol) in N,N-dimethylacetamide (600 µL) were added Ac-Dab(Boc)-OH (23.2 mg, 0.0891 mmol), HATU (33.4 mg, 0.0878 mmol) and N,N-diisopropylethylamine (23.0 µL, 0.13 mmol). The reaction was allowed to stir overnight at room temperature. The reaction mixture was then diluted with dimethyl sulfoxide and purified directly by reverse phase chromatography according to a modified version of purification Method A (utilizing gradient elution of 20-100% acetonitrile in water containing 0.02% trifluoroacetic acid over 20 minutes) to afford the title compound #44 (18.7 mg, 29%), as a white solid. LCMS (Protocol A): m/z 1391.9 [M+H]$^+$, retention time=0.98 minutes; HPLC (Protocol B): retention time=6.643 minutes.

Step 2. Synthesis of N-[(2S)-2-(acetylamino)-4-aminobutanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, trifluoroacetic acid salt (#45)

Trifluoroacetic acid (1 mL, 10 mmol) was added to a solution of #44 (13.6 mg, 0.0098 mmol) in acetonitrile (2 mL), and the reaction was allowed to stir at room temperature for 20 min. The reaction was concentrated under reduced pressure to provide the title compound #45 (13.7 mg), as a white solid that was used directly without further purification. LCMS (Protocol E): m/z 1290.9 [M+H]$^+$, retention time=0.84 minutes.

Step 3. Synthesis of N-[(2S)-2-(acetylamino)-4-({[2-(methylsulfonyl)pyrimidin-5-yl]carbonyl}amino)butanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#46)

To a solution the trifluoroacetic acid salt of N-[(2S)-2-(acetylamino)-4-aminobutanoyl]-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, #45 (13.7 mg, 0.00975 mmol) in N,N-dimethylacetamide (1 mL) were added of 2-(methylsulfonyl)pyrimidine-5-carboxylic acid (27.9 mg, 0.138 mmol) and 2-chloro-4,6-dimethoxy-1,3,5-triazine (24.0 mg, 0.137 mmol) followed by N-methyl morpholine (200 µL, 1.8 mmol). The reaction mixture was stirred at room temperature for 10 minutes whereupon LCMS analysis demonstrated that the reaction was complete. The mixture was diluted with dimethyl sulfoxide and purified directly by reverse phase chromatography according to a modified version of purification Method A (utilizing gradient elution of 10-100% acetonitrile in water containing 0.02% trifluoroacetic acid over 20 minutes) to afford the title compound #46 (8.0 mg, 56%), as a white solid. LCMS (Protocol A): m/z 1475.0 [M+H]$^+$, retention time=0.94 minutes; HPLC (Protocol B): retention time=6.344 minutes.

Preparation of N²-acetyl-N⁵-{[2-(methylsulfonyl)pyrimidin-5-yl]carbonyl}-L-ornithyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#52)
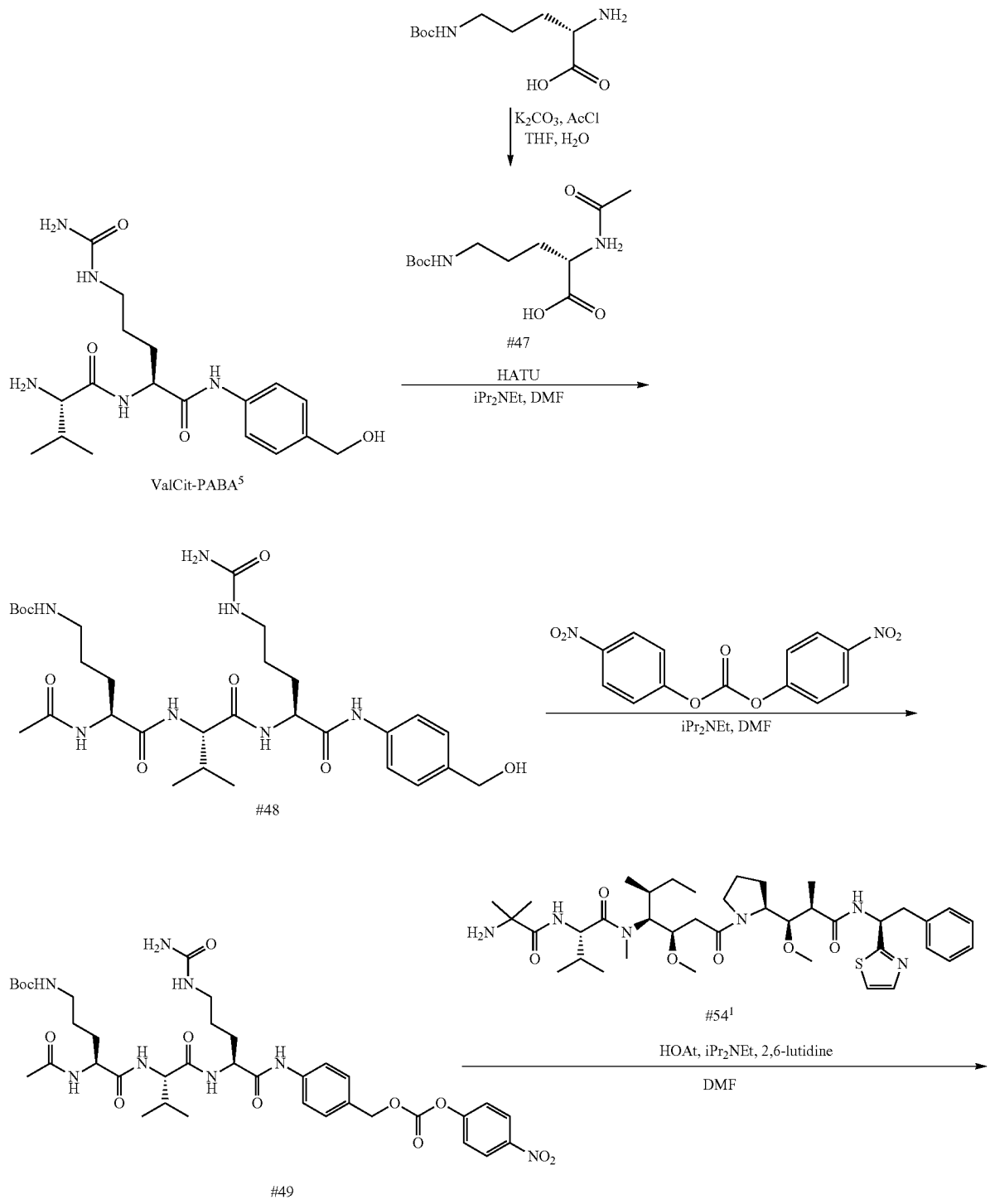

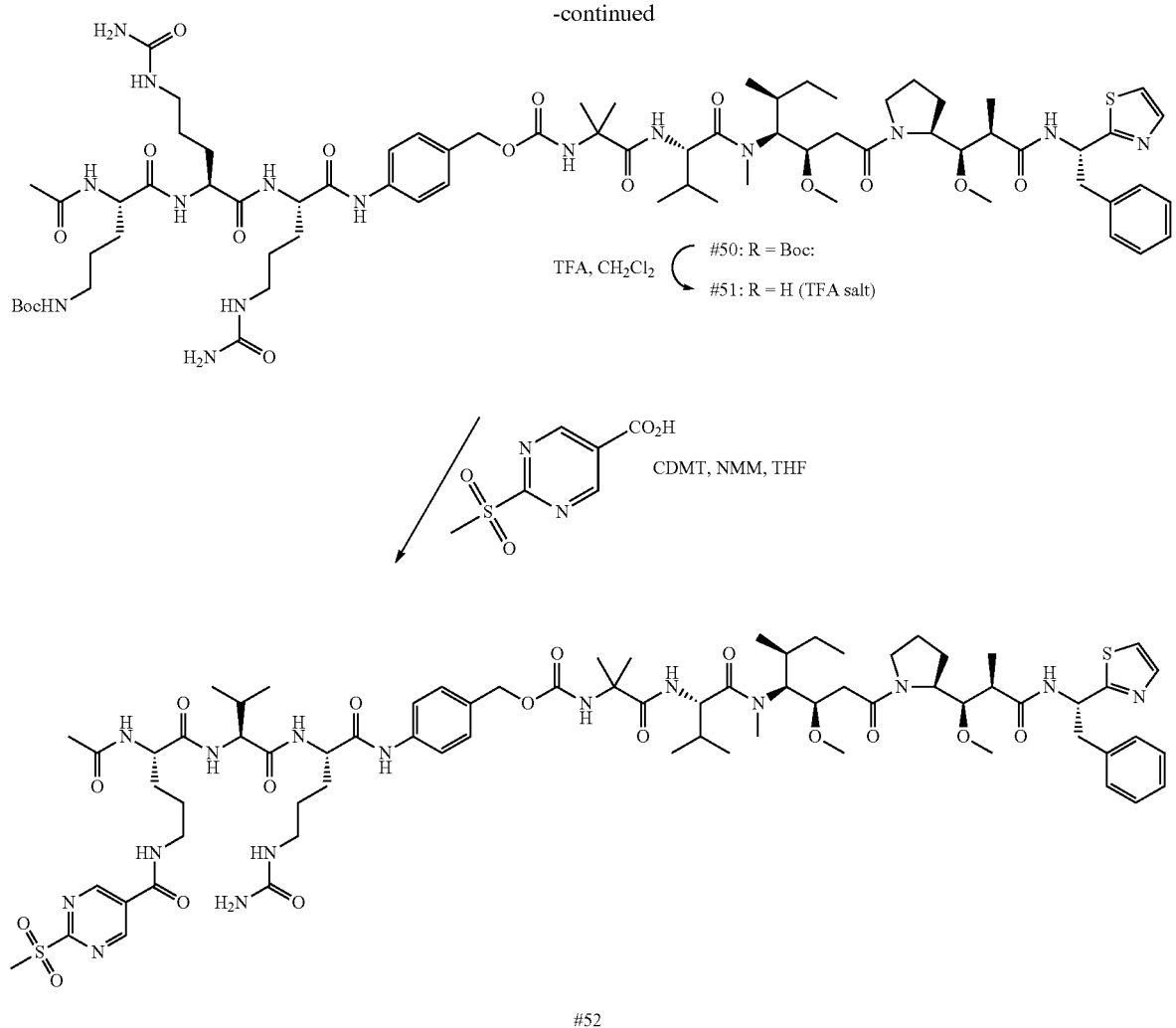

52

Step 1. Synthesis of N²-acetyl-N⁵-(tert-butoxycarbonyl)-L-ornithine (#47) [Ac-Orn(Boc)-OH To a solution of N⁵-(tert-butoxycarbonyl)-L-ornithine, [H-Orn(Boc)-OH] (5.0 g, 21.5 mmol) in THF:water (80:20 mL) was slowly added an aqueous solution of potassium carbonate (11.9 g, 86.1 mmol in 50 mL water). The mixture was stirred for 5 minutes then cooled with an iced water bath before adding dropwise acetyl chloride (3.38 g, 43.1 mmol). The mixture was stirred at room temperature for 2.5 hours upon which TLC (dichloromethane:methanol:acetic acid=100:10:) showed the reaction was complete. The mixture was concentrated under reduced pressure, the resulting aqueous mixture was acidified to pH=2.0 by a 3M aqueous solution of hydrochloric acid, then extracted with ethyl acetate (200 mL×3). The combined organic layers were washed with brine, dried over sodium sulfate, filtered and concentrated to afford the title compound #47 (5.8 g, 98%) as white solid. HPLC (Protocol J): retention time=2.94 minutes. ¹H NMR (400 MHz, DMSO-d6) δ=12.51 (br. s., 1H), 8.10 (d, J=7.5 Hz, 1H), 6.82 (br. s., 1H), 4.13 (d, J=5.0 Hz, 1H), 2.90 (d, J=6.0 Hz, 2H), 1.84 (s, 3H), 1.65 (br. s., 1H), 1.51 (d, J=9.0 Hz, 1H), 1.43-1.35 (m, 11H).

Step 2: Synthesis of N²-acetyl-N⁵-(tert-butoxycarbonyl)-L-ornithyl-L-valyl-N⁵-carbamoyl-N-[4-(hydroxymethyl)phenyl]-L-ornithinamide (#48)

A solution of N²-acetyl-N⁵-(tert-butoxycarbonyl)-L-ornithine #47 [Ac-Orn(Boc)-OH] (875 mg, 3.19 mmol) in anhydrous N,N-dimethylformamide (30 mL) was treated with HATU (1210 mg, 3.19 mmol). After 30 minutes, the mixture was cooled with an iced water bath and L-valyl-N⁵-carbamoyl-N-[4-(hydroxymethyl)phenyl]-L-ornithinamide² [ValCitPABA] (Compound 64 in Dubowchik, G. M. et al. *Bioconjug Chem* 13, 855-69 (2002)⁵ (1100 mg, 2.899 mmol) was added followed by N,N-diisopropylethylamine (1.5 mL, 1113 mg, 8.61 mmol). The mixture was stirred allowed to reach room temperature. After 2 hours, MTBE was added to precipitate the product, which was filtered and dispersed in dichloromethane (150 mL) for 20 min. The mixture was filtered, washed with dichloromethane:methanol (10:1) and then air dried to provide the title compound #48 (1400 mg, 76%) as a grey solid. This material was used directly in subsequent reactions without further purification. HPLC (Protocol J): retention time=3.16 minutes. ¹H NMR (400 MHz, DMSO-d₆) δ=9.96 (s, 1H), 8.12 (d, J=1.0 Hz, 1H), 8.05 (d, J=8.0 Hz, 1H), 7.73 (d, J=8.5 Hz, 1H), 7.55 (d, J=8.5 Hz, 2H), 7.25 (d, J=8.0 Hz, 2H), 6.80 (t, J=5.3 Hz, 1H), 6.00 (t, J=5.3 Hz, 1H), 5.78 (s, 1H), 5.44 (s, 2H), 5.11 (t, J=5.8 Hz, 1H), 4.45 (d, J=1.0 Hz, 1H), 4.42-4.34 (m, J=1.0, 1.0, 1.0 Hz, 1H), 4.32-4.23 (m, 1H), 4.21 (t, J=8.5 Hz, 1H), 3.09-2.85 (m, 4H), 1.99 (qd, J=6.4, 13.4 Hz, 1H), 1.86 (s, 3H), 1.76-1.65 (m, J=9.5 Hz, 1H), 1.64-1.53 (m, J=9.0 Hz, 2H), 1.51-1.43 (m, 2H), 1.43-1.35 (m, 11H), 0.87 (d, J=7.0 Hz, 3H), 0.84 (d, J=6.5 Hz, 3H).

Step 3: Synthesis of $N^2$-acetyl-$N^5$-(tert-butoxycarbonyl)-L-ornithyl-L-valyl-$N^5$-carbamoyl-N-[4-({[(4-nitrophenoxy)carbonyl]oxy}methyl)phenyl]-L-ornithinamide (#49)

In iced water bath, a solution of $N^2$-acetyl-$N^5$-(tert-butoxycarbonyl)-L-ornithyl-L-valyl-$N^5$-carbamoyl-N-[4-(hydroxymethyl)phenyl]-L-ornithinamide, #48 (1400 mg, 2.202 mmol) and in anhydrous N,N-dimethylformamide (25 mL) was treated with bis-(4-nitrophenyl)carbonate (1.34 g, 4.40 mmol) with N,N-diisopropylethylamine (767 μL, 569 mg, 4.40 mmol) and the reaction was stirred at room temperature for 6 hours. The reaction mixture was poured into MTBE and after 20 minutes the solid was isolated by filtration, washed with dichloromethane (150 mL) then air dried to provide the title compound #49 (1.3 g, 74%) as a white solid. This material was used directly in subsequent reactions without further purification. LCMS (Protocol K): m/z 801.3 [M+H]$^+$, m/z 823.3 [M+Na]$^+$ retention time=4.066 minutes; HPLC (Protocol J): retention time=2.63 minutes. 1H NMR (400 MHz, DMSO-d6) d=10.21-10.02 (m, 1H), 8.39-8.27 (m, 2H), 8.20-7.95 (m, 2H), 7.76-7.53 (m, 5H), 7.42 (d, J=8.0 Hz, 2H), 6.84-6.72 (m, 1H), 6.07-5.92 (m, 1H), 5.48-5.39 (m, 2H), 5.29-5.20 (m, 2H), 4.47-4.10 (m, 3H), 3.06-2.81 (m, 4H), 2.10-1.92 (m, 1H), 1.91-1.79 (m, 3H), 1.76-1.53 (m, 3H), 1.37 (br. s., 14H), 0.94-0.74 (m, 6H)

Step 4: Synthesis of $N^2$-acetyl-$N^5$-(tert-butoxycarbonyl)-L-ornithyl-$N^5$-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#50)

To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (Example #54 in US 2013/0129753 A1) [Aur-0101] (113 mg, 0.152 mmol) in N,N-dimethylacetamide (4 mL) were added $N^2$-acetyl-$N^5$-(tert-butoxycarbonyl)-L-ornithyl-L-valyl-$N^5$-carbamoyl-N-[4-({[(4-nitrophenoxy)carbonyl]oxy}methyl)phenyl]-L-ornithinamide, #49 (124.5 mg, 0.155 mmol), HOAt (24 mg, 0.18 mmol), 2,6-Lutidine (44.3 μL, 41 mg, 0.38 mmol), and N,N-diisopropylethylamine (66.9 μL, 50 mg, 0.38 mmol). The orange reaction mixture was heated at 45° C. overnight. LCMS analysis indicated that the reaction was complete. The mixture was diluted with dimethyl sulfoxide and purified by reverse phase chromatography according to a modified version of purification Method A (utilizing gradient elution of 20-100% acetonitrile in water containing 0.02% trifluoroacetic acid over 20 minutes) to provide the desired product #50 (82.2 mg, 38%) as white solid. LCMS (Protocol C): m/z 1405.9 [M+H]$^+$, retention time=0.95 minutes. HPLC (Protocol B): retention time=6.735 minutes.

Step 5: Synthesis of $N^2$-acetyl-L-ornithyl-$N^5$-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, trifluoroacetic salt (#51)

Trifluoroacetic acid (1 mL, 10 mmol) was added to a solution of $N^2$-acetyl-$N^5$-(tert-butoxycarbonyl)-L-ornithyl-$N^5$-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, #50 (82.2 mg, 0.0585 mmol) in acetonitrile (2 mL), and the reaction was allowed to stir at room temperature for 15 minutes. The reaction was concentrated under reduced pressure to provide the title compound #51 (90 mg), as a white solid that was used directly without further purification. LCMS (Protocol E): m/z 1304.9 [M+H]$^+$, retention time=0.81 minutes; HPLC (Protocol B): retention time=5.804 minutes.

Step 6: Synthesis of $N^2$-acetyl-$N^5$-{[2-(methylsulfonyl)pyrimidin-5-yl]carbonyl}-L-ornithyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide (#52)

To a solution the trifluoroacetic acid salt of $N^2$-acetyl-L-ornithyl-$N^5$-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-$N^5$-carbamoyl-L-ornithinamide, #51 (88.0 mg, 0.067 mmol) in N,N-dimethylacetamide (0.5 mL) were added of 2-(methylsulfonyl)pyrimidine-5-carboxylic acid (68.2 mg, 0.337 mmol) and 2-chloro-4,6-dimethoxy-1,3,5-triazine (59.2 mg, 0.337 mmol) followed by N-methyl morpholine (74 μL, 68.2 mg, 0.675 mmol). The orange reaction mixture was stirred at room temperature for 90 minutes whereupon LCMS analysis demonstrated that the reaction was complete. The mixture was diluted with dimethyl sulfoxide and purified directly by reverse phase chromatography according to a modified version of purification Method A (utilizing gradient elution of 10-80% acetonitrile in water containing 0.02% trifluoroacetic acid over 20 minutes) to afford the title compound #52 (98.4 mg, 98%), as a white solid. LCMS (Protocol A): m/z 1489.8 [M+H]$^+$, retention time=0.92 minutes; HPLC (Protocol B): retention time=6.342 minutes.

Preparation of N²-acetyl-N⁶-{[2-(methylsulfonyl)pyrimidin-5-yl]carbonyl}-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#58)
Scheme for Compound #58
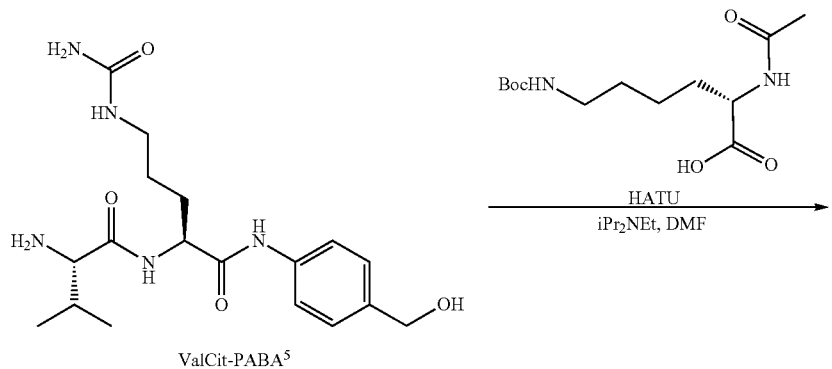
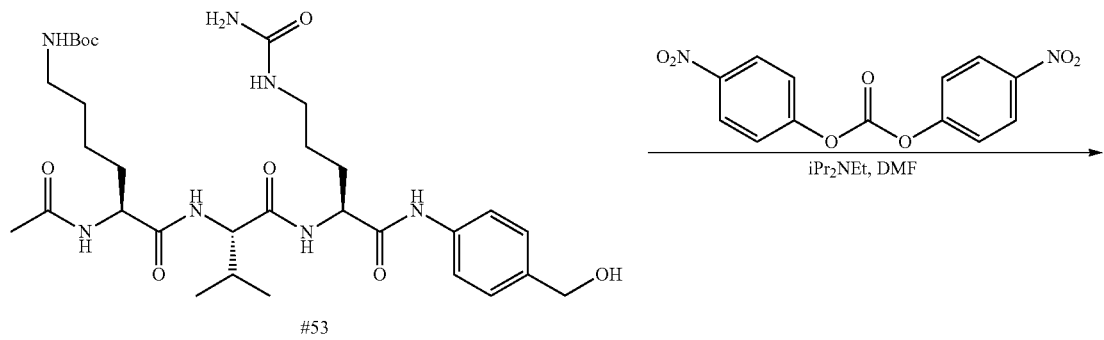
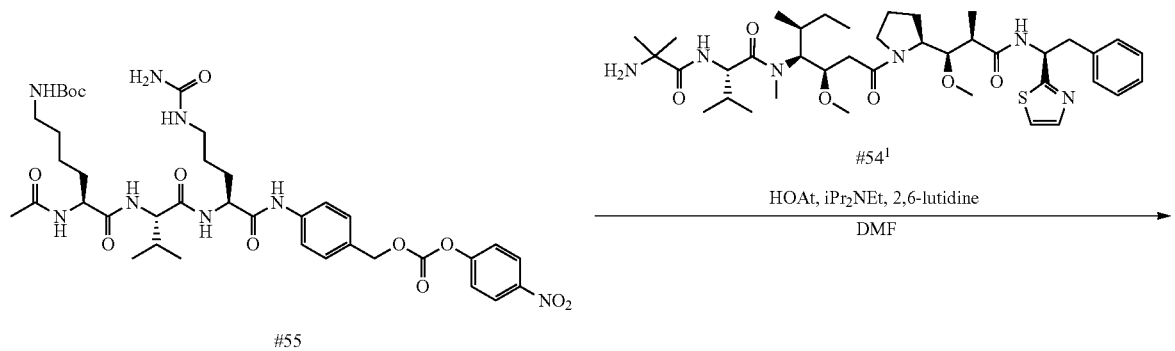

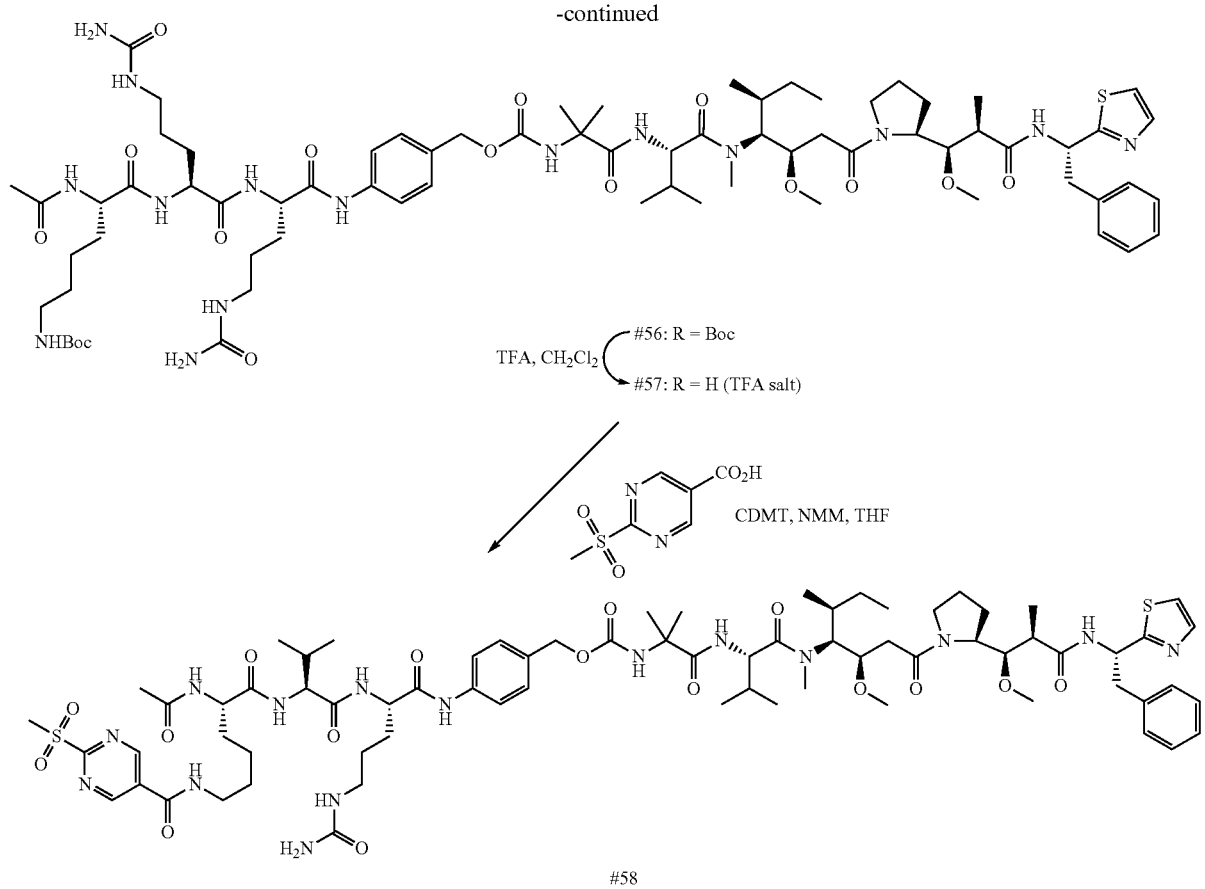

Step 1: Synthesis of $N^2$-acetyl-$N^6$-(tert-butoxycarbonyl)-L-lysyl-L-valyl-$N^5$-carbamoyl-N-[4-(hydroxymethyl)phenyl]-L-ornithinamide (#53)

In an iced water bath, a solution of Ac-Lys(Boc)-OH (15.2 g, 52.7 mmol) in anhydrous N,N-dimethylformamide (250 mL) was treated with HATU (20.0 g, 52.7 mmol). After 30 minutes, L-valyl-$N^5$-carbamoyl-N-[4-(hydroxymethyl)phenyl]-L-ornithinamide[2] (Compound 64 in Dubowchik, G. M. et al. *Bioconjug Chem* 13, 855-69 (2002))[5] (20 g, 52.7 mmol) was added followed by N,N-diisopropylethylamine (12.8 mL, 9.54 g, 73.8 mmol). The mixture was allowed to reach room temperature. After 2 hours, the reaction mixture was poured in MTBE to precipitate the product, which was filtered and dispersed in dichloromethane:methanol (10:1, 800 mL) for 20 minutes. The mixture was filtered, air dried and purified by prep-HPLC according to Method D. After concentration under reduced pressure, the residue was poured in chloroform:isopropyl alcohol 4:1. The solid was collected by filtration and air dried to provide the title compound #53 (15.0 g, 44%) as a white solid. HPLC (Protocol J): retention time=3.63 minutes. $^1$H NMR (400 MHz, DMSO-$d_6$) δ=9.95 (s, 1H), 8.32 (s, 1H), 8.09 (d, J=7.5 Hz, 1H), 8.03 (d, J=8.0 Hz, 1H), 7.72 (d, J=9.0 Hz, 1H), 7.57-7.51 (m, J=8.5 Hz, 2H), 7.27-7.20 (m, J=8.5 Hz, 2H), 6.77 (t, J=5.5 Hz, 1H), 5.98 (t, J=5.8 Hz, 1H), 5.43 (s, 2H), 5.11 (t, J=5.5 Hz, 1H), 4.43 (d, J=5.5 Hz, 2H), 4.41-4.35 (m, 1H), 4.29-4.21 (m, 1H), 4.19 (dd, J=7.0, 8.5 Hz, 1H), 3.07-2.92 (m, 2H), 2.91-2.84 (m, 2H), 2.34 (s, 1H), 1.98 (qd, J=6.7, 13.6 Hz, 1H), 1.84 (s, 3H), 1.72-1.50 (m, 3H), 1.43-1.33 (m, 12H), 1.25 (dd, J=10.3, 15.8 Hz, 3H), 0.86 (d, J=6.5 Hz, 3H), 0.83 (d, J=6.5 Hz, 3H).

Step 2: Synthesis $N^2$-acetyl-$N^6$-(tert-butoxycarbonyl)-L-lysyl-L-valyl-$N^5$-carbamoyl-N-[4-({[(4-nitrophenoxy)carbonyl]oxy}methyl)phenyl]-L-ornithinamide (#55)

In an iced water bath, to a solution of $N^2$-acetyl-$N^6$-(tert-butoxycarbonyl)-L-lysyl-L-valyl-$N^5$-carbamoyl-N-[4-(hydroxymethyl)phenyl]-L-ornithinamide, #53 (12.0 g, 18.5 mmol) and in anhydrous N,N-dimethylformamide (150 mL) was treated with bis-(4-nitrophenyl)carbonate (11.2 g, 36.9 mmol) with N,N-diisopropylethylamine (6.42 mL, 4.77 g, 36.9 mmol) and the reaction was stirred at room temperature for 3 hours. The reaction mixture was poured into MTBE and after 20 minutes the solid was isolated by filtration, washed with dichloromethane (1 L) then air dried to provide the title compound #55 (12.5 g, 83.1%) as a yellow solid. This material was used directly in subsequent reactions without further purification. LCMS (Protocol K): m/z 815.2 [M+H]$^+$, retention time=4.101 minutes; HPLC (Protocol J): retention time=4.58 minutes. $^1$H NMR (400 MHz, DMSO-$d_6$) δ=10.12 (s, 1H), 8.35-8.29 (m, J=9.0 Hz, 2H), 8.13 (d, J=7.0 Hz, 1H), 8.03 (d, J=7.5 Hz, 1H), 7.74-7.62 (m, 3H), 7.60-7.55 (m, J=9.0 Hz, 2H), 7.42 (d, J=8.5 Hz, 2H), 6.77 (br. s., 1H), 6.03-5.96 (m, 1H), 5.44 (s, 2H), 5.25 (s, 2H), 4.44-4.35 (m, 1H), 4.29-4.16 (m, 2H), 3.09-2.84 (m, 5H), 2.74 (s, 1H), 2.04-1.91 (m, 1H), 1.85 (s, 3H), 1.69 (br. s., 1H), 1.60 (d, J=9.0 Hz, 2H), 1.46 (br. s., 2H), 1.37 (s, 12H), 1.24 (br. s., 2H), 1.11 (s, 2H), 0.86 (d, J=7.0 Hz, 3H), 0.83 (d, J=6.5 Hz, 3H).

Step 3: Synthesis of N²-acetyl-N⁶-(tert-butoxycarbonyl)-L-lysyl-N⁵-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1i) -2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#56)

To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (Example #54 in US 2013/0129753 A1) (88 mg, 0.12 mmol) in N,N-dimethylacetamide (1 mL) were added AcLys(Boc)ValCitPABC-PNP, #55 (100 mg, 0.123 mmol), HOAt (17.2 mg, 0.126 mmol), 2,6-Lutidine (34.8 µL, 32 mg, 0.30 mmol), and N,N-diisopropylethylamine (52.6 µL, 39 mg, 0.30 mmol). The orange reaction mixture was heated at 45° C. overnight. LCMS analysis indicated that the reaction was complete. The mixture was diluted with dimethyl sulfoxide and purified by reverse phase chromatography according to a modified version of purification Method A (utilizing gradient elution of 20-100% acetonitrile in water containing 0.02% trifluoracetic acid over 20 minutes) to provide the desired product #56 (85.2 mg, 51%) as white solid. LCMS (Protocol C): m/z 1419.9 [M+H]⁺, 1442.9 [M+Na]⁺ retention time=0.97 minutes. HPLC (Protocol B): retention time=6.836 minutes.

Step 4: Synthesis of N²-acetyl-L-lysyl-N⁵-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide, trifluoroacetic salt (#57

Trifluoroacetic acid (1 mL, 10 mmol) was added to a solution of N²-acetyl-N⁶-(tert-butoxycarbonyl)-L-lysyl-N⁵-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1i)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide, #56 (85.2 mg, 0.0601 mmol) in acetonitrile (2 mL), and the reaction was allowed to stir at room temperature for 15 minutes. The reaction was concentrated under reduced pressure to provide the title compound #57 (90 mg), as a white solid that was used directly without further purification. LCMS (Protocol E): m/z 1318.9 [M+H]⁺, retention time=0.81 minutes; HPLC (Protocol B): retention time=5.813 minutes.

Step 5: Synthesis of N²-acetyl-N⁶-{[2-(methylsulfonyl)pyrimidin-5-yl]carbonyl}-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide (#58)

To a solution the trifluoroacetic acid salt of N²-acetyl-L-lysyl-N⁵-carbamoyl-L-ornithyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N⁵-carbamoyl-L-ornithinamide, #57 (90.0 mg, 0.068 mmol) in N,N-dimethylacetamide (0.5 mL) were added of 2-(methylsulfonyl)pyrimidine-5-carboxylic acid (69.0 mg, 0.341 mmol) and 2-chloro-4,6-dimethoxy-1,3,5-triazine (59.9 mg, 0.341 mmol) followed by N-methyl morpholine (200 µL, 180 mg, 1.8 mmol). The orange reaction mixture was stirred at room temperature for 90 minutes whereupon LCMS analysis demonstrated that the reaction was complete. The mixture was diluted with dimethyl sulfoxide and purified directly by reverse phase chromatography according to a modified version of purification Method A (utilizing a modified gradient elution of 10-80% acetonitrile in water containing 0.02% trifluoroacetic acid over 20 minutes) to afford the title compound #58 (91.7 mg, 89%), as a white solid. LCMS (Protocol A): m/z 1503.8 [M+H]⁺, retention time=0.92 minutes; HPLC (Protocol B): retention time=6.360 minutes.

Preparation of N-({[4-(beta-D-glucopyranuronosyloxy)-3-({N-[6-({[2-(methylsulfonyl)pyrimidin-5-yl]carbonyl}amino)hexanoyl]-beta-alanyl}amino)benzyl]oxy}carbonyl)-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#66

Scheme for Compound #66

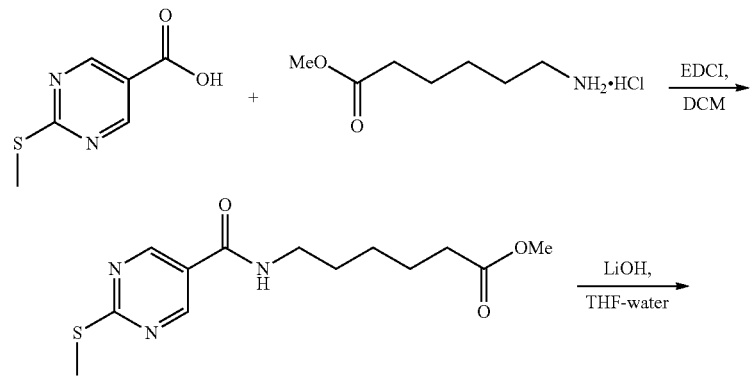

59

-continued
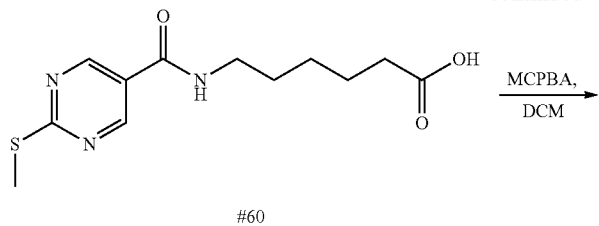
60
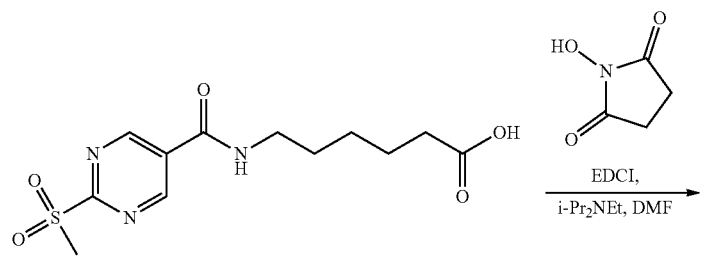
61
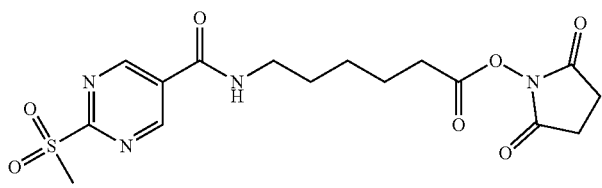
62
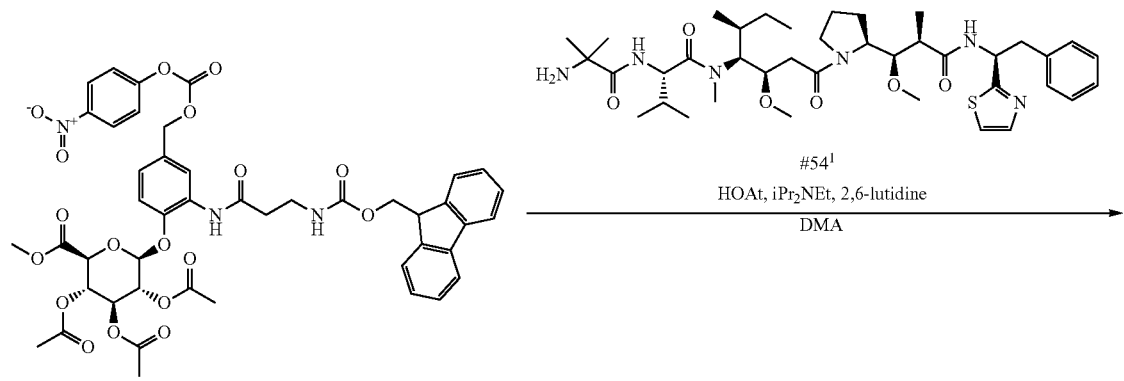
63ˣ

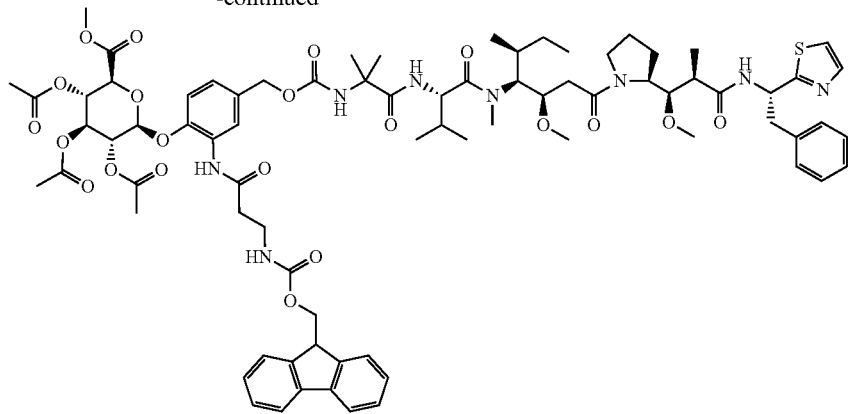

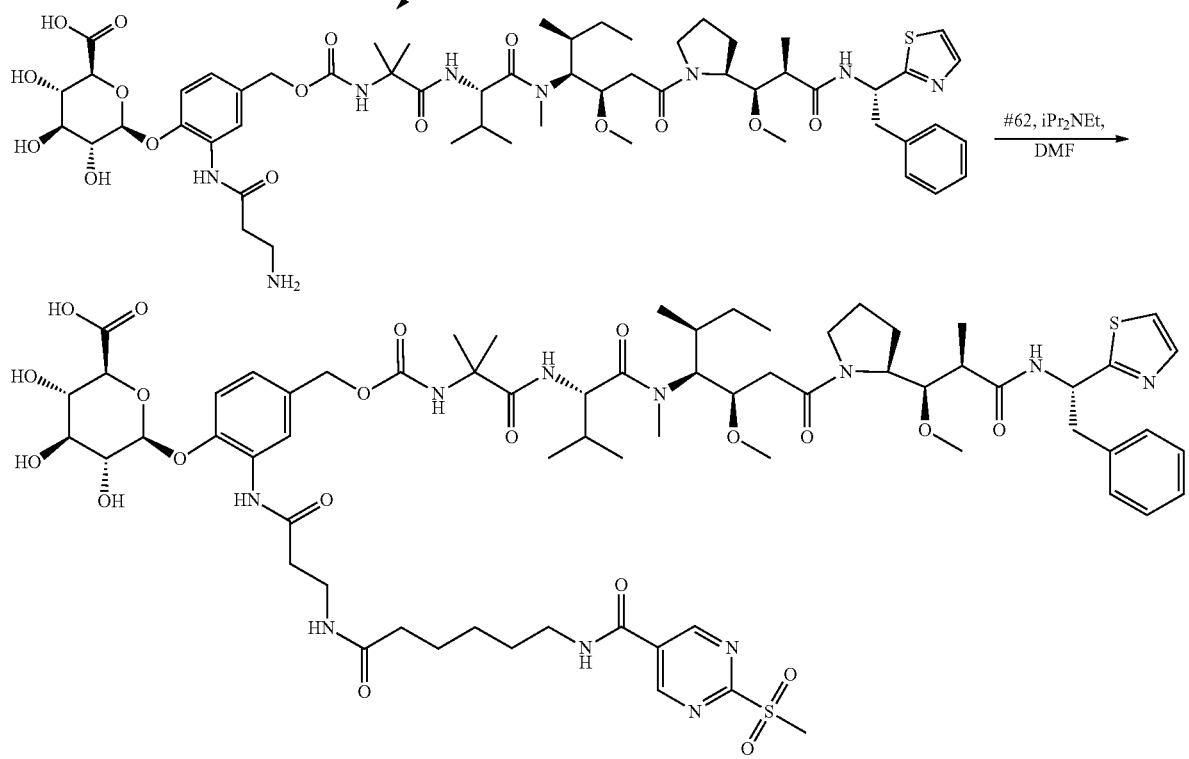

Step 1. Synthesis of methyl 6-({[2-(methylsulfanyl) pyrimidin-5-yl]carbonyl}amino)hexanoate (#59)

To a solution of 2-(methylsulfanyl)pyrimidine-5-carboxylic acid (Example 29 in US2010/210593 A1; Yu-Xiu, Liu; Ming-Bo, Cui; Qi-Qi, Zhao; Qing-Min, Wang; Ying, Liu; Run-Qiu, Huang, Reduction of pyrimidine derivatives by LiAlH₄ *Journal of Chemical Research,* 2007, #8 p. 490-493) (228 mg, 1.34 mmol) and methyl 6-aminohexanoate hydrochloride (497 mg, 2.68 mmol) in dichloromethane (6 mL) were added 1-ethyl-3-(3-dimethylaminopropyl)carbodiimide (68 mg, 0.36 mmol) and N,N-diisopropylethylamine (0.5 mL, 3 mmol). The reaction was allowed to stir for 18 hours at room temperature. The reaction was concentrated under reduced pressure and purified by silica gel chromatography (Gradient: 20%-100% ethyl acetate in heptanes) to provide methyl 6-({[2-(methylsulfanyl)pyrimidin-5-yl]carbonyl}amino)hexanoate, #59 (131 mg, 33%), as a white solid. LCMS (Protocol E): m/z 298.4 [M+H]⁺, retention time=1.21 minutes; ¹H NMR (500 MHz, DMSO-d₆): δ ¹H NMR (500 MHz, DMSO-d₆) δ=8.97 (s, 2H), 8.67 (t, J=5.4 Hz, 1H), 3.58 (s, 3H), 3.33 (s, 2H), 3.29-3.23 (m, 2H), 2.57 (s, 3H), 2.32 (t, J=7.5 Hz, 2H), 1.54 (dquin, 4H), 1.36-1.28 (m, 2H).

Step 2. Synthesis of 6-({[2-(methylsulfanyl)pyrimidin-5-yl]carbonyl}amino)hexanoic acid (#60)

To a solution of methyl methyl 6-({[2-(methylsulfanyl)pyrimidin-5-yl]carbonyl}amino)hexanoate, #59 (63 mg, 0.21 mmol), in tetrahydrofuran (1 mL) was added a solution of lithium hydroxide (21 mg, 0.86 mmol) in water (0.3 mL). After 3 hours, the reaction was diluted with dichloromethane and acidified to pH=2 with 1N hydrochloride acid. The aqueous layer was back-extracted with dichloromethane. The organic layer was dried over anhydrous sodium sulfate, filtered and concentrated in vacuo to provide 6-({[2-(methylsulfanyl)pyrimidin-5-yl]carbonyl}amino)hexanoic acid, #60 (53 mg, 88%), as a white solid, which was used in the next step without further purification. LCMS (Protocol A): m/z 284.19 [M+H]$^+$, retention time=0.93 minutes; $^1$H NMR (500 MHz, DMSO-d$_6$): δ 11.99 (s, 1H), 8.97 (s, 2H), 8.67 (t, J=5.5 Hz, 1H), 3.29-3.17 (m, 2H), 2.57 (s, 3H), 2.22 (t, J=7.3 Hz, 2H), 1.53 (quin, J=7.4 Hz, 4H), 1.39-1.24 (m, 2H).

Step 3. Synthesis of 6-({[2-(methylsulfonyl)pyrimidin-5-yl]carbonyl}amino)hexanoic acid (#61)

To a suspension of 6-({[2-(methylsulfanyl)pyrimidin-5-yl]carbonyl}amino)hexanoic acid, #60 (146 mg, 0.515 mmol) in dichloromethane (2 mL) was added m-chloroperoxybenzoic acid (272 mg, 1.55 mmol). The reaction was allowed to stir for 3 hours at room temperature. The reaction was filtered and the solid collected to provide 6-({[2-(methylsulfonyl)pyrimidin-5-yl]carbonyl}amino)hexanoic acid, #61 (58 mg, 36%) as a yellow solid, which was used in the next step without further purification. LCMS (Protocol E): m/z 338.3 [M+Na]$^+$, 314.4 [M−H]$^+$, retention time=0.57 minutes; $^1$H NMR (500 MHz, DMSO-d$_6$) δ 9.36 (d, J=1.6 Hz, 1 H) 9.25 (d, J=1.6 Hz, 1 H) 9.13 (br. s., 1 H) 3.43-3.50 (m, 2 H) 3.33 (s, 3 H) 2.31 (t, J=7.4 Hz, 2 H) 1.62-1.73 (m, 4 H) 1.38-1.49 (m, 2 H).

Step 4. Synthesis of N-{6-[(2,5-dioxopyrrolidin-1-yl)oxy]-6-oxohexyl}-2-(methylsulfonyl)pyrimidine-5-carboxamide (#62)

To a solution of 6-({[2-(methylsulfonyl)pyrimidin-5-yl]carbonyl}amino)hexanoic acid, #61 (14.2 mg, 0.045 mmol) and N-hydroxysuccimide (5.6 mg, 0.049 mmol) in dichloromethane (1 mL) were added 1-ethyl-3-(3-dimethylaminopropyl)carbodiimide (8.6 mg, 0.045 mmol) and N,N-diisopropylethylamine (0.5 mL, 3 mmol). The reaction was allowed to stir for 72 hours at room temperature. The mixture was diluted with dimethyl sulfoxide and purified directly by reverse phase chromatography according to a modified version of purification Method A (utilizing gradient elution of 10-90% acetonitrile in water containing 0.02% acetic acid over 20 minutes) to afford the title compound (9.2 mg, 50%), as a white solid. LCMS (Protocol E): m/z 413.3 [M+H]$^+$, retention time=0.65 minutes.

Step 5. Synthesis of N-[({3-({N-[(9H-fluoren-9-ylmethoxy)carbonyl]-beta-alanyl}amino)-4-[(2,3 4-tri-O-acetyl-6-methyl-beta-D-glucopyranuronosyl)oxy]benzyl}oxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#64)

To a mixture of 2-({N-[(9H-fluoren-9-ylmethoxy)carbonyl]-beta-alanyl}amino)-4-({[(4-nitrophenoxy)carbonyl]oxy}methyl)phenylmethyl-2,3,4-tri-O-acetyl-beta-D-glucopyranosiduronate, #63 (Compound 7 in WO2007/11968 A2) (585 mg, 0.54 mmol) and 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (Example #54 in US 2013/0129753 A1) (105 mg, 0.141 mmol) (412.0 mg, 0.554 mmol) in N,N-dimethylacetamide (5 mL) were added HOAt (85 mg, 0.62 mmol), 2,6-Lutidine (216 μL, 200 mg, 0.1.9 mmol), and N,N-diisopropylethylamine (327 μL, 250 mg, 1.9 mmol). The orange reaction mixture was heated at 45° C. for 1.5 hours then stirred at room temperature overnight. LCMS analysis indicated that the reaction was complete. The mixture was diluted with dimethyl sulfoxide and purified by reverse phase chromatography according to a modified version of purification Method A (utilizing gradient elution of 30-100% acetonitrile in water containing 0.02% trifluoracetic acid over 20 minutes) to provide the desired product #64 (307.9 mg, 37%) as white solid. LCMS (Protocol C): m/z 1519.0 [M+H]$^+$, retention time=1.09 minutes. HPLC (Protocol B): retention time=8.559 minutes.

Step 6. Synthesis of N-({[3-(beta-alanylamino)-4-(beta-D-glucopyranuronosyloxy)benzyl]oxy}carbonyl)-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, acetic acid salt (#65)

In an iced water bath, to a solution of N-[({3-({N-[(9H-fluoren-9-ylmethoxy)carbonyl]-beta-alanyl}amino)-4-[(2,3,4-tri-O-acetyl-6-methyl-beta-D-glucopyranuronosyl)oxy]benzyl}oxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide, #64 (119.0 mg, 0.0784 mmol) in N,N-dimethylacetamide (2 mL) was added an aqueous solution of lithium hydroxide (461 μL, 46.1 mg, 1.10 mmol). After 10 minutes, LCMS analysis demonstrated that the reaction was complete and was then neutralized with acetic acid, diluted with dimethyl sulfoxide and methanol and purified directly by reverse phase chromatography according to a modified version of purification Method A (utilizing gradient elution of 15-70% acetonitrile in water containing 0.02% acetic acid over 20 minutes) to afford the title compound #65 (34.8 mg, 36.5%), as a white solid. LCMS (Protocol A): m/z 1155.9 [M+H]$^+$, retention time=0.73 minutes; HPLC (Protocol B): retention time=5.532 minutes.

Step 7. Synthesis of N-({[4-(beta-D-glucopyranuronosyloxy)-3-({N-[6-({[2-(methylsulfonyl)pyrimidin-5-yl]carbonyl}amino)hexanoyl]-beta-alanyl}amino)benzyl]oxy}carbonyl)-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#66)

To a solution of N-({[3-(beta-alanylamino)-4-(beta-D-glucopyranuronosyloxy)benzyl]oxy}carbonyl)-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol- 2-yl)ethyl]amino}propyl]pyrrolidin-1-yl}-5-methyl-1-oxoheptan-4-yl]-N-methyl-L-valinamide, acetic acid salt, #65 (26.0 mg, 0.019 mmol) and N-{6-[(2,5-dioxopyrrolidin-1-yl)oxy]-6-oxohexyl}-2-(methylsulfonyl) pyrimidine-5-carboxamide, #62 (9.2 mg, 0.022 mmol) in N,N-dimethylformamide (1 mL) was added N,N-diisopropylethylamine (30 µL, 22 mg, 0.17 mmol). The reaction was allowed to stir for 1.5 hours at room temperature. The crude reaction mixture was diluted with dimethyl sulfoxide and directly purified by reverse phase HPLC according to a modified version of purification Method A (utilizing gradient elution of 15-90% acetonitrile in water containing 0.02% trifluoroacetic acid over 20 minutes) to afford the title compound #66 (3.7 mg, 13.5%), as a white solid. LCMS (Protocol E): m/z 1453.4 [M+H$^+$], retention time=0.84 minutes; HPLC (Protocol B): retention time=6.225 minutes.

Step 1. Synthesis of tert-butyl [16-(11,12-didehydrodibenzo[b,f]azocin-5(6H)-yl)-13,16-dioxo-3,6,9-trioxa-12-azahexadec-1-yl]carbamate (#67)

A solution of 1-{[4-(11,12-didehydrodibenzo[b,f]azocin-5(6H)-yl)-4-oxobutanoyl]oxy}pyrrolidine-2,5-dione (0.10 g, 0.25 mmol) and tert-butyl (2-{2-[2-(2-aminoethoxy)ethoxy]ethoxy}ethyl)carbamate (0.073 g, 0.25 mmol) in dichloromethane (5 mL) was treated with N,N-diisopropylethylamine (0.05 mL, 0.3 mmol) and the solution was stirred at room temperature. After ~1 hour the reaction was concentrated and purified over 12 g of silica gel, eluted with 0-20% methanol in dichloromethane over 25 minutes. Product containing fractions were combined and concentrated to Scheme for Compound #69

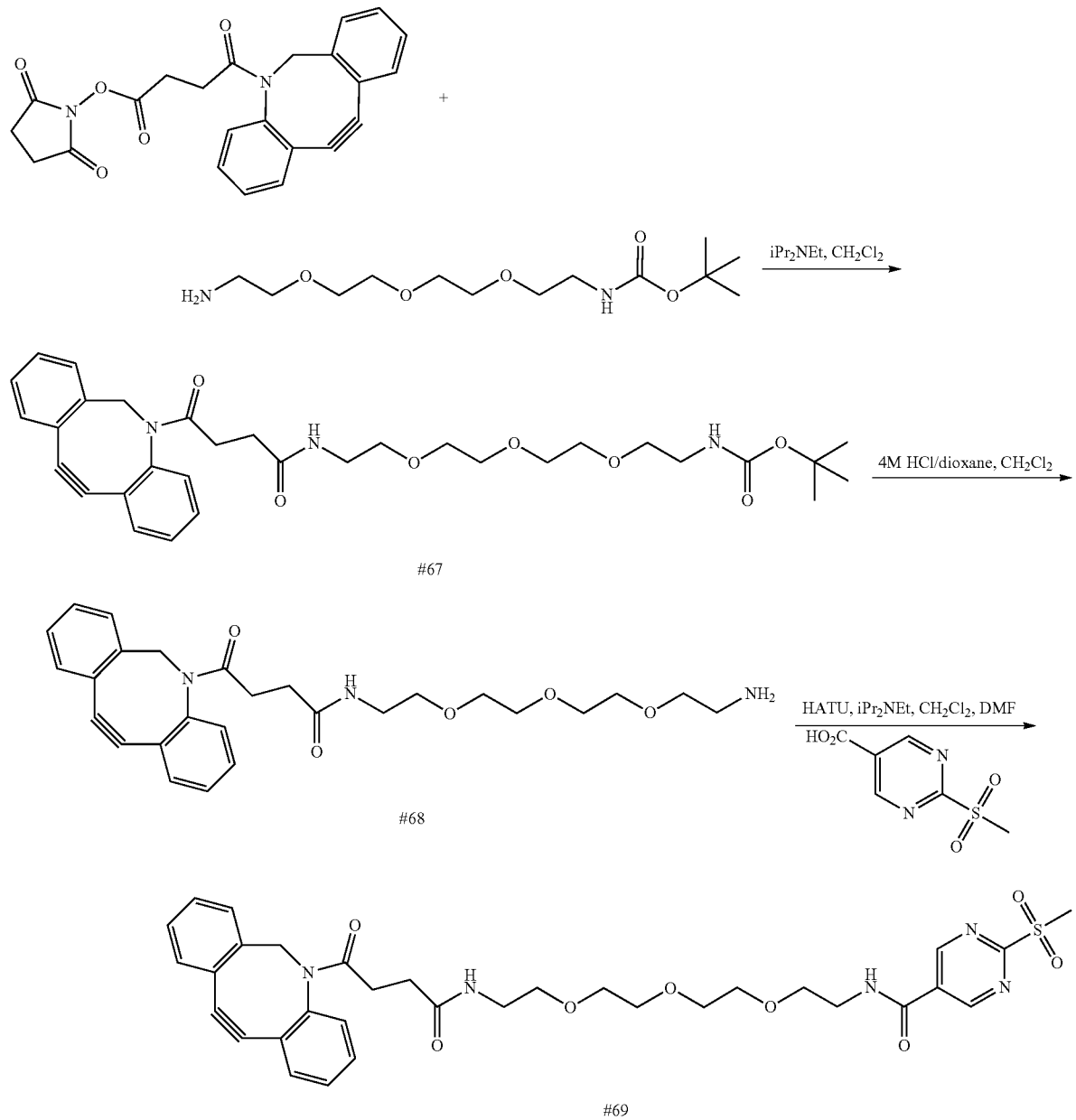

give the desired compound, #67, (0.12 g, 83%) as a colorless oil. LCMS (Protocol P): m/z 580.5 [M+H]$^+$, retention time=1.75 minutes Step 2. Synthesis N-(2-{2-[2-(2-aminoethoxy)ethoxy]ethyl}-4-(11,12-didehydrodibenzo[b,f]azocin-5(6H)-yl)-4-oxobutanamide (#68)

A solution of tert-butyl [16-(11,12-didehydrodibenzo[b,f]azocin-5(6H)-yl)-13,16-dioxo-3,6,9-trioxa-12-azahexadec-1-yl]carbamate (0.119 g, 0.205 mmol) in dichloromethane (5 mL) was treated with a 4 M HCl/dioxane solution (1 mL, 4 mmol) and the reaction was stirred at room temperature. After ~30 minutes the reaction was concentrated and the residue was purified over 4 g of silica gel, eluted with 0-100% Methanol in dichloromethane over 25 minutes. Product containing fractions were combined and concentrated to give the desired compound, #68, (0.084 g, 79%) as viscous oil. LCMS (Protocol O): m/z 480.4 [M+H]$^+$, retention time=0.63 minutes Step 3. Synthesis N-[16-(11,12-didehydrodibenzo[b,f]azocin-5(6H)-yl)-13,16-dioxo-3,6,9-trioxa-12-azahexadec-1-yl]-2-(methylsulfonyl)pyrimidine-5-carboxamide (#69)

A solution of 2-(methylsulfonyl)pyrimidine-5-carboxylic acid (0.032 g, 0.16 mmol) in dichloromethane (3 mL) was treated with HATU (0.060 g, 0.16 mmol) and N,N-diisopropylethylamine DIEA (0.05 mL, 0.31 mmol). After ~3 minutes, a solution of N-(2-{2-[2-(2-aminoethoxy)ethoxy]ethyl}-4-(11,12-didehydrodibenzo[b,f]azocin-5(6H)-yl)-4-oxobutanamide (0.080 g, 0.16 mmol) in dichloromethane (2 mL) was added and the reaction was stirred at room temperature. After ~1.5-2 hours, the reaction was concentrated and the residue was purified over 12 g of silica gel, eluted with 0-20% methanol in dichloromethane over 25 minutes. Product containing fractions were combined and concentrated to provide the desired compound, #69, (0.070 g, 68%) as an oil. LCMS (Protocol P): m/z 664.5 [M+H]$^+$, retention time=1.46 minutes.

Scheme for Compound #73

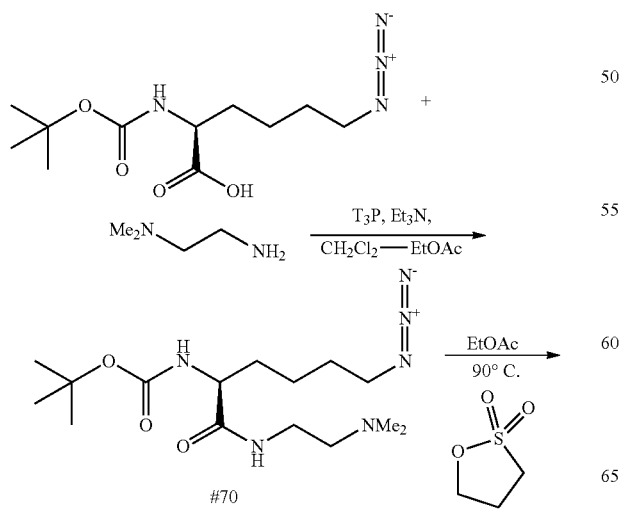

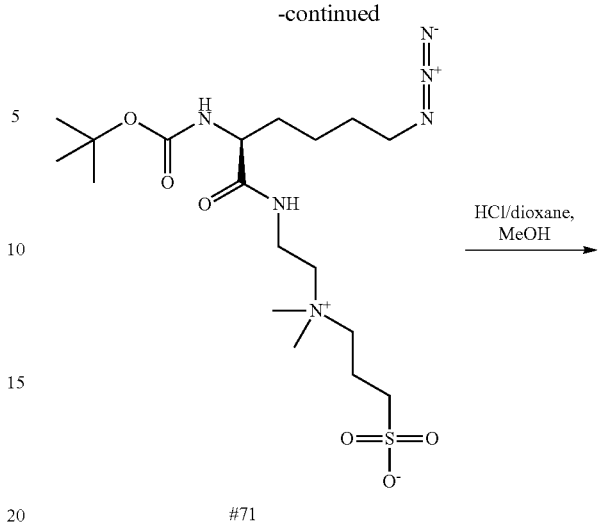

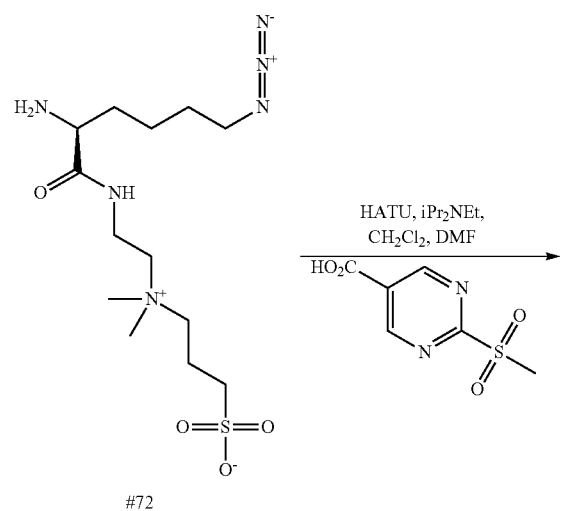

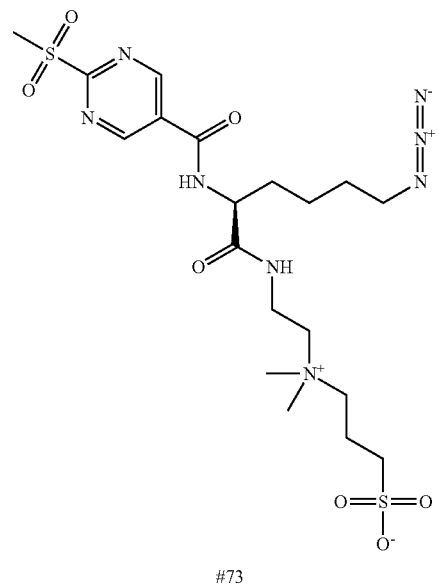 [SMILES: C[N+](C)(CCCS(=O)(=O)[O-])CCNC(=O)[C@H](CCCCN=[N+]=[N-])NC(=O)c1cnc(S(C)(=O)=O)nc1]

Step 1. Synthesis of 6-azido-N²-(tert-butoxycarbonyl)-N-[2-(dimethylamino)ethyl]-L-norleucinamide (#70)

To a solution of 6-azido-N-(tert-butoxycarbonyl)-L-norleucine (4.9 g, 18 mmol) in anhydrous dichloromethane (80 mL) at 0° C. was added triethylamine (17.2 mL, 126 mmol) followed by T3P (16.6 mL, 27.9 mmol, 50% in EtOAc) and the mixture was stirred at 0° C. for 30 min. A solution of N,N-dimethylethane-1,2-diamine (2.38 g, 27.0 mmol) in anhydrous dichloromethane (20 mL) was added and the mixture was stirred at 0° C. and allowed to warm to 15° C. overnight. The mixture was then quenched with saturated aqueous NaHCO₃ and extracted with dichloromethane (3×100 mL). Combined organic extracts were washed with saturated aqueous NaHCO₃ (100 mL), with water (100 mL), and then concentrated. The resulting residue was purified by over 40 g of silica gel, eluted with a mixed gradient of 1:1 EtOAc:dichloromethane to 10:1 EtOAc:methanol. Product containing fractions were pooled and concentrated to give the desired compound, #70, (3.15 g, 51% yield) as yellow oil. LCMS (Protocol O): m/z 342.9 [M+H]⁺, retention time=0.536 minutes.

Step 2. Synthesis of 3-[(2-{[6-azido-N-(tert-butoxycarbonyl)-L-norleucyl]amino}ethyl)(dimethyl)ammonio]propane-1-sulfonate (#71)

A solution of 6-azido-N²-(tert-butoxycarbonyl)-N-[2-(dimethylamino)ethyl]-L-norleucinamide (3.98 g, 11.6 mmol) and 1,3-propanesultone (2.24 g, 18.4 mmol) in anhydrous EtOAc (70 mL) and the reaction mixture was stirred at 90° C. for 16 h under and atmosphere of nitrogen. Following this period, some white precipitates appeared, and the mixture was allowed to cool to room temperature and stirred overnight. The white precipitates were then filtered, washed with anhydrous EtOAc (3×10 mL), and dried to provide the desired product, #71, (4.31 g, 79.8%) as white solid. LCMS (Protocol Q): m/z 466.3 [M+H]⁺, retention time=2.354 minutes

Step 3. Synthesis of 3-[{2-[(6-azido-L-norleucyl)amino]ethyl}(dimethyl)ammonio]-propane-1-sulfonate (#72)

A solution of 3-[(2-{[6-azido-N-(tert-butoxycarbonyl)-L-norleucyl]amino}ethyl)(dimethyl)ammonio]propane-1-sulfonate (0.2 g, 0.4 mmol) in methanol (10.8 mL) and dichloromethane (2 mL) was treated with a 4 M HCl/dioxane solution (1 mL, 4 mmol) and the solution was stirred at room temperature overnight under an atmosphere of nitrogen. The reaction was concentrated and used directly in the next step without purification. LCMS (Protocol O): m/z 365.2 [M+H]⁺, retention time=0.61 minutes

Step 4. Synthesis of 3-[{2-[(6-azido-N-{[2-(methylsulfonyl)pyrimidin-5-yl]carbonyl}-L-norleucyl)amino]ethyl}(dimethyl)ammonio]propane-1-sulfonate (#73)

A solution of 3-[{2-[(6-azido-L-norleucyl)amino]ethyl}(dimethyl)ammonio]-propane-1-sulfonate hydrochloride (0.2 g, 0.5 mmol) in anhydrous dimethylsulfoxide (1.66 mL) was treated sequentially with N,N-diisopropylethylamine (0.193 g, 1.50 mmol, 0.3 mL), 2-(methylsulfonyl)pyrimidine-5-carboxylic acid (0.111 g, 0.55 mmol), and HATU (0.190 g, 0.50 mmol), and the mixture was stirred for ~1 hour at room temperature. The mixture was then concentrated under vacuum, without heating, and the resulting residue was purified over 12 g of silica gel, eluted with dichloromethane, followed by a gradient of 0-100% methanol in dichloromethane over 20 minutes. Product containing fractions were pooled and concentrated under a stream of nitrogen (without heating) to provide the desired product, #73, as a yellow foam. LCMS (Protocol O): m/z 549.3 [M+H]⁺, retention time=0.49 minutes

Exemplification of Antibody Drug Conjugates

Conjugation Procedure A: Representative procedure for conjugation of linker-payold to the internal disulfides (native cysteine residues) of an antibody. Synthesis of H-C)-#10.

Commercially available Herceptin antibody (Genentech) solution in Dulbecco's Phosphate Buffered Saline (DPBS, Lonza, pH 7.4) was reduced with addition of 2.6 equivalents of tris(2-carboxyethyl)phosphine hydrochloride (TCEP, 5 mM solution in DPBS). The reaction was incubated at 37° C. for 1 h and then allowed to cool to ambient temperature. Conjugation was performed by addition of 7 equivalents of linker-payload [compound #10, 10 mM solution in N,N-dimethylacetamide (DMA)]. Additional DMA was added to reaction mixture to achieve 15% (v/v) total organic solvent component in final reaction mixture. The reaction was incubated for 1 h. at ambient temperature. Next, the reaction mixture was desalted via GE Sephadex gel desalting columns and DPBS (pH 7.4) eluent. Crude conjugate was purified by size exclusion chromatography (SEC) using GE AKTA Explorer system with GE Superdex 200 (10/300 GL) column and DPBS (pH 7.4) eluent.

Conjugation Procedure B: Representative example of conjugations to engineered cysteine residues of antibodies: Preparation of H-(E380C)-#30.

A 20 mM tris(2-carboxyethyl)phosphine (TCEP) solution (133 µL, 100 eq) was added to the antibody (4.2 mg) such that the final antibody concentration was 5 mg/mL (0.84 mL final volume) in PBS buffer containing 5 mM EDTA (507 µL PBS/EDTA). After allowing the reaction to stand at 37° C. for 1.5 hour, the antibody was buffer exchanged into PBS containing 5 mM EDTA using a 50 kD MW cutoff spin concentration device (3×2 mL wash, 10× concentration per cycle). The resulting antibody was diluted up to 824 µL using PBS containing 5 mM EDTA and treated with a freshly prepared 50 mM solution of dehydroascorbate (DHA) in 1:1 PBS/Ethanol (final DHA concentration ~1 mM) and allowed to stand at 4° C. overnight. The antibody/DHA mixture was buffer exchanged into PBS using containing 5 mM EDTA using a 50 kD MW cutoff spin concentration device (3×2 mL wash, 10× concentration per cycle). The resulting antibody (90 µL, 1.5 mg of Ab) was re-suspended in PBS (204.3 µL) and N,N-dimethylacetamide (30 µL) and was treated with 5.7 µL (5× linker payload to Ab) of 10 mM benzothiazole payload (compound 30) in DMA. After standing at 37° C. for 24 hour, the material was buffer exchanged (as above) into PBS (3×2 mL washes, 10× concentration per cycle) to a final volume of 0.4 mL, DAR=1.6 and concentration 2.02 mg/mL.

Exemplified ADCs:

The procedures above were also performed using an anti-CD33 mAb, CD33-11A1-v1417-hG1, and anti Her2 mAb, Her2-PT, using Conjugation Procedure A above and linker-payloads disclosed herein, and to a variety of anti-Her2 mAbs bearing engineered cysteine residues at positions 114 (H-(A114C)) and 183 (H-(kK183C)) and to a variety of anti-CD33 mAbs bearing engineered cysteine residues at positions 290 and 334 (CD33-11A1-v1417-(K290C)-(K334C)) and at positions 334 and 392 (CD33-11A1-v1417-(K334C)-(K392C)) using Conjugation Procedure B above, using the linker-payloads described herein, as outlined in the tables below (Table 1 and Table 2).

TABLE 1
| ADC ID | Conjugation Site | Procedure | Structure |
|---|---|---|---|
| H-(C)-#10 | Internal Cysteines | A | 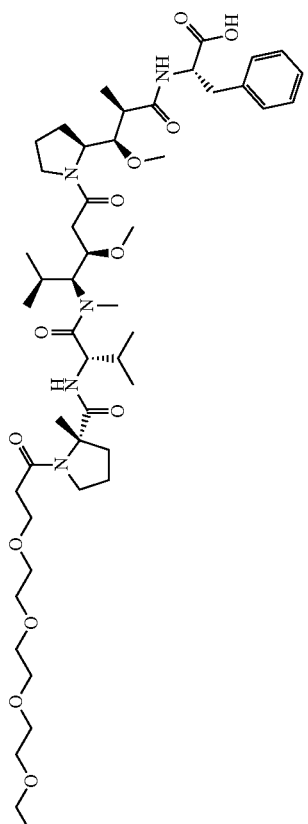 |
| H-(A114C)-#6 | 114C | B | 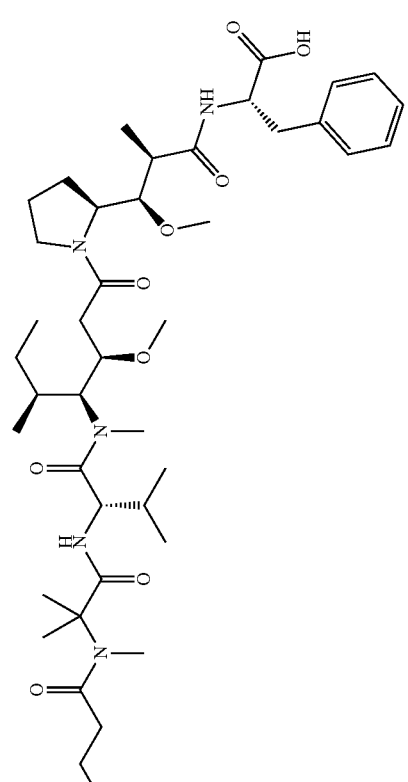 |

TABLE 1-continued

| ADC ID | Conjugation Site | Procedure | Structure |
|---|---|---|---|
| H-(A114C)-#7 | 114C | B | (structure) |
| H-(A114C)-#10 | 114C | B | (structure) |

TABLE 1-continued

| ADC ID | Conjugation Site | Procedure | Structure |
|---|---|---|---|
| H-(A114C)-#11 | 114C | B | (structure) |
| H-(A114C)-#14 | 114C | B | (structure) |
| H-(A114C)-#19 | 114C | B | (structure) |

TABLE 1-continued

| ADC ID | Conjugation Site | Procedure | Structure |
|---|---|---|---|
| H-(A114C)-#26 | 114C | B | 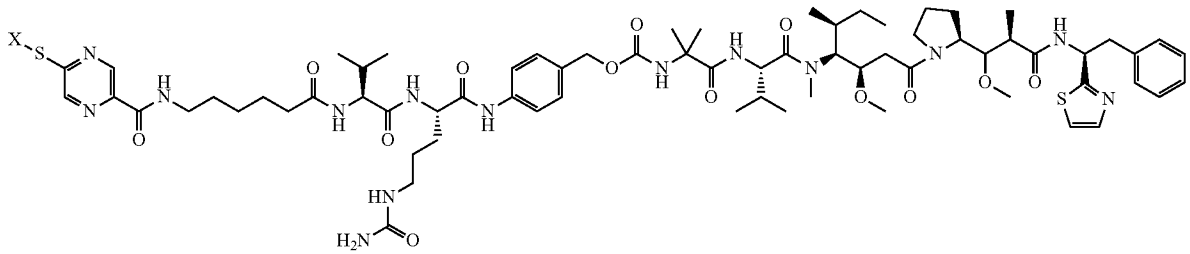 |
| H-(kK183C)-#26 | 183C | B | 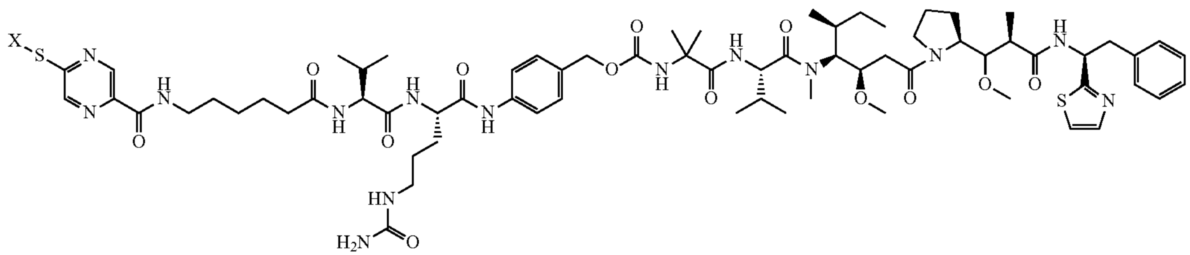 |
| H-(E380C)-#26 | 380C | B | 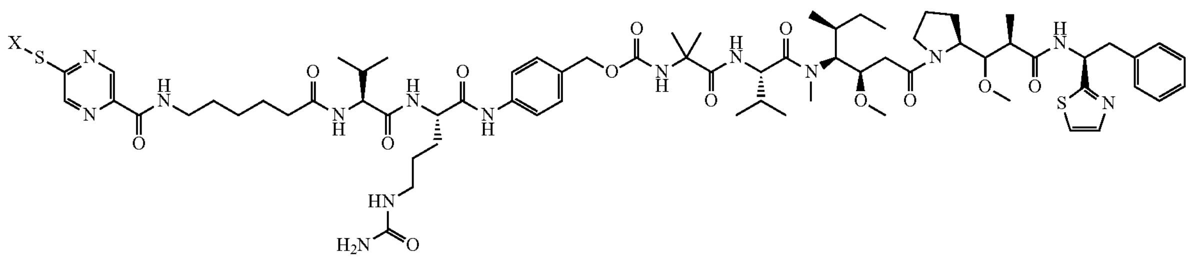 |
| H-(A114C)-#30 | 114C | B | 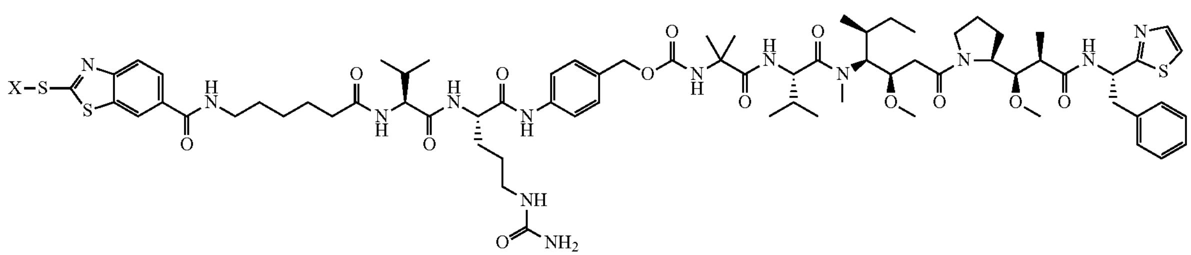 |

TABLE 1-continued

| ADC ID | Conjugation Site | Procedure | Structure |
|---|---|---|---|
| H-(E380C)-#30 | 380C | B | 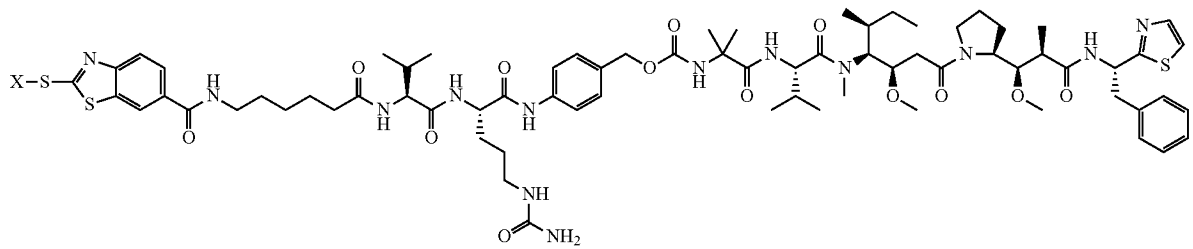 |
| H-(A114C)-#35 | 114C | B | 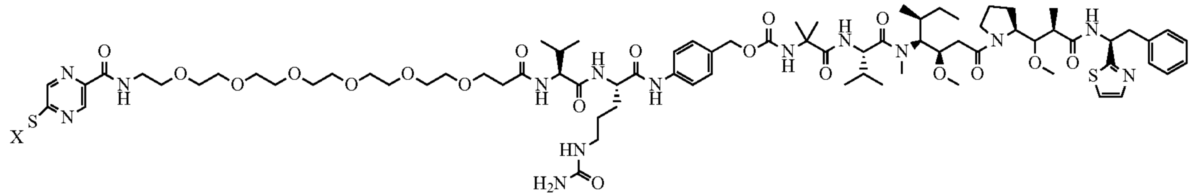 |
| CD33-11A1-v1417-(C)-#39 | Internal Cysteines | A | 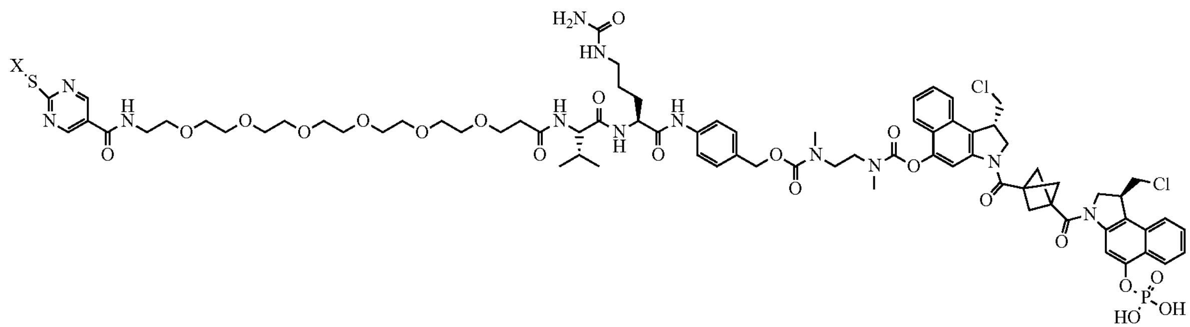 |

TABLE 1-continued

| ADC ID | Conjugation Site | Procedure | Structure |
|---|---|---|---|
| CD33-11A1-v1417-(K290C)(K334C) #39 | 290C/334C | B | 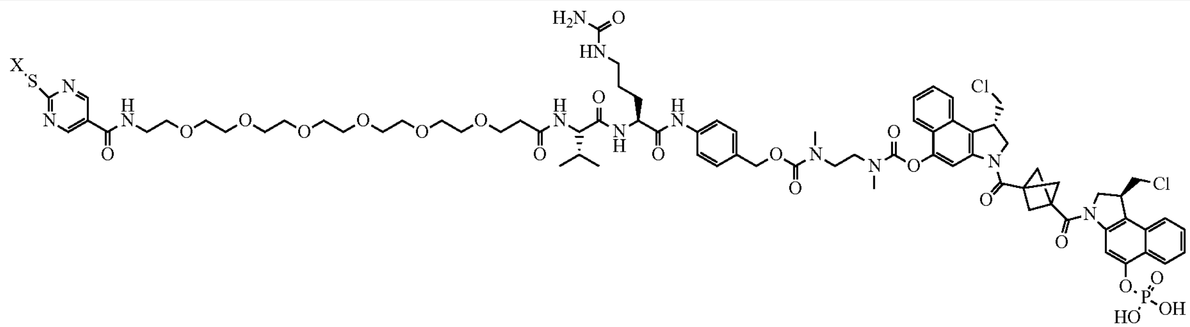 |
| CD33-11A1-v1417-(K334C)(K392C) #39 | 334C/392C | B | |
| H-(A114C)-#43 | 114C | B | 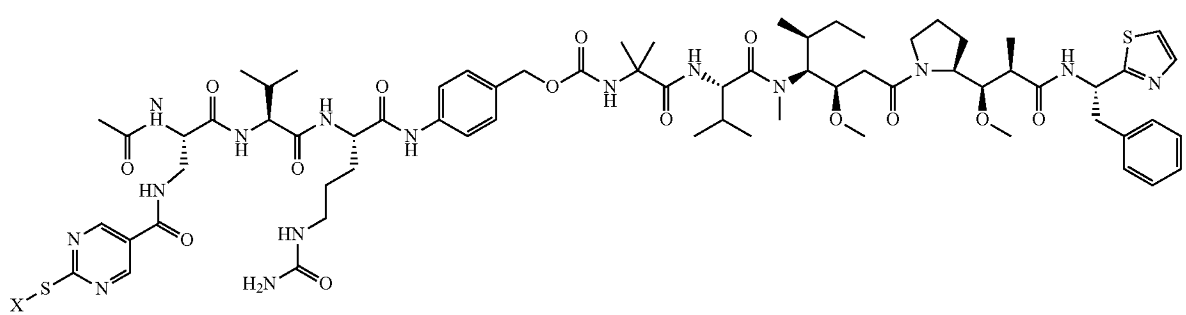 |

TABLE 1-continued
| ADC ID | Conjugation Site | Procedure | Structure |
|---|---|---|---|
| H-(A114C)-#46 | 114C | B | 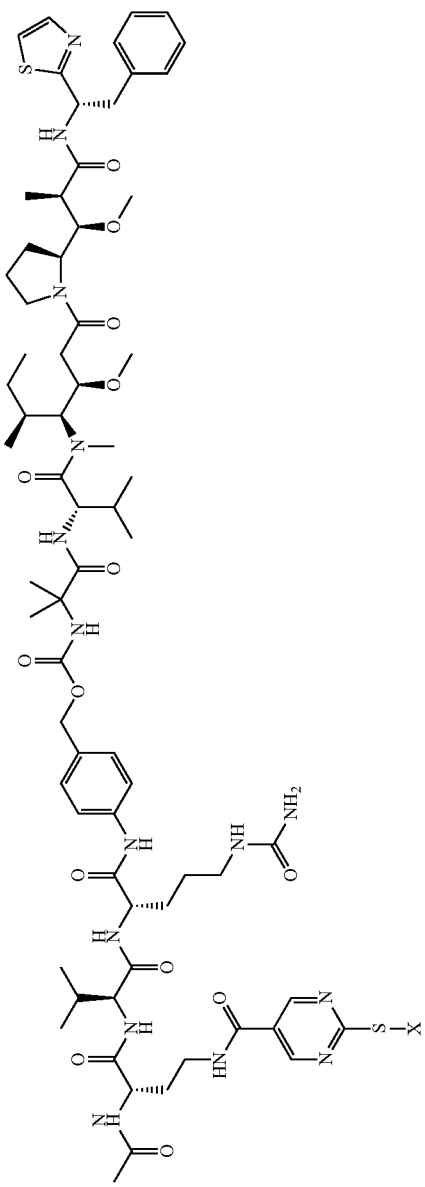 |
| H-(A114C)-#52 | 114C | B | 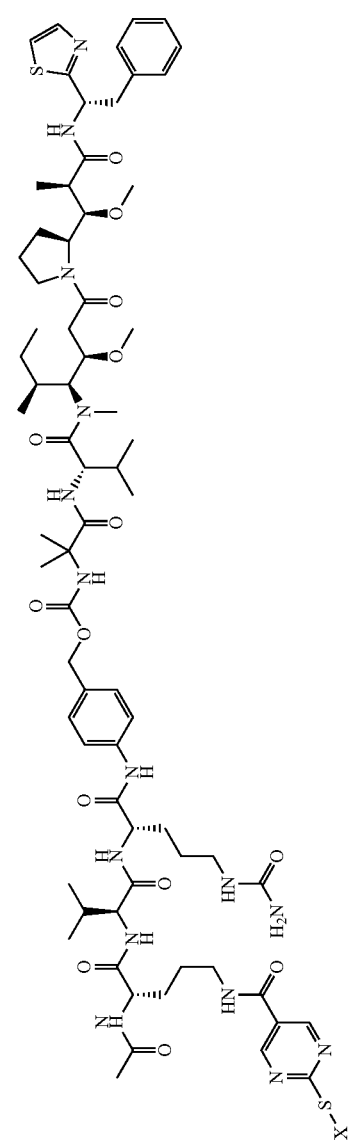 |
| H-(A114C)-#58 | 114C | B | 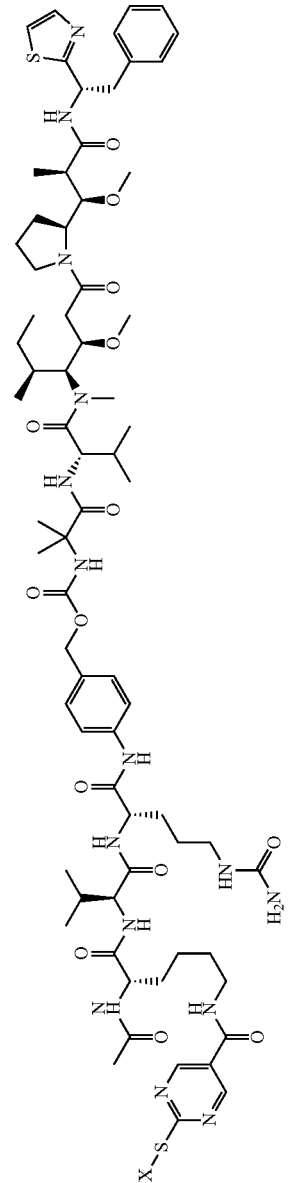 |

TABLE 1-continued
| ADC ID | Conjugation Site | Procedure | Structure |
|---|---|---|---|
| H-(A114C)-#66 | 114C | B | 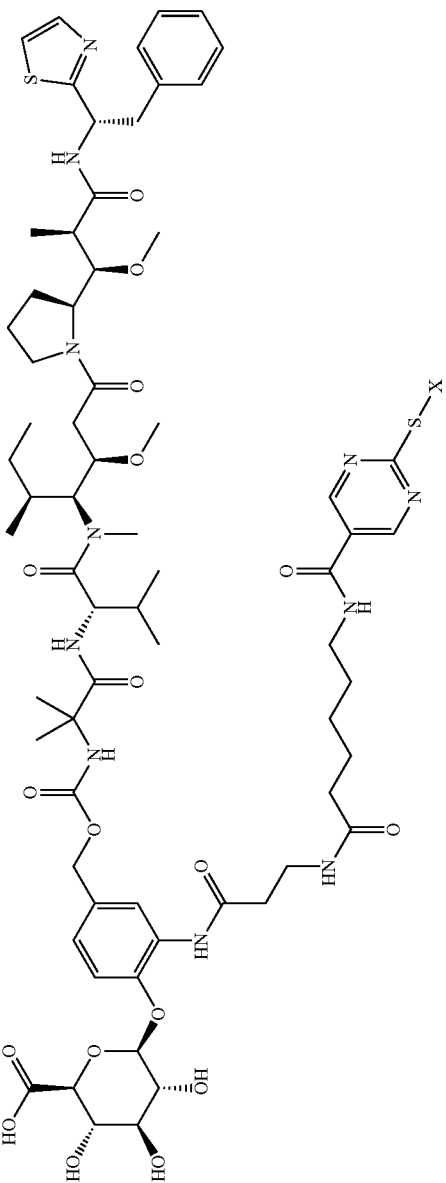 |
In the above table, "X-S" indicates a cysteine residue on the respective monoclonal antibody.

| ADC ID | Theoretical Δ mass per linker-payload | Mass Spectra: SEC-HPLC retention time and HPLC Δ mass for the Light Chain (LC) or Heavy Chain (HC) portion | Loading or Drug per Antibody Ratio (DAR) |
|---|---|---|---|
| H-(C)-#10 | 1169 | SEC (Protocol M): 6.498 minutes; HPLC (Protocol L): LC Δ mass = 1169 | 5.3 |
| H-(A114C)-#6 | 935 | SEC (Protocol M): 6.423minutes; HPLC (Protocol L): LC Δ mass = 938 | 1.9 |
| H-(A114C)-#7 | 990 | SEC (Protocol M): 6.415 minutes; HPLC (Protocol L): LC Δ mass = 988 | 1.9 |
| H-(A114C)-#10 | 1169 | SEC (Protocol M): 6.610 minutes; HPLC (Protocol L): LC Δ mass = 1172 | 2.2 |
| H-(A114C)-#11 | 1169 | SEC (Protocol M): 6.619 minutes; HPLC (Protocol L): LC Δ mass = 1172 | 1.9 |
| H-(A114C)-#14 | 1224 | SEC (Protocol M): 6.438 minutes; HPLC (Protocol L): LC Δ mass = 1223 | 1.9 |
| H-(A114C)-#19 | 1365 | SEC (Protocol M): 6.556 minutes; HPLC (Protocol L): LC Δ mass = 1366 | 2.5 |
| H-(A114C)-#26 | 1365 | SEC (Protocol M): 6.379 minutes; HPLC (Protocol L): LC Δ mass = 1365 | 2 |
| H-(kK183C)-#26 | 1365 | SEC (Protocol M): 6.407 minutes; HPLC (Protocol L): LC Δ mass = 1365 | 2.2 |
| H-(E380C)-#26 | 1365 | SEC (Protocol M): 6.412 minutes; HPLC (Protocol L): LC Δ mass = 1364 | 2.0 |
| H-(A114C)-#30 | 1420 | SEC (Protocol M): 6.466 minutes; HPLC (Protocol L): LC Δ mass = 1420 | 2 |
| H-(E380C)-#30 | 1420 | SEC (Protocol M): 6.450 minutes; HPLC (Protocol L): LC Δ mass = 1420 | 2.0 |
| H-(A114C)-#35 | 1588 | SEC (Protocol M): 6.462 minutes; HPLC (Protocol L): LC Δ mass = 1588 | 2 |
| CD33-11A1-v1417-(C)-#39 | 1626 | SEC (Protocol M): 6.501 minutes; HPLC (Protocol L): LC Δ mass = 1628 | 3.3 |
| CD33-11A1-v1417-(K290C)-(K334C)-#39 | 1626 | SEC (Protocol M): 6.668 minutes; HPLC (Protocol L): LC Δ mass = 1627 | 3 |
| CD33-11A1-v1417-(K334C)-(K392C)-#39 | 1626 | SEC (Protocol M): 6.667 minutes; HPLC (Protocol L): LC Δ mass = 1627 | 3.7 |
| H-(A114C)-#43 | 1381 | SEC (Protocol N): 3.584 minutes; HPLC (Protocol L): LC Δ mass = 1382 | 2.6 |
| H-(A114C)-#46 | 1395 | SEC (Protocol N): 3.506 minutes; HPLC (Protocol L): LC Δ mass = 1395 | 2 |
| H-(A114C)-#52 | 1409 | SEC (Protocol N): 3.504 minutes; HPLC (Protocol L): LC Δ mass = 1408 | 2 |
| H-(A114C)-#58 | 1423 | SEC (Protocol N): 3.504 minutes; HPLC (Protocol L): LC Δ mass = 1421 | 2 |
| H-(A114C)-#66 | 1372 | SEC (Protocol N):3.51 minutes; HPLC (Protocol L): LC Δ mass = 1372 | 1.9 |

Representative Example of GSH Reversibility Study:

To a solution of H-(E380C)-#30 (2.02 mg/ml in 50 mM, pH 7.4 PBS buffer, 99 μL, 0.2 mg Ab) was added additional 50 mM, pH 7.4 PBS buffer (31.3 μL) followed by a 25 mM aqueous glutathione (GSH) solution (2.7 μL) to produce a final protein concentration of 10 μM. A control sample (without GSH) was likewise prepared from 99 μL ADC diluted to 10 μM in PBS. The GSH-treated ADC sample and control ADC sample were incubated at 37° C. and were sampled at 0, 4, and 6 days. Aliquots were reduced with excess TCEP and analyzed for loading by LC/MS. The results of this study and additional studies on other ADCs described herein, along with site-specifically conjugated mc-MMAD (H-(E380C)-mcMMAD) and vc-0101 (H-(E380C)-mcValCitPABC-Aur0101) as comparators, are shown in the table below (Table 3).

TABLE 3

| | T = 0 DAR | T = Day 4 DAR | T = Day 6 DAR |
|---|---|---|---|
| H-(E380C)-#26 (no GSH) | 2.0 | 2.0 | 1.9 |
| H-(E380C)-#26 (GSH) | 2.0 | 1.9 | 1.9 |
| H-(E380C)-#30 (no GSH) | 2.0 | 2.0 | 2.0 |
| H-(E380C)-#30 (GSH) | 2.0 | 2.0 | 1.9 |
| H-(E380C)-mcMMAD (no GSH) | 1.9 | 1.9 | 1.9 |
| H-(E380C)-mcMMAD (GSH) | 1.9 | 1.4 | 1.1 |
| H-(E380C)-mcValCitPABC-Aur0101 (no GSH) | 2.0 | 2.0 | 2.0 |
| H-(E380C)-mcValCitPABC-Aur0101 (GSH) | 2.0 | 1.0 | 0.5 |

In vitro Cell Assay Procedure

Her2-Target expressing (BT474 (breast cancer), N87 (gastric cancer), MDA-MB-361-DYT2 (breast cancer)) or Her2-non-expressing (MDA-MB-468, HT29) cells, or CD33-target expressing HL60, HEL92.1.7, NB4 or CD33-non-expressing (Raji) cells were seeded in 96-well cell culture plates for 24 hours before treatment. Cells were treated with 3-fold serially diluted antibody-drug conjugates or free compounds (i.e., no antibody conjugated to the drug) in duplicate at 10 concentrations. Cell viability was determined by CellTiter 96® AQ$_{ueous}$ One Solution Cell Proliferation MTS Assay (Promega, Madison Wis.) 96 hours after treatment. Relative cell viability was determined as percentage of untreated control. IC50 values were calculated using a four parameter logistic model #203 with XLfit v4.2 (IDBS, Guildford, Surry, UK). Results are shown below in Table 4 (for Herceptin conjugates) or Table 5 (for CD33 conjugates).

TABLE 4

In Vitro Cytotoxicity Data for Herceptin Conjugates

| ADC ID | BT474 GMean IC50 of Antibody (ng/mL) | N87 GMean IC50 of Antibody (ng/mL) | MDA-MB-361-DYT2 GMean IC50 of Antibody (ng/mL) | MDA-MB-468 GMean IC50 of Antibody (ng/mL) | HT29 GMean IC50 of Antibody (ng/mL) |
|---|---|---|---|---|---|
| H-(C)+#10 | 8.53 | 43.50 | 14.59 | 749.14 | >37021 |
| H-(A114C)-#6 | | 114.74 | >27368 | | >77994 |

TABLE 4-continued

In Vitro Cytotoxicity Data for Herceptin Conjugates

| ADC ID | BT474 GMean IC50 of Antibody (ng/mL) | N87 GMean IC50 of Antibody (ng/mL) | MDA-MB-361-DYT2 GMean IC50 of Antibody (ng/mL) | MDA-MB-468 GMean IC50 of Antibody (ng/mL) | HT29 GMean IC50 of Antibody (ng/mL) |
|---|---|---|---|---|---|
| H-(A114C)-#7 | | 517.63 | >78019 | | >78019 |
| H-(A114C)-#10 | | 74.59 | 107.75 | | >67340 |
| H-(A114C)-#11 | 51.08 | 99.02 | >1588 | >77954 | >77922 |
| H-(A114C)-#14 | | 383.87 | >78014 | | >78014 |
| H-(A114C)-#19 | | 31.09 | <12.77 | | 37931 |
| H-(A114C)-#26 | 39.08 | 82.68 | 409.53 | >74086 | 64944 |
| H-(kK183C)-#26 | 15.70 | 40.14 | 593.62 | 59931 | 37019 |
| H-(A114C)-#30 | 39.09 | 72.63 | 357.98 | 67418 | 54582 |
| H-(A114C)-#35 | | 36.79 | 75.18 | | >63083 |
| H-(A114C)-#43 | 16.6 | 33.67 | 22.75 | 18803 | 27311 |
| H-(A114C)-#46 | | 42.90 | 461 | | 12465 |
| H-(A114C)-#52 | | 38.09 | 213.48 | | 24447 |
| H-(A114C)-#58 | | 1433 | 734 | | >60000 |
| H-(A114C)-#66 | 21.70 | 69.18 | 455 | 21644 | 18236 |

TABLE 5

In Vitro Cytotoxicity Data for CD33 Conjugates

| ADC ID | HL-60 GMean IC50 of Antibody (ng/mL) | NB4 GMean IC50 of Antibody (ng/mL) | HEL92.1.7 GMean IC50 of Antibody (ng/mL) | Raji GMean IC50 of Antibody (ng/mL) |
|---|---|---|---|---|
| CD33-(C)-#39 | 3.43 | 14.17 | 1.85 | >1000 |
| CD33-(K290C-K334C)-#39 | 4.58 | 20.78 | 5.21 | >1000 |
| CD33-(K334C-K392C)-#39 | 2.81 | 12.10 | 3.98 | >6323 |

We claim:

1. A compound of Formula (I):

$$R^2-S(O)_2-(Het)-C(O)-N(H)_w-(C(R^1)_2)_r-E_q-(C(R^1)_2)_s-C(O)_t-X_m-Y_n-Z_p-D \quad (I)$$

or a pharmaceutically acceptable salt or solvate thereof, wherein:

Het is a mono-, bi-, or polycyclic heteroaryl ring system having 1-4 heteroatoms,
wherein a carbon atom on said ring system bound to —S(O$_2$)— is adjacent to at least one heteroatom on said ring system, and wherein each heteroatom is independently selected from the group consisting of N, O, and S;

m is 0, 1, 2, 3, 4, or 5;
n is 0, 1, 2, 3, 4, or 5;
p is 0, 1, or 2;
q is 0, 1, 2, 3, 4, 5, 6, 7, 8, 9, or 10;
r is 0, 1, or 2;
s is 0, 1, or 2;
t is 0 or 1;
w is 1 or 2;
each E is independently selected from the group consisting of: —C(R$^1$)$_2$—, —O—C(R$^1$)$_2$—C(R$^1$)$_2$— where r is 2, and —C(R$^1$)$_2$—C(R$^1$)$_2$—O— where s is 1 or 2;
each R$^1$ is independently selected from the group consisting of: H, C$_1$-C$_6$ straight or branched alkyl, C$_2$-C$_6$ straight or branched alkenyl, and C$_2$-C$_6$ straight or branched alkynyl;
R$^2$ is C$_1$-C$_{10}$ alkyl optionally substituted with a halogen or haloalkyl, or C$_5$-C$_{12}$ aryl optionally substituted with a halogen or haloalkyl;
each X is an independently selected amino acid;
each Y is an independently selected amino acid;
each Z is an independently selected spacer element; and
D is dolastatin, MMAD, MMAE, MMAF, PF-06380101, an active agent, a moiety capable of binding to an active agent;
wherein
(a) D is selected from the group consisting of dolastatin, MMAD, MMAE, MMAF and PF-06380101; or
(b) Z is

[chemical structure]

2. The compound of claim 1, or a pharmaceutically acceptable salt or solvate thereof, wherein D is selected from the group consisting of dolastatin, MMAD, MMAE, MMAF, and PF-06380101.

3. The compound of claim 1, or a pharmaceutically acceptable salt or solvate thereof, wherein:
Z is:

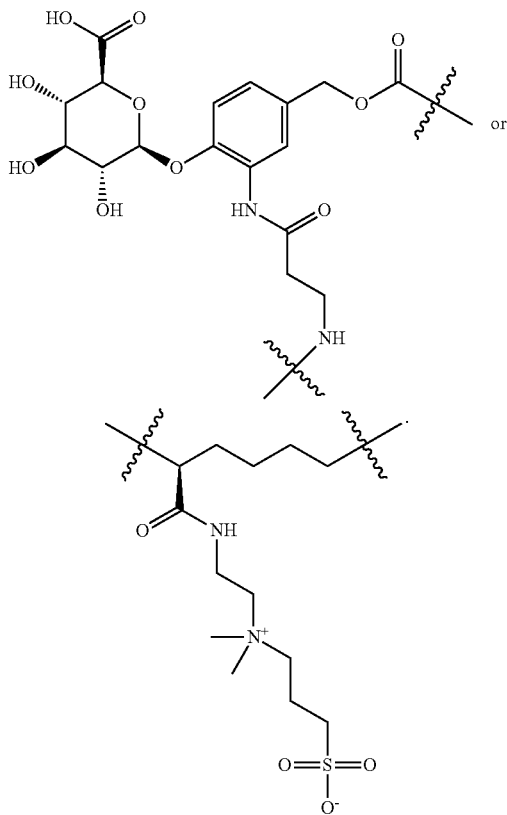

4. A pharmaceutical composition comprising a compound of any one of claims 1, 2, and 3 or a pharmaceutically acceptable salt or solvate thereof, and at least one pharmaceutically acceptable excipient.

5. A method of treating cancer, the method comprising administering to a patient in need thereof a therapeutically effective amount of a compound of any one of claims 1, 2, and 3.

6. The method of claim 5, wherein said cancer is selected from the group consisting of bladder cancer, breast cancer, cervical cancer, colon cancer, endometrial cancer, kidney cancer, lung cancer, esophageal cancer, ovarian cancer, prostate cancer, pancreatic cancer, skin cancer, stomach (gastric) cancer, testicular cancer, leukemias, and lymphomas.

7. A method of treating cancer, the method comprising administering to a patient in need thereof a therapeutically effective amount of a pharmaceutical composition of claim 4.

8. The method of claim 7, wherein said cancer is selected from the group consisting of bladder cancer, breast cancer, cervical cancer, colon cancer, endometrial cancer, kidney cancer, lung cancer, esophageal cancer, ovarian cancer, prostate cancer, pancreatic cancer, skin cancer, stomach (gastric) cancer, testicular cancer, leukemias, and lymphomas.

* * * * *